(12) United States Patent
Jenkins et al.

(10) Patent No.: US 9,259,290 B2
(45) Date of Patent: Feb. 16, 2016

(54) MRI-GUIDED SURGICAL SYSTEMS WITH PROXIMITY ALERTS

(75) Inventors: Kimble L. Jenkins, Memphis, TN (US); Peter Piferi, Orange, CA (US); Michael Guttman, Potomac Falls, VA (US)

(73) Assignee: MRI Interventions, Inc., Irvine, CA (US)

(*) Notice: Subject to any disclaimer, the term of this patent is extended or adjusted under 35 U.S.C. 154(b) by 1255 days.

(21) Appl. No.: 12/795,945

(22) Filed: Jun. 8, 2010

(65) Prior Publication Data

US 2010/0312095 A1 Dec. 9, 2010

Related U.S. Application Data

(60) Provisional application No. 61/185,072, filed on Jun. 8, 2009, provisional application No. 61/187,323, filed on Jun. 16, 2009, provisional application No. 61/219,638, filed on Jun. 23, 2009, provisional application No. 61/261,103, filed on Nov. 13, 2009.

(51) Int. Cl.
*A61B 5/055* (2006.01)
*A61B 19/00* (2006.01)
(Continued)

(52) U.S. Cl.
CPC .............. *A61B 19/56* (2013.01); *A61B 5/415* (2013.01); *A61B 5/418* (2013.01); *A61B 19/50* (2013.01);
(Continued)

(58) Field of Classification Search
CPC ........ A61B 5/415; A61B 5/418; A61B 19/50; A61B 19/5244; A61B 19/56; A61B 18/1492; A61B 2017/00053; A61B 2017/00243; A61B 2018/00029; A61B 2018/00839; A61B 2018/1472; A61B 2019/501; A61B 2019/505; A61B 2019/507; A61B 2019/5251; A61B 5/042; A61B 6/12; A61B 2019/2211; A61B 5/061; A61B 5/065; A61B 8/12; A61B 2019/5265; A61B 2019/5466; A61B 5/066; A61B 2019/5261; A61B 2019/5278; A61B 5/1128; A61B 6/547; A61B 8/4254; A61B 19/54; A61B 1/01; A61B 2017/22042; A61B 2019/5458; A61B 17/12145; G06T 7/004; G06T 7/0089; G06T 7/2046; G06T 19/003; G06T 7/0024; G06T 7/0046; G06T 7/0051; G01R 33/5608; G01R 33/285
USPC .......... 600/411, 424, 434, 463, 439; 601/1–2; 606/41, 34; 703/11
See application file for complete search history.

(56) References Cited

U.S. PATENT DOCUMENTS 3,499,435 A 3/1970 Rockwell et al.
3,661,158 A 5/1972 Berkovits
(Continued)

FOREIGN PATENT DOCUMENTS

EP 0466424 1/1992
EP 0498996 8/1992
(Continued)

OTHER PUBLICATIONS

Chorro et al., "Transcatheter ablation of the sinus node in dogs using high-frequency current," Eur Heart J 11:82-89 (1990).
(Continued)

*Primary Examiner* — Katherine Fernandez
*Assistant Examiner* — Katherine McDonald
(74) *Attorney, Agent, or Firm* — Myers Bigel Sibley & Sajovec, P.A.

(57) ABSTRACT

Systems to facilitate MRI-guided procedures are configured to generate proximity alerts for an MRI-guided procedure associated with at least one target site and/or at least one avoid zone.

12 Claims, 20 Drawing Sheets
(9 of 20 Drawing Sheet(s) Filed in Color)

(51) Int. Cl.

| | |
|---|---|
| A61B 5/00 | (2006.01) |
| A61B 18/14 | (2006.01) |
| A61B 17/00 | (2006.01) |
| A61B 18/00 | (2006.01) |

(52) U.S. Cl.
CPC ............ *A61B 19/5244* (2013.01); *A61B 5/055* (2013.01); *A61B 18/1492* (2013.01); *A61B 2017/00053* (2013.01); *A61B 2017/00243* (2013.01); *A61B 2018/00029* (2013.01); *A61B 2018/00839* (2013.01); *A61B 2018/1472* (2013.01); *A61B 2019/501* (2013.01); *A61B 2019/505* (2013.01); *A61B 2019/507* (2013.01); *A61B 2019/5236* (2013.01); *A61B 2019/5251* (2013.01); *A61B 2019/562* (2013.01)

(56) References Cited

U.S. PATENT DOCUMENTS

| | | | |
|---|---|---|---|
| 4,295,467 | A | 10/1981 | Mann et al. |
| 4,431,005 | A | 2/1984 | McCormick |
| 4,445,501 | A | 5/1984 | Bresler |
| 4,572,198 | A | 2/1986 | Codrington |
| 4,612,930 | A | 9/1986 | Bremer |
| 4,639,365 | A | 1/1987 | Sherry |
| 4,643,186 | A | 2/1987 | Rosen et al. |
| 4,672,972 | A | 6/1987 | Berke |
| 4,754,752 | A | 7/1988 | Ginsburg et al. |
| 4,757,820 | A | 7/1988 | Itoh |
| 4,766,381 | A | 8/1988 | Conturo et al. |
| 4,791,934 | A | 12/1988 | Brunnett |
| 4,793,359 | A | 12/1988 | Sharrow |
| 4,813,429 | A | 3/1989 | Eshel et al. |
| 4,823,812 | A | 4/1989 | Eshel et al. |
| 4,832,023 | A | 5/1989 | Murphy-Chutorian et al. |
| 4,859,950 | A | 8/1989 | Keren |
| 4,932,411 | A | 6/1990 | Fritschy et al. |
| 4,951,672 | A | 8/1990 | Buchwald et al. |
| 4,960,106 | A | 10/1990 | Kubokawa et al. |
| 4,989,608 | A | 2/1991 | Ratner |
| 4,991,580 | A | 2/1991 | Moore |
| 5,019,075 | A | 5/1991 | Spears et al. |
| 5,078,140 | A | 1/1992 | Kwoh |
| 5,095,911 | A | 3/1992 | Pomeranz |
| 5,099,208 | A | 3/1992 | Fitzpatrick et al. |
| 5,125,896 | A | 6/1992 | Hojeibane |
| 5,151,856 | A | 9/1992 | Halmann et al. |
| 5,154,179 | A | 10/1992 | Ratner |
| 5,156,151 | A | 10/1992 | Imran |
| 5,167,233 | A | 12/1992 | Eberle et al. |
| 5,170,789 | A | 12/1992 | Narayan et al. |
| 5,178,618 | A | 1/1993 | Kandarpa |
| 5,190,046 | A | 3/1993 | Shturman |
| 5,190,528 | A | 3/1993 | Fonger et al. |
| 5,209,233 | A | 5/1993 | Holland et al. |
| 5,211,165 | A | 5/1993 | Dumoulin et al. |
| 5,217,010 | A | 6/1993 | Tsitlik et al. |
| 5,218,025 | A | 6/1993 | Kurimoto et al. |
| 5,230,338 | A | 7/1993 | Allen et al. |
| 5,246,438 | A | 9/1993 | Langberg |
| 5,251,120 | A | 10/1993 | Smith |
| 5,251,635 | A | 10/1993 | Dumoulin et al. |
| 5,255,680 | A | 10/1993 | Darrow et al. |
| 5,263,485 | A | 11/1993 | Hickey |
| 5,271,400 | A | 12/1993 | Dumoulin et al. |
| 5,275,163 | A | 1/1994 | McKimmon et al. |
| 5,276,927 | A | 1/1994 | Day |
| 5,284,144 | A | 2/1994 | Delannoy et al. |
| 5,290,266 | A | 3/1994 | Rohling et al. |
| 5,293,868 | A | 3/1994 | Nardella |
| 5,297,549 | A | 3/1994 | Beatty et al. |
| 5,307,808 | A | 5/1994 | Dumoulin et al. |
| 5,307,814 | A | 5/1994 | Kressel et al. |
| 5,318,025 | A | 6/1994 | Dumoulin et al. |
| 5,323,776 | A | 6/1994 | Blakeley et al. |
| 5,323,778 | A | 6/1994 | Kandarpa |
| 5,347,221 | A | 9/1994 | Rubinson |
| 5,348,010 | A | 9/1994 | Schnall et al. |
| 5,352,979 | A | 10/1994 | Conturo |
| 5,353,795 | A | 10/1994 | Souza et al. |
| 5,355,087 | A | 10/1994 | Clairone et al. |
| 5,358,515 | A | 10/1994 | Hurter et al. |
| 5,362,475 | A | 11/1994 | Gries et al. |
| 5,365,928 | A | 11/1994 | Rhinehart et al. |
| 5,370,644 | A | 12/1994 | Langberg |
| 5,377,678 | A | 1/1995 | Dumoulin et al. |
| 5,383,454 | A | 1/1995 | Bucholz |
| 5,384,537 | A | 1/1995 | Ito et al. |
| 5,389,101 | A | 2/1995 | Heilbrun et al. |
| 5,391,199 | A | 2/1995 | Ben-Haim |
| 5,394,873 | A | 3/1995 | Kraemer et al. |
| 5,398,683 | A | 3/1995 | Edwards et al. |
| 5,398,692 | A | 3/1995 | Hickey |
| 5,405,346 | A | 4/1995 | Grundy et al. |
| 5,409,008 | A | 4/1995 | Svenson et al. |
| 5,413,104 | A | 5/1995 | Buijs et al. |
| 5,415,163 | A | 5/1995 | Harms et al. |
| 5,422,576 | A | 6/1995 | Kao et al. |
| 5,433,198 | A | 7/1995 | Desai |
| 5,433,717 | A | 7/1995 | Rubinsky et al. |
| 5,436,564 | A | 7/1995 | Kreger et al. |
| 5,437,277 | A | 8/1995 | Dumoulin et al. |
| 5,443,066 | A | 8/1995 | Dumoulin et al. |
| 5,443,489 | A | 8/1995 | Ben-Haim |
| 5,447,156 | A | 9/1995 | Dumoulin et al. |
| 5,462,055 | A | 10/1995 | Casey et al. |
| 5,480,422 | A | 1/1996 | Ben-Haim |
| 5,507,743 | A | 4/1996 | Edwards et al. |
| 5,512,825 | A | 4/1996 | Atalar et al. |
| 5,529,068 | A | 6/1996 | Hoenninger, III et al. |
| 5,531,227 | A | 7/1996 | Schneider |
| 5,546,940 | A | 8/1996 | Panescu et al. |
| 5,546,951 | A | 8/1996 | Ben-Haim |
| 5,558,093 | A | 9/1996 | Pomeranz |
| 5,568,809 | A | 10/1996 | Ben-Haim |
| 5,569,266 | A | 10/1996 | Siczek |
| 5,577,502 | A | 11/1996 | Darrow et al. |
| 5,588,432 | A | 12/1996 | Crowley |
| 5,590,657 | A | 1/1997 | Cain et al. |
| 5,617,026 | A | 4/1997 | Yoshino et al. |
| 5,622,170 | A | 4/1997 | Schulz |
| 5,634,467 | A | 6/1997 | Nevo |
| 5,643,255 | A | 7/1997 | Organ |
| 5,644,234 | A | 7/1997 | Rasche et al. |
| 5,647,361 | A | 7/1997 | Damadian |
| 5,657,755 | A | 8/1997 | Desai |
| 5,662,108 | A | 9/1997 | Budd et al. |
| 5,671,739 | A | 9/1997 | Darrow et al. |
| 5,682,886 | A | 11/1997 | Delp et al. |
| 5,682,897 | A | 11/1997 | Pomeranz |
| 5,685,878 | A | 11/1997 | Falwell et al. |
| 5,687,725 | A | 11/1997 | Wendt |
| 5,694,945 | A | 12/1997 | Ben-Haim |
| 5,699,801 | A | 12/1997 | Atalar et al. |
| 5,706,823 | A | 1/1998 | Wodlinger |
| 5,713,357 | A | 2/1998 | Meulenbrugge et al. |
| 5,713,946 | A | 2/1998 | Ben-Haim |
| 5,715,822 | A | 2/1998 | Watkins et al. |
| 5,722,402 | A | 3/1998 | Swanson et al. |
| 5,728,079 | A | 3/1998 | Weber et al. |
| 5,730,720 | A * | 3/1998 | Sites et al. ...................... 604/27 |
| 5,738,096 | A | 4/1998 | Ben-Haim |
| 5,739,691 | A | 4/1998 | Hoenninger, III |
| 5,740,808 | A | 4/1998 | Panescu et al. |
| 5,744,958 | A | 4/1998 | Werne |
| 5,749,835 | A | 5/1998 | Glantz |
| 5,754,085 | A | 5/1998 | Danby et al. |
| 5,769,846 | A | 6/1998 | Edwards et al. |
| 5,782,764 | A | 7/1998 | Werne |
| 5,792,055 | A | 8/1998 | McKinnon |
| 5,797,849 | A | 8/1998 | Vesely et al. |
| 5,800,352 | A | 9/1998 | Ferre et al. |
| 5,810,728 | A | 9/1998 | Kuhn |

(56) References Cited

U.S. PATENT DOCUMENTS

| | | | |
|---|---|---|---|
| 5,817,130 A | 10/1998 | Cox et al. |
| 5,820,580 A | 10/1998 | Edwards et al. |
| 5,833,608 A | 11/1998 | Acker |
| 5,836,874 A | 11/1998 | Swanson et al. |
| 5,840,025 A | 11/1998 | Ben-Haim |
| 5,840,031 A | 11/1998 | Crowley |
| 5,864,234 A | 1/1999 | Ludeke |
| 5,868,674 A | 2/1999 | Glowinski et al. |
| 5,882,304 A | 3/1999 | Ehnholm et al. |
| 5,891,047 A | 4/1999 | Lander et al. |
| 5,916,162 A | 6/1999 | Snelton et al. |
| 5,928,145 A | 7/1999 | Ocali et al. |
| 5,938,599 A | 8/1999 | Rasche et al. |
| 5,938,609 A | 8/1999 | Pomeranz |
| 5,944,022 A | 8/1999 | Nardella et al. |
| 5,951,472 A | 9/1999 | Van Vaals et al. |
| 5,961,528 A | 10/1999 | Birk et al. |
| 5,964,705 A | 10/1999 | Truwit et al. |
| 5,964,753 A | 10/1999 | Edwards |
| 5,978,696 A | 11/1999 | VomLehn et al. |
| 6,004,269 A | 12/1999 | Crowley et al. |
| 6,014,579 A | 1/2000 | Pomeranz et al. |
| 6,014,581 A | 1/2000 | Whayne et al. |
| 6,019,725 A | 2/2000 | Vesely et al. |
| 6,023,165 A | 2/2000 | Damadian et al. |
| 6,023,636 A | 2/2000 | Wendt et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,045,553 A | 4/2000 | Iversen et al. |
| 6,052,614 A | 4/2000 | Morris, Sr. et al. |
| 6,052,618 A | 4/2000 | Dahlke et al. |
| 6,066,136 A | 5/2000 | Geistert |
| 6,067,371 A | 5/2000 | Gouge et al. |
| 6,070,094 A | 5/2000 | Swanson et al. |
| 6,071,281 A | 6/2000 | Burnside et al. |
| 6,073,039 A | 6/2000 | Berson |
| 6,076,007 A | 6/2000 | England et al. |
| 6,095,150 A | 8/2000 | Panescu et al. |
| 6,119,032 A | 9/2000 | Martin et al. |
| 6,128,522 A | 10/2000 | Acker et al. |
| 6,129,670 A | 10/2000 | Burdette et al. |
| 6,167,296 A | 12/2000 | Shahidi |
| 6,171,240 B1 | 1/2001 | Young et al. |
| 6,171,241 B1 | 1/2001 | McVeigh et al. |
| 6,179,833 B1 | 1/2001 | Taylor |
| 6,188,219 B1 | 2/2001 | Reeder et al. |
| 6,190,353 B1 | 2/2001 | Makower et al. |
| 6,192,144 B1 | 2/2001 | Holz |
| 6,201,394 B1 | 3/2001 | Danby et al. |
| 6,216,029 B1 | 4/2001 | Paltieli |
| 6,224,553 B1 | 5/2001 | Nevo |
| 6,226,542 B1 | 5/2001 | Reisfeld |
| 6,226,545 B1 | 5/2001 | Gilderdale |
| 6,231,570 B1 | 5/2001 | Tu et al. |
| 6,233,474 B1 | 5/2001 | Lemelson |
| 6,234,970 B1 | 5/2001 | Nevo et al. |
| 6,236,205 B1 | 5/2001 | Lüdeke et al. |
| 6,238,390 B1 | 5/2001 | Tu et al. |
| 6,241,725 B1 | 6/2001 | Cosman |
| 6,246,896 B1 | 6/2001 | Dumoulin et al. |
| 6,256,529 B1 | 7/2001 | Holupka at al. |
| 6,263,229 B1 | 7/2001 | Atalar et al. |
| 6,272,370 B1 | 8/2001 | Gillies et al. |
| 6,272,371 B1 | 8/2001 | Shlomo |
| 6,280,385 B1 | 8/2001 | Melzer et al. |
| 6,284,970 B1 | 9/2001 | Buskmiller et al. |
| 6,284,971 B1 | 9/2001 | Atalar et al. |
| 6,289,233 B1 | 9/2001 | Dumoulin et al. |
| 6,301,496 B1 | 10/2001 | Reisfeld |
| 6,301,497 B1 * | 10/2001 | Neustadter .................. 600/410 |
| 6,317,619 B1 | 11/2001 | Boernert et al. |
| 6,322,558 B1 | 11/2001 | Taylor et al. |
| 6,332,089 B1 | 12/2001 | Acker et al. |
| 6,368,285 B1 | 4/2002 | Osadchy et al. |
| 6,370,434 B1 | 4/2002 | Zhang et al. |
| 6,375,606 B1 | 4/2002 | Garibaldi et al. |
| 6,385,472 B1 | 5/2002 | Hall et al. |
| 6,385,476 B1 | 5/2002 | Osadchy et al. |
| 6,393,314 B1 | 5/2002 | Watkins et al. |
| 6,408,202 B1 | 6/2002 | Lima et al. |
| 6,422,748 B1 | 7/2002 | Shepherd et al. |
| 6,428,537 B1 | 8/2002 | Swanson et al. |
| 6,430,429 B1 | 8/2002 | Van Vaals |
| 6,431,173 B1 | 8/2002 | Hoffmann |
| 6,456,867 B2 | 9/2002 | Reisfeld |
| 6,470,204 B1 | 10/2002 | Uzgiris et al. |
| 6,475,223 B1 | 11/2002 | Werp et al. |
| 6,487,431 B1 | 11/2002 | Iwano et al. |
| 6,487,437 B1 | 11/2002 | Viswanathan et al. |
| 6,490,473 B1 | 12/2002 | Katznelson et al. |
| 6,506,189 B1 | 1/2003 | Rittman, II et al. |
| 6,516,213 B1 | 2/2003 | Nevo |
| 6,522,913 B2 | 2/2003 | Swanson et al. |
| 6,529,758 B2 | 3/2003 | Shahidi |
| 6,529,764 B1 | 3/2003 | Kato et al. |
| 6,534,982 B1 | 3/2003 | Jakab |
| 6,535,755 B2 | 3/2003 | Ehnholm |
| 6,546,273 B2 | 4/2003 | Suzuki et al. |
| 6,546,279 B1 | 4/2003 | Bova et al. |
| 6,549,800 B1 | 4/2003 | Atalar et al. |
| 6,556,009 B2 | 4/2003 | Kellman et al. |
| 6,556,695 B1 | 4/2003 | Packer et al. |
| 6,558,333 B2 | 5/2003 | Gilboa et al. |
| 6,558,382 B2 | 5/2003 | Jahns et al. |
| 6,575,969 B1 | 6/2003 | Rittman, II et al. |
| 6,591,128 B1 | 7/2003 | Wu et al. |
| 6,591,130 B2 | 7/2003 | Shahidi |
| 6,593,884 B1 | 7/2003 | Gilboa et al. |
| 6,594,517 B1 | 7/2003 | Nevo |
| 6,597,935 B2 | 7/2003 | Prince et al. |
| 6,600,319 B2 | 7/2003 | Golan |
| 6,603,997 B2 | 8/2003 | Doody |
| 6,606,513 B2 | 8/2003 | Lardo et al. |
| 6,626,902 B1 | 9/2003 | Kucharczyk et al. |
| 6,628,980 B2 | 9/2003 | Atalar et al. |
| 6,633,773 B1 | 10/2003 | Reisfeld |
| 6,640,126 B2 | 10/2003 | Chang |
| 6,643,535 B2 | 11/2003 | Damasco et al. |
| 6,650,923 B1 | 11/2003 | Lesh et al. |
| 6,650,927 B1 | 11/2003 | Keidar |
| 6,654,628 B1 | 11/2003 | Silber et al. |
| 6,668,184 B1 | 12/2003 | Kleiman |
| 6,671,538 B1 * | 12/2003 | Ehnholm ............... A61B 19/20 382/131 |
| 6,675,033 B1 | 1/2004 | Lardo et al. |
| 6,675,037 B1 | 1/2004 | Tsekos |
| 6,687,530 B2 | 2/2004 | Dumoulin |
| 6,690,963 B2 | 2/2004 | Ben-Haim et al. |
| 6,701,176 B1 | 3/2004 | Halperin et al. |
| 6,702,835 B2 | 3/2004 | Ginn |
| 6,711,429 B1 | 3/2004 | Gilboa et al. |
| 6,714,809 B2 | 3/2004 | Lee et al. |
| 6,725,079 B2 | 4/2004 | Zuk et al. |
| 6,740,883 B1 | 5/2004 | Stodilka et al. |
| 6,741,879 B2 | 5/2004 | Chang |
| 6,741,882 B2 | 5/2004 | Schäffter et al. |
| 6,743,248 B2 | 6/2004 | Edwards et al. |
| 6,771,067 B2 | 8/2004 | Kellman et al. |
| 6,780,183 B2 | 8/2004 | Jimenez, Jr. et al. |
| 6,785,572 B2 | 8/2004 | Yanof et al. |
| 6,788,062 B2 | 9/2004 | Schweikard et al. |
| 6,788,967 B2 | 9/2004 | Ben-Haim et al. |
| 6,793,664 B2 | 9/2004 | Mazzocchi et al. |
| 6,794,872 B2 | 9/2004 | Meyer et al. |
| 6,813,512 B2 | 11/2004 | Aldefeld et al. |
| 6,829,509 B1 | 12/2004 | MacDonald et al. |
| 6,847,210 B1 | 1/2005 | Eydelman et al. |
| 6,847,837 B1 | 1/2005 | Melzer et al. |
| 6,853,856 B2 | 2/2005 | Yanof et al. |
| 6,871,086 B2 | 3/2005 | Nevo et al. |
| 6,879,160 B2 | 4/2005 | Jakab |
| 6,892,090 B2 | 5/2005 | Verard et al. |

(56) References Cited

U.S. PATENT DOCUMENTS

| | | | |
|---|---|---|---|
| 6,892,091 B1 | 5/2005 | Ben-Haim et al. |
| 6,896,678 B2 | 5/2005 | Tweardy |
| 6,898,302 B1 | 5/2005 | Brummer |
| 6,898,454 B2 | 5/2005 | Atalar et al. |
| 6,904,307 B2 | 6/2005 | Karmarkar et al. |
| 6,920,347 B2 | 7/2005 | Simon et al. |
| 6,941,166 B2 | 9/2005 | MacAdam et al. |
| 6,949,929 B2 | 9/2005 | Gray et al. |
| 6,950,543 B2 | 9/2005 | King et al. |
| 6,958,035 B2 | 10/2005 | Friedman et al. |
| 6,961,602 B2 | 11/2005 | Fuimaono et al. |
| 6,961,608 B2 | 11/2005 | Hoshino et al. |
| 6,975,896 B2 | 12/2005 | Ehnholm et al. |
| 6,980,865 B1 | 12/2005 | Wang et al. |
| 6,985,775 B2 | 1/2006 | Reinke et al. |
| 6,988,001 B2 | 1/2006 | Greatbatch et al. |
| 6,994,094 B2 | 2/2006 | Schwartz |
| 6,996,430 B1 | 2/2006 | Gilboa et al. |
| 7,001,383 B2 | 2/2006 | Keidar |
| 7,020,312 B2 | 3/2006 | Desmedt et al. |
| 7,027,851 B2 | 4/2006 | Mejia |
| 7,027,854 B2 | 4/2006 | Fuderer et al. |
| 7,047,060 B1 | 5/2006 | Wu |
| 7,048,716 B1 | 5/2006 | Kucharczyk et al. |
| 7,056,294 B2 | 6/2006 | Khairkhahan et al. |
| 7,081,748 B2 | 7/2006 | Jakab |
| 7,082,325 B2 | 7/2006 | Hashimshony et al. |
| 7,089,045 B2 | 8/2006 | Fuimaono et al. |
| 7,095,890 B2 | 8/2006 | Paragios et al. |
| 7,096,057 B2 | 8/2006 | Hockett et al. |
| 7,099,712 B2 | 8/2006 | Fuimaono et al. |
| 7,123,013 B2 | 10/2006 | Gray |
| 7,133,714 B2 | 11/2006 | Karmarkar et al. |
| 7,134,438 B2 | 11/2006 | Makower et al. |
| 7,154,498 B2 | 12/2006 | Cowan et al. |
| 7,155,271 B2 | 12/2006 | Halperin et al. |
| 7,162,293 B2 | 1/2007 | Weiss |
| 7,187,964 B2 | 3/2007 | Khoury |
| 7,204,840 B2 | 4/2007 | Skakoon |
| 7,205,768 B2 | 4/2007 | Schulz et al. |
| 7,209,777 B2 | 4/2007 | Saranathan |
| 7,211,082 B2 | 5/2007 | Hall et al |
| 7,220,265 B2 | 5/2007 | Chanduszko et al. |
| 7,225,012 B1 | 5/2007 | Susil et al. |
| 7,228,164 B2 | 6/2007 | Fuimaono et al. |
| 7,236,816 B2 | 6/2007 | Kumar et al. |
| 7,239,400 B2 | 7/2007 | Bock |
| 7,241,283 B2 | 7/2007 | Putz |
| 7,255,691 B2 | 8/2007 | Tolkoff et al. |
| 7,263,397 B2 | 8/2007 | Hauck et al. |
| 7,276,905 B2 | 10/2007 | Tamaroff et al. |
| 7,280,863 B2 | 10/2007 | Shachar |
| 7,285,119 B2 | 10/2007 | Stewart |
| 7,289,843 B2 | 10/2007 | Beatty et al. |
| 7,302,285 B2 | 11/2007 | Fuimaono et al. |
| 7,306,593 B2 | 12/2007 | Keidar et al. |
| 7,307,420 B2 | 12/2007 | Dumoulin |
| 7,308,299 B2 | 12/2007 | Burrell et al. |
| 7,311,705 B2 | 12/2007 | Sra |
| 7,320,695 B2 | 1/2008 | Carroll |
| 7,343,195 B2 | 3/2008 | Strommer et al. |
| 7,347,829 B2 | 3/2008 | Mark et al. |
| 7,363,090 B2 | 4/2008 | Halperin et al. |
| 7,386,339 B2 | 6/2008 | Strommer et al. |
| 7,398,116 B2 | 7/2008 | Edwards |
| 7,412,276 B2 | 8/2008 | Halperin et al. |
| 7,415,301 B2 | 8/2008 | Hareyama et al. |
| 7,418,289 B2 | 8/2008 | Hyde et al. |
| 7,422,568 B2 | 9/2008 | Yang et al. |
| 7,440,792 B2 | 10/2008 | Eggers |
| 7,463,920 B2 | 12/2008 | Purdy |
| 7,473,843 B2 | 1/2009 | Wang et al. |
| 7,474,913 B2 | 1/2009 | Durlak |
| 7,477,054 B2 | 1/2009 | Hoogenraad et al. |
| 7,480,398 B2 | 1/2009 | Kleen et al. |
| 7,483,732 B2 | 1/2009 | Zhong et al. |
| 7,495,438 B2 | 2/2009 | Prince et al. |
| 7,499,743 B2 | 3/2009 | Vass et al. |
| 7,505,808 B2 | 3/2009 | Anderson et al. |
| 7,505,809 B2 | 3/2009 | Strommer et al. |
| 7,505,810 B2 | 3/2009 | Harlev et al. |
| 7,542,793 B2 | 6/2009 | Wu et al. |
| 7,551,953 B2 | 6/2009 | Lardo et al. |
| 7,560,931 B2 | 7/2009 | Nabetani |
| 7,561,906 B2 | 7/2009 | Atalar et al. |
| 7,587,234 B2 | 9/2009 | Owens et al. |
| 7,593,558 B2 | 9/2009 | Boese |
| 7,599,730 B2 | 10/2009 | Hunter et al. |
| 7,602,190 B2 | 10/2009 | Piferi et al. |
| 7,606,611 B2 | 10/2009 | Speier |
| 7,609,862 B2 | 10/2009 | Black |
| 7,623,903 B2 | 11/2009 | Wacker |
| 7,632,265 B2 | 12/2009 | Hauck et al. |
| 7,660,623 B2 | 2/2010 | Hunter et al. |
| 7,689,264 B2 | 3/2010 | Nauerth |
| 7,697,972 B2 | 4/2010 | Verard et al. |
| 7,720,520 B2 | 5/2010 | Willis |
| 7,725,157 B2 | 5/2010 | Dumoulin et al. |
| 7,725,160 B2 | 5/2010 | Weber |
| 7,725,161 B2 | 5/2010 | Karmarkar et al. |
| 7,726,708 B2 | 6/2010 | Bourrieres |
| 7,751,865 B2 | 7/2010 | Jascob et al. |
| 7,769,427 B2 | 8/2010 | Shachar |
| 7,777,485 B2 | 8/2010 | Dumoulin et al. |
| 7,787,935 B2 | 8/2010 | Dumoulin et al. |
| 7,811,294 B2 | 10/2010 | Strommer et al. |
| 7,815,623 B2 | 10/2010 | Bankiewicz |
| 7,822,460 B2 | 10/2010 | Halperin et al. |
| 7,840,253 B2 | 11/2010 | Tremblay et al. |
| 7,841,986 B2 | 11/2010 | He |
| 7,844,319 B2 | 11/2010 | Susil et al. |
| 7,844,320 B2 | 11/2010 | Shahidi |
| 7,848,788 B2 | 12/2010 | Tulley et al. |
| 7,853,332 B2 | 12/2010 | Olsen |
| 7,881,769 B2 | 2/2011 | Sobe |
| 7,894,877 B2 | 2/2011 | Lewin et al. |
| 7,920,911 B2 | 4/2011 | Hoshino et al. |
| 7,999,547 B2 | 8/2011 | Green et al. |
| 8,010,177 B2 | 8/2011 | Csavoy et al. |
| 8,016,857 B2 | 9/2011 | Sater et al. |
| 8,162,975 B2 | 4/2012 | Benjamin et al. |
| 8,221,442 B2 | 7/2012 | Domb et al. |
| 8,473,030 B2 | 6/2013 | Greenan et al. |
| 2001/0025142 A1 | 9/2001 | Wessels et al. |
| 2002/0019629 A1 | 2/2002 | Dietz et al. |
| 2002/0019644 A1 | 2/2002 | Hastings et al. |
| 2002/0055678 A1 | 5/2002 | Scott et al. |
| 2002/0058868 A1 | 5/2002 | Hoshino et al. |
| 2002/0072712 A1 | 6/2002 | Nool et al. |
| 2002/0103430 A1 | 8/2002 | Hastings et al. |
| 2002/0122530 A1 | 9/2002 | Erbel et al. |
| 2002/0169371 A1 | 11/2002 | Gilderdale |
| 2002/0177771 A1 | 11/2002 | Guttman et al. |
| 2003/0055332 A1 | 3/2003 | Daum et al. |
| 2003/0074011 A1 | 4/2003 | Gilboa et al. |
| 2003/0078494 A1* | 4/2003 | Panescu et al. ............... 600/424 |
| 2003/0088181 A1 | 5/2003 | Gleich et al. |
| 2003/0093067 A1 | 5/2003 | Panescu |
| 2003/0097149 A1 | 5/2003 | Edwards et al. |
| 2003/0100829 A1 | 5/2003 | Zhong et al. |
| 2003/0158477 A1 | 8/2003 | Panescu |
| 2003/0208252 A1 | 11/2003 | O'Boyle et al. |
| 2003/0216642 A1 | 11/2003 | Pepin et al. |
| 2004/0006268 A1 | 1/2004 | Gilboa et al. |
| 2004/0015075 A1 | 1/2004 | Kimchy et al. |
| 2004/0024308 A1 | 2/2004 | Wickline et al. |
| 2004/0030244 A1 | 2/2004 | Garibaldi et al. |
| 2004/0034297 A1 | 2/2004 | Darrow et al. |
| 2004/0049121 A1 | 3/2004 | Yaron |
| 2004/0054279 A1 | 3/2004 | Hanley |
| 2004/0073088 A1 | 4/2004 | Friedman et al. |
| 2004/0082948 A1 | 4/2004 | Stewart et al. |
| 2004/0092813 A1 | 5/2004 | Takizawa et al. |
| 2004/0111022 A1 | 6/2004 | Grabek et al. |

(56) References Cited

U.S. PATENT DOCUMENTS

| | | |
|---|---|---|
| 2004/0116800 A1 | 6/2004 | Helfer et al. |
| 2004/0124838 A1 | 7/2004 | Duerk et al. |
| 2004/0143180 A1 | 7/2004 | Zhong et al. |
| 2004/0152968 A1 | 8/2004 | Iversen et al. |
| 2004/0152974 A1 | 8/2004 | Solomon |
| 2004/0171934 A1 | 9/2004 | Khan et al. |
| 2004/0181160 A1 | 9/2004 | Rudy |
| 2004/0181177 A1 | 9/2004 | Lee |
| 2004/0199072 A1 | 10/2004 | Sprouse et al. |
| 2004/0220470 A1 | 11/2004 | Karmarkar et al. |
| 2004/0225213 A1 | 11/2004 | Wang et al. |
| 2005/0010105 A1 | 1/2005 | Sra |
| 2005/0014995 A1 | 1/2005 | Amundson |
| 2005/0054910 A1 | 3/2005 | Tremblay et al. |
| 2005/0054913 A1 | 3/2005 | Duerk et al. |
| 2005/0113874 A1 | 5/2005 | Connelly |
| 2005/0119556 A1 | 6/2005 | Gillies et al. |
| 2005/0143651 A1 | 6/2005 | Verard et al. |
| 2005/0154279 A1 | 7/2005 | Li et al. |
| 2005/0154281 A1 | 7/2005 | Xue et al. |
| 2005/0154282 A1 | 7/2005 | Li et al. |
| 2005/0165301 A1 | 7/2005 | Smith et al. |
| 2005/0171427 A1 | 8/2005 | Nevo |
| 2005/0215886 A1 | 9/2005 | Schmidt |
| 2005/0222509 A1 | 10/2005 | Neason |
| 2005/0228252 A1 | 10/2005 | Neason |
| 2005/0256398 A1 | 11/2005 | Hastings et al. |
| 2005/0288599 A1 | 12/2005 | MacAdam et al. |
| 2006/0009756 A1 | 1/2006 | Francischelli et al. |
| 2006/0025677 A1 | 2/2006 | Verard et al. |
| 2006/0052706 A1 | 3/2006 | Hynynen |
| 2006/0084867 A1* | 4/2006 | Tremblay et al. ............. 600/434 |
| 2006/0089624 A1* | 4/2006 | Voegele et al. ................ 606/1 |
| 2006/0100506 A1 | 5/2006 | Halperin et al. |
| 2006/0106303 A1 | 5/2006 | Karmarkar et al. |
| 2006/0116576 A1* | 6/2006 | McGee et al. ................ 600/434 |
| 2006/0142657 A1 | 6/2006 | Quaid et al. |
| 2006/0184011 A1 | 8/2006 | Macaulay et al. |
| 2006/0224062 A1 | 10/2006 | Aggarwal et al. |
| 2006/0241392 A1 | 10/2006 | Feinstein |
| 2006/0247521 A1 | 11/2006 | McGee |
| 2006/0247684 A1 | 11/2006 | Halperin et al. |
| 2006/0258934 A1 | 11/2006 | Zenge et al. |
| 2007/0014454 A1* | 1/2007 | Sawyer et al. ................ 382/128 |
| 2007/0032826 A1 | 2/2007 | Schwartz |
| 2007/0049817 A1 | 3/2007 | Preiss |
| 2007/0055328 A1 | 3/2007 | Mayse et al. |
| 2007/0055455 A1* | 3/2007 | Wei et al. ......................... 702/19 |
| 2007/0062547 A1 | 3/2007 | Pappone |
| 2007/0073135 A1 | 3/2007 | Lee |
| 2007/0073179 A1 | 3/2007 | Afonso |
| 2007/0083195 A1 | 4/2007 | Werneth |
| 2007/0088295 A1 | 4/2007 | Bankiewicz |
| 2007/0088416 A1 | 4/2007 | Atalar et al. |
| 2007/0100223 A1 | 5/2007 | Liao et al. |
| 2007/0100232 A1 | 5/2007 | Hiller et al. |
| 2007/0106148 A1 | 5/2007 | Dumoulin |
| 2007/0112398 A1 | 5/2007 | Stevenson |
| 2007/0156042 A1 | 7/2007 | Unal et al. |
| 2007/0167726 A1 | 7/2007 | Unal et al. |
| 2007/0167736 A1 | 7/2007 | Dietz et al. |
| 2007/0167738 A1 | 7/2007 | Timinger et al. |
| 2007/0167745 A1 | 7/2007 | Case |
| 2007/0185485 A1 | 8/2007 | Hauck et al. |
| 2007/0208260 A1 | 9/2007 | Afonso |
| 2007/0233238 A1 | 10/2007 | Huynh et al. |
| 2007/0238970 A1 | 10/2007 | Kozerke et al. |
| 2007/0238978 A1 | 10/2007 | Kumar et al. |
| 2007/0238985 A1 | 10/2007 | Smith et al. |
| 2007/0249934 A1 | 10/2007 | Aksit et al. |
| 2007/0265521 A1 | 11/2007 | Redel et al. |
| 2007/0265642 A1 | 11/2007 | Chanduszko et al. |
| 2007/0270741 A1 | 11/2007 | Hassett et al. |
| 2007/0293724 A1 | 12/2007 | Saadat et al. |
| 2008/0009700 A1* | 1/2008 | Dumoulin et al. ............ 600/410 |
| 2008/0021336 A1 | 1/2008 | Dobak, III |
| 2008/0027696 A1* | 1/2008 | Pedain et al. .................... 703/11 |
| 2008/0032249 A1 | 2/2008 | Scommegna et al. |
| 2008/0033278 A1 | 2/2008 | Assif |
| 2008/0033281 A1 | 2/2008 | Kroeckel |
| 2008/0039897 A1 | 2/2008 | Kluge et al. |
| 2008/0049376 A1 | 2/2008 | Stevenson |
| 2008/0058635 A1 | 3/2008 | Halperin et al. |
| 2008/0097189 A1 | 4/2008 | Dumoulin et al. |
| 2008/0097191 A1 | 4/2008 | Dumoulin et al. |
| 2008/0119919 A1 | 5/2008 | Atalar et al. |
| 2008/0125802 A1 | 5/2008 | Carroll |
| 2008/0130965 A1 | 6/2008 | Avinash et al. |
| 2008/0139925 A1 | 6/2008 | Lubock et al. |
| 2008/0143459 A1 | 6/2008 | Vernickel et al. |
| 2008/0154253 A1 | 6/2008 | Damasco et al. |
| 2008/0171931 A1 | 7/2008 | Maschke |
| 2008/0177183 A1* | 7/2008 | Courtney et al. ............. 600/463 |
| 2008/0183070 A1 | 7/2008 | Unal et al. |
| 2008/0190438 A1 | 8/2008 | Harlev et al. |
| 2008/0214931 A1 | 9/2008 | Dickfield |
| 2008/0215008 A1 | 9/2008 | Nance et al. |
| 2008/0231264 A1 | 9/2008 | Krueger et al. |
| 2008/0243081 A1 | 10/2008 | Nance et al. |
| 2008/0243218 A1 | 10/2008 | Bottomley et al. |
| 2008/0262584 A1 | 10/2008 | Bottomley et al. |
| 2008/0275395 A1 | 11/2008 | Asbury et al. |
| 2008/0287773 A1 | 11/2008 | Harvey et al. |
| 2008/0306375 A1 | 12/2008 | Sayler et al. |
| 2008/0306376 A1 | 12/2008 | Hyde et al. |
| 2009/0012390 A1 | 1/2009 | Pescatore et al. |
| 2009/0079431 A1 | 3/2009 | Piferi et al. |
| 2009/0082783 A1 | 3/2009 | Piferi |
| 2009/0088627 A1 | 4/2009 | Piferi et al. |
| 2009/0102479 A1 | 4/2009 | Smith et al. |
| 2009/0112082 A1 | 4/2009 | Piferi et al. |
| 2009/0112084 A1 | 4/2009 | Piferi et al. |
| 2009/0118610 A1 | 5/2009 | Karmarkar et al. |
| 2009/0131783 A1 | 5/2009 | Jenkins et al. |
| 2009/0143696 A1 | 6/2009 | Najafi et al. |
| 2009/0171184 A1 | 7/2009 | Jenkins et al. |
| 2009/0171421 A1 | 7/2009 | Atalar et al. |
| 2009/0306643 A1 | 12/2009 | Pappone et al. |
| 2010/0066371 A1 | 3/2010 | Vij |
| 2010/0198052 A1 | 8/2010 | Jenkins et al. |
| 2010/0286725 A1 | 11/2010 | Benjamin et al. |
| 2010/0312094 A1 | 12/2010 | Guttman et al. |
| 2010/0312095 A1 | 12/2010 | Jenkins et al. |
| 2010/0312096 A1 | 12/2010 | Guttman et al. |
| 2010/0317961 A1 | 12/2010 | Jenkins et al. |
| 2010/0317962 A1 | 12/2010 | Jenkins et al. |
| 2011/0040175 A1 | 2/2011 | Shahidi |
| 2011/0106131 A1 | 5/2011 | Argentine |
| 2011/0270192 A1 | 11/2011 | Anderson et al. |

FOREIGN PATENT DOCUMENTS

| | | |
|---|---|---|
| EP | 0557127 | 8/1993 |
| EP | 0673621 | 9/1995 |
| EP | 0701835 | 3/1996 |
| EP | 0701836 | 3/1996 |
| EP | 0702976 | 3/1996 |
| EP | 0732082 | 9/1996 |
| EP | 1 750 215 A1 | 2/2007 |
| EP | 1 943 974 A1 | 7/2008 |
| JP | 01-212569 | 8/1989 |
| JP | 2006-070902 | 3/1994 |
| JP | 09-094238 | 4/1997 |
| JP | 09-238924 | 9/1997 |
| JP | 09-299346 | 11/1997 |
| JP | 2001-238959 | 9/2001 |
| JP | 2003-325475 | 11/2003 |
| JP | 2004-113808 | 4/2004 |
| JP | 2006-334259 | 12/2006 |
| WO | WO/87/04080 | 7/1987 |
| WO | WO/92/10213 | 6/1992 |
| WO | WO/94/23782 | 10/1994 |
| WO | WO/95/04398 | 2/1995 |
| WO | WO/96/12972 | 5/1996 |

(56) References Cited

FOREIGN PATENT DOCUMENTS

| WO | WO/97/29685 | 8/1997 |
|----|----|----|
| WO | WO/97/29710 | 8/1997 |
| WO | WO/97/40396 | 10/1997 |
| WO | WO/98/52461 | 11/1998 |
| WO | WO/98/55016 | 12/1998 |
| WO | WO/99/00052 | 1/1999 |
| WO | WO/99/16352 | 4/1999 |
| WO | WO/00/10456 | 3/2000 |
| WO | WO/00/25672 | 5/2000 |
| WO | WO/00/48512 | 8/2000 |
| WO | WO/00/57767 | 10/2000 |
| WO | WO/00/68637 | 11/2000 |
| WO | WO/01/01845 | 1/2001 |
| WO | WO/01/06925 | 2/2001 |
| WO | WO/01/12093 | 2/2001 |
| WO | WO/01/56469 | 8/2001 |
| WO | WO/01/75465 | 10/2001 |
| WO | WO/01/87173 | 11/2001 |
| WO | WO/02/067202 | 8/2002 |
| WO | WO/02/083016 | 10/2002 |
| WO | WO/03/102614 | 12/2003 |
| WO | WO/2005/067563 | 7/2005 |
| WO | WO 2005/112836 A2 | 12/2005 |
| WO | WO/2006/081409 | 8/2006 |
| WO | WO/2006/094156 | 9/2006 |
| WO | WO/2006/136029 | 12/2006 |
| WO | WO/2007/002541 | 1/2007 |
| WO | WO/2007/005367 | 1/2007 |
| WO | WO/2007/033240 | 3/2007 |
| WO | WO 2007/047966 A2 | 4/2007 |
| WO | WO/2007/066096 | 6/2007 |
| WO | WO/2008/015605 | 2/2008 |
| WO | WO/2008/023321 | 2/2008 |
| WO | WO/2008/082661 | 7/2008 |
| WO | WO/2008/129510 | 10/2008 |

OTHER PUBLICATIONS

Greenleaf et al., "Multidimensional Cardiac Imaging," Acoustical Imaging 20:403-411 (1993).

Grimson et al., "An Automatic Registration Method for Frameless Stereotaxy, Image Guided Surgery, and Enhanced Reality Visualization," IEEE Trans Med Imaging 15:129-140 (1996).

International Search Report and Written Opinion for corresponding PCT application No. PCT/US2010/037718, date of mailing Dec. 29, 2010.

Ackerman et al., "Rapid 3D Tracking of Small RF Coils [abstract]," Proceedings of the 5th Annual Meeting of ISMRM, Montreal, Canada pp. 1131-1132 (1986).

Atalar et al., "High Resolution Intravascular MRI and MRS using a Catheter Receiver Coil," MRM 36:596-605 (1996).

Bahnson, "Strategies to Minimize the Risk of Esophageal Injury During Catheter Ablation for Atrial Fibrillation: Catheter Ablation for AF Using a Combination of RF and Cryothermy Ablation—a Practical Approach," Pacing Clin. Electrophysiol. 32:248-260 (2009).

Bhakta et al., "Principles of Electroanatomic Mapping," Indian Pacing Electrophysiol. J. 8:32-50 (2008).

Bleier et al., "Real-time Magnetic Resonance Imaging of Laser Heat Deposition in Tissue," Mag. Reson. Med. 21:132-137 (1991).

Burke et al., "Integration of Cardiac Imaging and Electrophysiology During Catheter Ablation Procedures for Atrial Fibrillation," J. Electrocardiol. 39:S188-S192 (2006).

Chen et al., "Right Atrial Focal Fibrillation: Electrophysiologic Characteristics and Radiofrequency Catheter Ablation," J. Cardiovasc. Electrophysiol. 10:328-335 (1999).

Cummings et al., "Assessment of Temperature, Proximity, and Course of the Esophagus During Radiofrequency Ablation within the Left Atrium," Circulation 112:459-464 (2005).

Dick et al., "Real Time MRI Enables Targeted Injection of Labeled Stem Cells to the Borders of Recent Porcine Myocardial Infarction Based on Functional and Tissue Characteristics," Proc. Intl. Soc. Mag. Reson. Med. 11:365 (2003).

Dick et al., "Magnetic Resonance Fluoroscopy Allows Targetd Delivery of Mesenchymal Stem Cells to Infarct Borders in Swine," Circulation 108:2899-2904 (2003).

Dumoulin et al., "Simultaneous Acquisition of Phase-Contrast Angiograms and Stationary-Tissue Images with Hadamard Encoding of Flow-induced Phase Shifts," JMRI 1:399-404 (1991).

Dumoulin et al. "Real-Time Position Monitoring of Invasive Devices Using Magnetic Resonance," Mag. Reson. Med. 29:411-415 (1993).

Ector et al., Improved Efficiency in the EP Lab with syngo DynaCT Cardiac, AXIOM Innovations 26-32 (2008).

Edelman et al., "Magnetic Resonance Imaging," N. Engl. J. Med. 328:708-716 (1993).

Elgort, "Real-Time Catheter Tracking and Adaptive Imaging for Interventional Cardiovascular MRI," Case Western Reserve University student thesis (2005).

Elgort et al., "Real-time Catheter Tracking and Adaptive Imaging," J. Magnetic Resonance Imaging 18:621-626 (2003).

Fisher et al., "Atrial Fibrillation Ablation: Reaching the Mainstream: Methodology," Pacing Clin. Electrophysiol. 29:523-537 (2006).

Guttman et al., "Imaging of Myocardial Infarction for Diagnosis and Intervention Using Real-Time Interactive MRI without ECG-Gating or Breath-Holding," Mag. Reson. Med. 52:354-361 (2004).

Hamadeh et al., "Anatomy Based Multi-modal Medical Image Registration for Computer Integrated Surgery," SPIE 2355:178-188 (1994).

Hao and Hongo, "Use of Intracardiac Echocardiography During Catheter Ablation for Atrial Fibrillation: Maximizing Safety and Efficacy," EP Lab Digest 5(4) (2005).

Hillenbrand et al., "The Bazzoka Coil: A Novel Dual-Purpose Device for Active Visualization and Reduction of Cable Currents in Electrically Conductive Endovascular Instruments," Proc. Intl. Soc. Mag. Reson. Med. 13:197 (2005).

Jais et al., "Ablation Therapy for Atrial Fibrillation (AF): Past, Present and Future," Cardiovasc. Res. 54:337-346 (2002).

Jerwzewski et al., "Development of an MRI-Compatible Catheter for Pacing the Heart: Initial In Vitro and In Vivo Results," JMRI, ISHRM 6(6):948-949 (1996).

Jolesz et al., "MR Imaging of Laser-Tissue Interactions," Radiol. 168:249-253 (1988).

Kainz, "MR Heating Tests of MR Clinical Implants," J. Magnetic Resonance Imaging 26:450-451 (2007).

Kantor et al., "In vivo 31P Nuclear Magnetic Resonance Measurements in Canine Heart Using a Catheter-Coil," Circ. Res. 55:261-266 (1984).

Karmarkar, "An Active MRI Intramyocardial Injection Catheter," Proc. Intl. Soc. Mag. Reson. Med. 11:311 (2003).

Kerr et al., "Real-time Interactive MRI on a Conventional Scanner," MRM 38:355-367 (1997).

Kumar, "MR Imaging with a Biopsy Needle," Proc. Intl. Soc. Mag. Reson. Med. 9:2148 (2001).

Lewin et al., "Needle localization in MR-guided biopsy and aspiration: effects of field strength, sequence design, and magnetic field orientation," Am. J. Roentgenol. 166:1337-1345 (1996).

Morady, "Mechanisms and Catheter Ablation Therapy of Atrial Fibrillation," Tex. Heart Inst. J. 32:199-201 (2005).

Nademanee et al., "A New Approach for Catheter Ablation of Atrial Fibrillation: Mapping of the Electrophysiologic Substrate," J. Am. Coll. Cardiol. 43:2044-2053 (2004).

Ocali et al., "Intravascular Magnetic Resonance Imaging Using a Loopless Catheter Antenna," Mag. Reson. Med. 37:112-118 (1997).

Oral et al., "A Tailored Approach to Catheter Ablation of Paroxysmal Atrial Fibrillation," Circulation 113:1824-1831 (2006).

Pfister, "Architectures for Real-Time Volume Rendering," Future Generations Computer Systems 15(1):1-9 (1999).

Pickens, "Magnetic Resonance Imaging," Handbook of Medical Imaging (Beutel, et al. eds.) 1:373-461 (2000).

Quick et al., "Endourethral MRI," Mag. Reson. Med. 45:138-146 (2001).

(56) References Cited

OTHER PUBLICATIONS

Ratnayaka et al., "Interventional cardiovascular magnetic resonance: still tantalizing," J. Cardiovasc. Mag. Reson.10:62 (2008).
Reddy et al., "Integration of Cardiac Magnetic Resonance Imaging with Three-Dimensional Electroanatomic Mapping to Guide Left Ventiruclar Catheter Manipulation: Feasibility in a Porcine Model of Healed Myocardial Infarction," J. Am. Coll. Cardiol. 44(11):2202-2213 (2004).
Schirra et al,, "A View-sharing Compressed Sensing Technique for 3D Catheter Visualization from Bi-planar Views," Proc. Intl. Soc. Mag. Reson. Med. 17:68 (2009).
Silverman et al., "Interactive MR-guided Biopsy in an Open Configuration MR Imaging System," Radiol. 197:175-181 (1995).
Susil et al., "Multifunctional Interventional Devices for MRI: A Combined Electrophysiology/MRI Catheter," Mag. Reson. Med. 47:594-600 (2002).
Swain, "New MRI, Ultrasound Techniques Could Advance Breast Cancer Treatment," Medical Device & Diagnostic Industry Online (Apr. 1, 2004).
Torres et al.,"La cartografia electroanatomica (CARTO) en la ablacion de la fibrilacion auricular," Arch. Cardiol. Mex. 76(Supp 2):196-199 (2006).
Van Den Elsen et al., "Image Fusion Using Geometrical Features," SPIE 1808:172-186 (1992).
Weiss et al., "Transmission Line for Improved RF Safety of Interventional Devices," Mag. Reson. Med. 54:182-189 (2005).
Yang et al., "New Real-time Interactive Cardiac Magnetic Resonance Imaging System Complements Echocardiology," J. Am. Coll. Cardiol., 32:2049-2056 (1998).
Biosense Webster, Inc., Carto™ XP Electroanatomical Navigation System [Brochure] (2004) (accessed at www.biosensewebster.com/products/pdf/B0037Carto_V7_Bro_Fnl.pdf).
Robin Medical, Inc., "The EndoScout® Tracking System" Robin Medical Inc. (2009) (accessed at http://www.robinmedical.com/endoscout.html).
Robin Medical, Inc., "Sensors" Robin Medical Inc. (2009) (accessed at http://www.robinmedical.com/sensors.html).
Robin Medical, Inc., EndoScout® Tracking System for MRI [Brochure] (2009) (accessed at http://www.robinmedical.com/Robin_Medical_Brochure.pdf).
Siemens USA, "Siemens Medical Solutions Revolutionizes Electrophysiology with syngo® DynaCT Cardiac Enhancement 3D Visualization of the Left Atrium, Reducing the Need for Pre-Procedural CT or MR Imaging, and Facilitating Improved Workflow," Siemens USA (2007) (accessed at http://press.siemens.us/index.php?s=43&item=94).
St. Jude Medical, Inc., "EnSite™ System," St. Jude Medical (2011) (accessed at http://www.sjmprofessional.com/Products/US/Mapping-and-Visualization/EnSite-System.aspx).
St. Jude Medical, Inc., "EnSite NavX™ Navigation & Visualization Technology," St. Jude Medical (2011) (accessed at http://www.sjmprofessional.com/Products/US/Mapping-and-Visualization/EnSite-NavX-Navigation-and-Visualization-Technology.aspx).
St. Jude Medical, Inc., "EnSite Array™ Catheter," St. Jude Medical (2011) (accessed at http://www.sjmprofessional.com/Products/Intl/Mapping-and-Visualization/EnSite-Array-Catheter.aspx).
St. Jude Medical, Inc., "EnSite Verismo™ Segmentation Tool," St. Jude Medical (2011) (accessed at http://www.sjmprofessional.com/Products/US/Mapping-and-Visualization/EnSite-Verismo-Segmentation-Tool.aspx).
St. Jude Medical, Inc., "EnSite Fusion™ Registration Module," St. Jude Medical (2011) (accessed at http://www.sjmprofessional.com/Products/US/Mapping-and-Visualization/EnSite-Fusion-Registration-Module.aspx).
St. Jude Medical, Inc., EnSite Fusion™ Registration Module Procedure Guide [Brochure] (2007) (accessed at http://www.ensitefusion.com/downloads/EnSiteFusionRegistrationModuleProcedureGuide.pdf).
Surgivision, Inc., "ClearTrace™ Cardiac Intervention System," Surgivision (2010) (accessed at http://www.surgivision.com/development).
Non-Final Office Action for U.S. Appl. No. 12/795,929, filed Jun. 8, 2010, Mail Date Nov. 26, 2012.
European Search Report Corresponding to European Patent Application No. 10 78 6663; Dated: May 6, 2015; 5 Pages.
European Search Report Corresponding to European Patent Application No. 10 78 6666; Dated: May 7, 2015; 6 Pages.
European Search Report Corresponding to European Patent Application No. 10 79 0116; Dated: May 18, 2015; 5 Pages.

\* cited by examiner

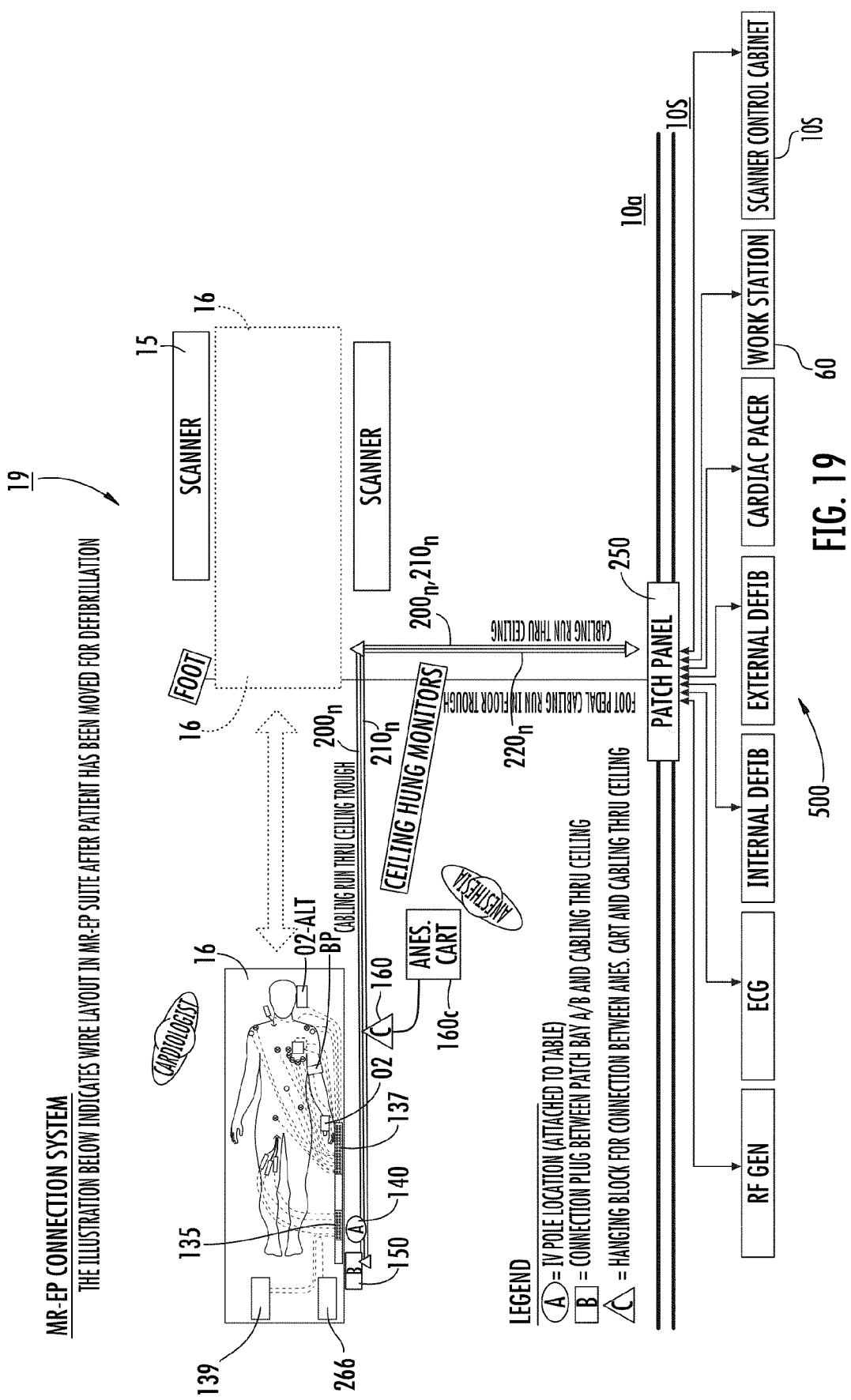

MRI-GUIDED SURGICAL SYSTEMS WITH PROXIMITY ALERTS

RELATED APPLICATIONS

This application claims the benefit of and priority to U.S. Provisional Application Ser. No. 61/185,072 filed Jun. 8, 2009, U.S. Provisional Application Ser. No. 61/187,323 filed Jun. 16, 2009, U.S. Provisional Application Ser. No. 61/219,638 filed Jun. 23, 2009, and U.S. Provisional Application Ser. No. 61/261,103 filed Nov. 13, 2009, the contents of which are hereby incorporated by reference as if recited in full herein.

FIELD OF THE INVENTION

The present invention relates to MRI-guided systems and may be particularly suitable for cardiac systems, such as cardiac EP systems for treating Atrial Fibrillation (AFIB).

BACKGROUND OF THE INVENTION

Conventional Cardiac EP (ElectroPhysiology) Systems are X-ray based systems which use electroanatomical maps. Electroanatomical maps are virtual representations of the heart showing sensed electrical activity. Examples of such systems include the Carto® electroanatomic mapping system from Biosense Webster, Inc., Diamond Bar, Calif., and the EnSite NavX® system from Endocardial Solutions Inc., St. Paul, Minn.

However, there remains a need for MRI-guided systems that can use MRI to obtain details of tissue not provided by X-ray based systems and/or to reduce patient exposure to radiation associated with the interventional (diagnostic and/or therapeutic) procedures.

SUMMARY OF EMBODIMENTS OF THE INVENTION

Embodiments of the invention are directed to systems that facilitate MRI-guided procedures. The systems include a circuit and a display in communication with the circuit. The display has a User Interface (UI). The circuit is configured to provide at least one volumetric planning map of relevant patient anatomy to the display. The UI is configured to allow a user to select at least one target treatment site and/or at least one avoid zone on the planning map. The circuit is configured to define proximity alert locations for an MRI-guided procedure associated with the selected at least one target treatment site and/or the selected at least one avoid zone.

The circuit can be configured to define proximity alert locations for the selected at least one target treatment site and the selected at least one avoid zone and define boundary limits for the at least one target treatment site for the proximity alerts.

The at least one volumetric planning map can include at least one map of the patient's heart. The UI can be configured to allow a user to use the planning map to define a plurality of avoid zones for the proximity alerts for the MRI-guided procedure, including at least two of the following: a portion of an esophagus adjacent a cardiac posterior wall, an aorta, a phernic nerve, and an atrioventricular (AV) node of the patient's heart.

The UI can be configured to allow a user to select at least one intrabody target treatment site on the at least one planning map to identify a respective proximity alert location. The proximity alert for treatment sites can be generated as a confirmation proximity alert when an intrabody device is determined to be within defined boundary limits of a respective treatment site and can be generated as a warning proximity alert when the intrabody device is determined to be outside the defined boundary limits. The warning proximity alert can have a different audible signal than the confirmation proximity alert.

The UI can be configured to carry out at least one of the following: (a) allow a user to select the boundary limits for the at least one selected site by marking locations on the planning map or by selecting dimensional spacing about a treatment site; (b) provide defined boundary limits for the at least one selected target site based on pre-defined data regarding a medical device that will be used during the MRI guided procedure to carry out a therapy or a diagnostic procedure at the at least one selected target site; or (c) provide default boundary limits that can be modified by a user for the at least one target site. The default boundary limits can be defined based on known data regarding a medical device that will be used during the MRI guided procedure to deliver a therapy to the treatment site.

The UI can be configured to allow a user to select at least one intrabody avoid zone using a list of suggested avoid zones provided by the circuit for the MRI-guided procedure. The circuit automatically electronically identifies the selected at least one avoid zone on the planning map to define one of the at least one proximity alert location.

The circuit can be configured to generate proximity alerts during the MRI guided procedure when a distal end of an intrabody medical device is proximate one of the proximity alert locations.

The pre-defined data of the medical device can include physical data regarding size, shape and position of at least one tracking coil on a distal end portion of the medical device. The at least one tracking coil is configured to connect to an MR Scanner channel.

Other embodiments are directed to MRI-guided systems that include a circuit adapted to communicate with and/or be integral with an MRI Scanner. The circuit is configured to: (a) identify at least one target intrabody treatment or diagnostic site of a patient and define boundary limits for the at least one site and/or (ii) identify at least one avoid zone of the patient; (b) define proximity alert locations for the identified at least one treatment site and the at least one avoid zone; and (c) generate at least one proximity alert during an MRI guided procedure. The at least one proximity alert is generated when a distal end portion of an intrabody device is electronically automatically determined to be at least one of the following: inside the defined boundary limits of the at least one target intrabody site, outside the defined boundary limits of the at least one intrabody target site, or proximate the at least one avoid zone.

The circuit can be configured to provide at least one volumetric planning map of relevant patient anatomy. The circuit can be communication with a display with a user interface that is configured to allow user input to define the at least one intrabody target treatment or diagnostic site using the planning map.

The user interface can be configured to carry out at least one of the following: (a) allow a user to select boundary limits for the at least one selected site by marking locations on the planning map or by selecting desired dimensional tolerances for a selected treatment or diagnostic site; (b) provide defined boundary limits for the at least one selected target site based on pre-defined data regarding a medical device that will be used during the MRI guided procedure; or (c) provide defined boundary limits as default boundary limits that can be modified by a user for the at least one target site based on predefined data regarding a medical device that will be used during the MRI guided procedure to deliver a therapy to the treatment site.

The circuit can be configured to register the at least one patient planning map to 3-D MRI imaging space prior to the MRI guided procedure, wherein the at least one planning map includes the proximity alert locations for the at least one avoid zone and the at least one diagnostic or treatment site. The circuit can be configured to identify spatial locations of the defined treatment sites and the at least one avoid zone in 3-D MRI imaging space based on the registered at least one planning map.

In some embodiments, the at least one planning map comprises at least one map of the patient's heart and the at least one planning map is used to define a plurality of avoid zones, including at least two of the following: a portion of an esophagus adjacent a cardiac posterior wall, an aorta, a phernic nerve, and an atrioventricular (AV) node of the patient's heart.

The circuit can be configured to generate warning proximity alerts when the distal end portion of the device is determined to be outside the defined boundary limits of a respective target site or proximate an avoid zone.

The circuit can be configured to generate positive proximity alerts when the distal end portion of the device is determined to be within the defined boundary limits proximate a respective target site.

In some embodiments, the intrabody device is an ablation catheter. The circuit can be configured to lock activation of the ablation electrode or electrodes on the ablation catheter or other energy or treatment when a proximity alert is generated for an avoid zone and/or when the distal end of the ablation catheter is determined to be outside boundary limits of a proximate target treatment site. In other embodiments, the device is a different therapeutic device and the circuit can block delivery or activation of the device similar to the ablation catheter discussed above.

The circuit can be configured to generate the proximity alerts based on pre-defined data of the distal end portion of the medical device, including physical data regarding size, shape and position of at least one tracking coil on a distal end portion of the medical device. The at least one tracking coil can be configured to connect to an MR Scanner channel.

Yet other embodiments are directed to MRI guided cardiac EP systems. The systems include a clinician workstation and a display with a User Interface in communication with and/or integrated into the workstation. The display can be configured to display at least one volumetric model of at least a portion of a patient's heart. The User Interface is configured to allow a user to select target ablation sites on the at least one model on the display. Boundary limits for target ablation sites can be electronically defined. The system is configured to automatically generate an audible proximity alert and/or a visual proximity alert on the display when a distal end portion of an ablation catheter is in a position that is outside the defined boundary limits of a respective target ablation site.

The User Interface can be configured to allow a user to identify avoid zones on the at least one model, and wherein the system is also configured to generate proximity alerts when a distal end portion of the ablation catheter is proximate the identified avoid zone during an MRI-guided interventional procedure.

The system can be configured to register the at least one model to 3-D MRI imaging space prior to or during an MRI-guided procedure to electronically define locations of the at least one ablation site, the associated boundary limits and the at least one avoid zone in the 3-D imaging space, and wherein the circuit automatically generates proximity alerts when a distal end portion of the ablation catheter used during the MRI-guided procedure is determined to be: outside the boundary limits of a selected ablation site, inside boundary limits of a selected ablation site, and proximate an avoid zone.

Yet other embodiments are directed to MRI guided cardiac EP systems. The systems include a clinician workstation and a display with a User Interface in communication with or integrated into the workstation. The display is configured to display at least one volumetric model of at least a portion of a patient's heart. The User Interface is configured to allow a user to select avoid zones on the at least one model on the display. The system is configured to automatically generate an audible and/or visual alert when a distal end portion of an ablation catheter is in a position that is proximate a selected avoid zone during an MRI-guided interventional procedure.

The avoid zones can include at least two of the following: a portion of an esophagus adjacent a cardiac posterior wall, an aorta, a phernic nerve, and an atrioventricular (AV) node of the patient's heart or for heart failure, normal tissue adjacent infarct tissue.

Still other embodiments are directed to methods for facilitating MRI-guided procedures. The methods include: (a) providing at least one volumetric map of relevant anatomy of a patient; (b) identifying at least one avoid zone on the at least one volumetric map, the avoid zone associated with sensitive tissue that resides along a tortuous intrabody access path to a target treatment or diagnostic site or that resides proximate a target treatment or diagnostic site; then (c) registering the volumetric map with the identified at least one avoid zone to 3-D MRI imaging space; (d) tracking location of a distal end portion of an intrabody medical device during an MRI guided procedure to determine a location of the device in the 3-D MRI imaging space; and (e) electronically generating a proximity alert when the distal end portion of the medical device is determined to be proximate the at least one identified avoid zone.

The method may also include, before the registering step, identifying at least one target treatment site on the at least one volumetric map; and electronically associating boundary limits for the at least one identified treatment site, and wherein, after the registering step. The method can also include electronically generating a confirmation proximity alert when the distal end portion of the medical device is determined to be proximate an identified treatment site; and electronically generating a warning proximity alert when the distal end portion of the medical device is determined to be outside associated boundary limits of a respective treatment site. The confirmation proximity alert has a different visual indicator and/or different audible output that the warning proximity alert. The electronically generated proximity alert for the at least one identified avoid zone is a warning proximity alert.

Yet other embodiments are directed to methods for carrying out an MRI-guided therapy to treat cardiac disease or disorders. The methods include: (a) displaying at least one volumetric model of at least a portion of a heart of a patient; (b) allowing a user to mark and/or select target ablation sites on the displayed rendering; (c) electronically defining boundary limits for the target ablation sites in response to the marking step; then (d) electronically monitoring a position of a distal end portion of an ablation catheter in 3-D MRI imaging space; and (e) electronically generating an alert when the position of the distal end portion of the ablation catheter is determined to be at least one of: (i) within the defined boundary limits of a respective selected target ablation site and/or (ii) outside the defined boundary limits of a respective selected target ablation site during an MRI-guided therapy.

The method can also include allowing a user to mark and/or select at least one avoid zone on the at least one volumetric model; and electronically generating an alert when the position of the distal end portion of the ablation catheter or a distal end portion of a transseptal needle is determined to be proximate the at least one avoid zone during the MRI-guided therapy.

The method can include registering the volumetric model to the 3-D imaging space before the monitoring and generating an alert steps.

The method may optionally include electronically associating preset scan planes for the selected target ablation sites using the at least one model; and obtaining near real time MR image data using the preset scan planes during the MRI-guided procedure.

The step of allowing a user to mark can be carried out to allow a user to generate a drag catheter lesion formation pattern on the map.

Still other embodiments are directed to a computer program product for facilitating an MRI-guided interventional therapy of a patient. The computer program product includes a non-transitory computer readable storage medium having computer readable program code embodied in the medium. The computer-readable program code includes: (a) computer readable program code that renders a volumetric map of at least a portion of a patient's target anatomy; (b) computer readable program code that defines at least one avoid zone using the volumetric map; (c) computer readable program code that defines at least one target treatment site using the volumetric map; (d) computer readable program code that registers the map with the defined at least one avoid zone and at least one target treatment site in three dimensional MRI imaging space; and (e) and computer readable program code that generates a proximity alert when an intrabody device is proximate the at least one target treatment site and the at least one avoid zone.

The product can also include computer readable program code that accepts user input to identify the at least one defined target treatment site on the volumetric map and computer readable program code that defines boundary limits for a respective treatment site in response to a user's identification of the selected at least one target treatment site.

The volumetric map can include a map of a patient's heart and the intrabody device is an ablation catheter with tracking coils that connect to channels of an MRI Scanner. The computer readable program code that generates the proximity alert includes computer readable program code that is able to calculate a shape and position of the distal end of the device based on known physical data of the intrabody device and tracking signal data.

The computer program product can include computer readable program code that defines pre-set scan planes for the at least one avoid zone and/or the at least one target treatment site in response to a user's identification of the at least one avoid zone and/or the at least one target treatment site on the map.

The computer readable program code that identifies at least one treatment site comprises computer readable program code that a allows a user to use a GUI in communication with a display to generate a drag catheter lesion formation pattern on the map.

The computer readable program code that generates the proximity alert is configured to generate an audio and/or visual alert when a distal end portion of the ablation catheter is in a location that will generate a lesion that is outside the defined boundary limits.

Yet other embodiments are directed to MRI guided cardiac interventional systems. The systems include: (a) a display; (b) a processor in communication with the display and adapted to communicate with an MRI scanner; (c) electronic memory coupled to the processor; and (d) computer program code residing in the memory that is executable by the processor for:
  obtaining MR image data of a heart of a subject;
  rendering at least one 3-D map of at least a portion of the heart of the subject;
  displaying a graphical user interface (GUI) containing the at least one map within the display, wherein the GUI allows a user to select at least one target ablation site and at least one avoid zone on the at least one map; and
  generating at least one proximity alert based on the selected at least one target ablation site and/or at least one avoid zone during an MRI guided procedure.

The systems can include computer program code residing in the memory that is executable by the processor for: defining pre-set scan planes for the selected at least one target ablation site; and defining boundary limits for the at least one selected target ablation site.

The computer program code configured to generate a proximity alert is configured to generate the proximity alert if a distal end of an ablation catheter is at a location that will generate a lesion that is outside the defined boundary limits for a respective target ablation site.

Some embodiments are directed to MRI-guided cardiac interventional systems that include a circuit adapted to communicate with an MRI Scanner. The circuit is configured to define target therapeutic delivery boundary limits for a defined target therapy delivery site and generate an alert during an interventional procedure when a delivery location is determined to be inside and/or outside the defined boundary limits.

Still other embodiments are directed to MRI-guided cardiac interventional systems that include a circuit adapted to communicate with an MRI Scanner. The circuit is configured to define at least one patient avoid zone associated with target anatomical structure proximate a delivery site or associated with a tortuous delivery path and generate an alert during an MRI-guided interventional procedure when an intrabody device is determined to be proximate the avoid zone.

Embodiments of the invention are particularly suitable for MRI-guided cardiac procedures including cardiac EP procedures for ablating tissue to treat arrythmias such as AFIB or to treat heart failure.

The systems may also be suitable for delivering a therapeutic agent or carrying out another treatment or diagnostic evaluation for any intrabody location, including, for example, the brain, heart, gastrointestinal system, genourinary system, spine (central canal, the subarachnoid space or other region), vasculature or other intrabody location.

It is noted that any one or more aspects or features described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 19 is a schematic illustration of an exemplary MRI cardiac interventional suite according to some embodiments of the present invention.

DETAILED DESCRIPTION OF EMBODIMENTS OF THE INVENTION

Figure 1:
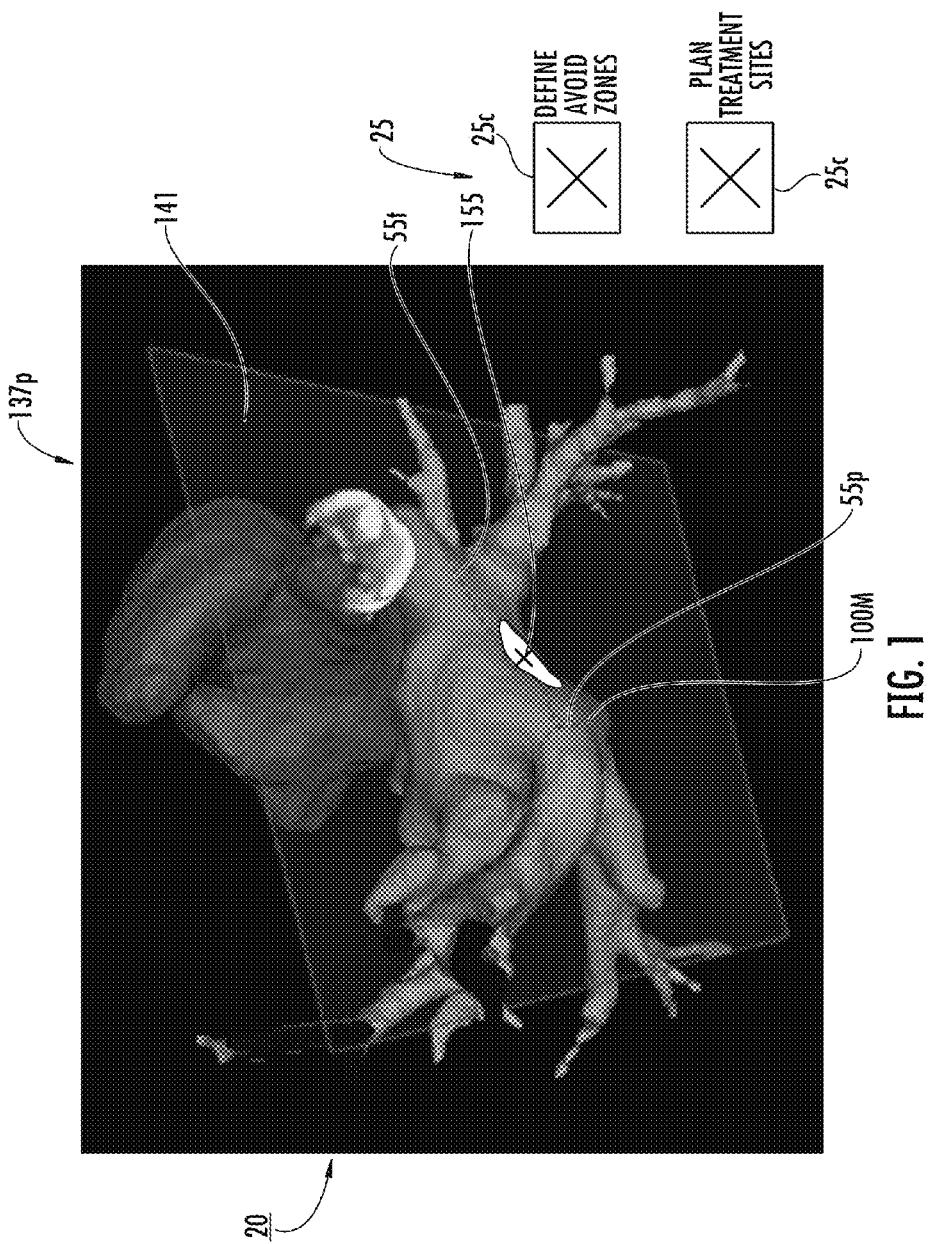
FIG. 1 is a schematic illustration of a display with a User Interface for defining proximity alert locations associated with avoid zones and/or target treatment sites using a patient anatomical model for MRI-guided procedures according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "circuit" refers to an entirely software embodiment or an embodiment combining software and hardware aspects, features and/or components (including, for example, at least one processor and software associated therewith embedded therein and/or executable by and/or one or more Application Specific Integrated Circuits (ASICs), for programmatically directing and/or performing certain described actions or method steps). The circuit can reside in one location or multiple locations, it may be integrated into one component or may be distributed, e.g., it may reside entirely in an MR Scanner control cabinet, partially in the MR Scanner control cabinet, totally in a separate component or system such as a clinician workstation but communicate with MR Scanner electronics and/or in an interface therebetween, in a remote processor and combinations thereof.

The term "pre-set scan plane" refers to scan planes electronically (programmatically) defined for subsequent use by an MRI Scanner as being associated with a location of relevant anatomical tissue of a patient during a MRI guided therapeutic or diagnostic procedure. The pre-set scan planes can be defined based on one or more volumetric models or maps of patient anatomical structure that is subsequently registered or aligned in 3-D imaging space and can be used to acquire near real-time MR image data of patient tissue.

The term "map" is used interchangeably with the word "model" and refers to a rendered volumetric visualization or image of target anatomical structure of a patient. The map or model can take on any suitable form, including an electrocanatomical map, MRI images, computer segmented model and the like and combinations of same. The term "tissue characterization map" refers to a rendered visualization or image of one or more selected parameters, conditions, or behaviors of cardiac tissue using MR image data, e.g., the tissue characterization map is a rendered partial or global (volumetric) anatomical map that shows at least one defined tissue characteristic of the heart in a manner that illustrates relative degrees or measures of that tissue characteristic(s), typically in different colors, opacities and/or intensities. Notably, the tissue characterization map is to be contrasted with an electroanatomical tissue map which is based on sensed electrical activity of different regions of the heart rather than on MR image data. The planning map and/or subsequent visualizations can use one or both types of volumetric maps. Thus, the planning map and/or visualizations can use one or both types of volumetric tissue maps, shown separately, overlaid on each other and/or integrated (e.g., superimposed) as a composite map. In some embodiments, tissue data from an electroanatomical map and/or the tissue characteristic map can be selectively faded or turned on and off with respect to a pre-acquired map/model of the patient's anatomical structure (e.g., Left Atrium). The terms "fade" and "faded" refer to making the so-called feature less visually dominant in a visualization and/or planning map by dimming the intensity, color and/or opacity relative to other features in the visualization.

The actual visualization can be shown on a screen or display so that the map or anatomical structure is in a flat 2-D and/or in 2-D what appears to be 3-D volumetric images with data representing features or electrical output with different visual characteristics such as with differing intensity, opacity, color, texture and the like. A 4-D map can either illustrate a 3-D heart with movement (e.g., a beating heart and/or a heart with blood flow) or show additional information over a 3-D anatomic model of the contours of the heart or portions thereof.

The term "4-D multiparametric visualization" (4-DMP) means a 4-D visualization (e.g., a 3-D image of a beating heart) with functional spatially encoded or correlated information shown on the visualization. The 4-DMP visualization can be provided with fMRI data and/or one or more tools used to provide the spatially correlated functional data (e.g., electrical, DHE) data of the heart based on a 3-D model. Again, the 3-D, 4-D and/or 4-DMP visualizations are not merely an MRI image or MRI images of the patient but are rendered visualizations that can combine multiple sources of data to provide a visualization of spatially encoded function with anatomical shape. Thus, the visualizations can comprise a rendered model of the patient's target anatomy with a rendered visualization of at least one medical device in an intrabody location with respect to the model and along with near RT MRI image data of the anatomical structure. The figures may include prophetic examples of screen shots of visualizations and the like and do not necessarily represent actual screen shots of a display.

The term "close-up" means that the associated image is shown enlarged relative to a global image or map view to show local tissue. The term "high-resolution" means that the image data is obtained with higher resolution than normal image data (usually requiring longer scan times and/or using an internal antenna to increase SNR). For example, the local tissue ablation views may be shown in higher resolution than real-time MRI images in the navigation view. The term en face refers to a view through a tissue wall (e.g., myocardial wall) and parallel (or tangent) to the surface.

The term "programmatically" means that the operation or step can be directed and/or carried out by a digital signal processor, computer program code and/or an Application Specific Integrated Circuit (ASIC). Similarly, the term "electronically" means that the step or operation can be carried out in an automated manner using electronic components rather than manually or using merely mental steps.

The term "target ablation path" describes a desired lesion pattern that is selected to create a desired electrical isolation in the cardiac tissue to treat the at-risk pathology/condition (e.g., atrial fibrillation). The target ablation path is not required to be followed in any particular direction or order. The path may include one or more continuous lesions and/or several non-continuous or non-contiguous lesions. The lesions may be linear (whether straight or with a curvature such as circular or curvilinear). In any one interventional procedure, the physician can define one or more target paths to create the desired pattern/isolation. According to some embodiments, the target ablation path can be used to electronically define physical limits associated with the acceptable maximum boundary limits (e.g., width, perimeter and the like) of a site and/or the target ablation path.

The descriptors "positive" or "confirmation" used with "proximity alert" are used interchangeably to denote that, in some embodiments, the systems can be configured to generate different types of proximity alerts and the positive or confirmation proximity alert is generated as an audible and/or visual alert that can be used when an intrabody medical device is approaching or is in a correct location. In contrast, the term "warning proximity alert" refers to a proximity alert that can be generated as an audible and/or visual alert when an intrabody medical device is in an incorrect position, such as outside boundary limits of a target treatment or diagnostic site or proximate an avoid zone. Further, different audible and/or visual warning alerts can be used to distinguish the warning alerts from the confirmation alerts to provide user feedback that indicates whether the device is outside boundary limits or proximate an avoid zone or in a proper location.

At least a portion of an intrabody medical device can be tracked and its position electronically identified in 3-D MR imaging space (e.g., X, Y, Z coordinates). Various location tracking means for the tool and/or registration means for the catheter to the imaging space can be employed. For example, the intrabody device can include fiducial markers or receive antennas combinations of same. The term "fiducial marker" refers to a marker that can be identified using electronic image recognition, electronic interrogation of MRI image data, or three-dimensional electrical signals to define a position and/or find the feature or component in 3-D space. The fiducial marker can be provided in any suitable manner, such as, but not limited to a geometric shape of a portion of the tool, a component on or in the tool, a coating or fluid-filled coating (or combinations of different types of fiducial markers) that makes the fiducial marker(s) MRI-visible that are active or passive (e.g., if passive, the marker does not provide MR signal) with sufficient intensity for identifying location and/or orientation information for the tool and/or components thereof in 3-D space. As will be discussed further below, in particular embodiments, the device comprises at least one tracking coil electrically connected to a respective channel of the MRI Scanner that generate signals that are detected (received) by the MR Scanner and used to identify respective locations of the coils in a 3-D coordinate system of the imaging space, and hence the device with such tracking coils, in the 3-D image space.

The terms "MRI or MR Scanner" are used interchangeably to refer to a Magnetic Resonance Imaging system and includes the magnet, the operating components, e.g., RF amplifier, gradient amplifiers and operational circuitry including, for example, processors or ASICs (the latter of which may be held in a control cabinet) that direct the pulse sequences, select the scan planes and obtain MR data.

The term "RF safe" means that the catheter and any conductive lead is configured to operate safely when exposed to RF signals, particularly RF signals associated with MRI systems, without inducing unplanned current that inadvertently unduly heats local tissue or interferes with the planned therapy. The term "MRI visible" means that the device is visible, directly or indirectly, in an MRI image. The visibility may be indicated by the increased SNR of the MRI signal proximate the device. The device can act as an MRI receive antenna to collect signal from local tissue and/or the device actually generates MRI signal itself, such as via suitable medical grade hydro-based coatings, fluid (e.g., aqueous fluid) filled channels or lumens. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T, typically above 1.0 T, and more typically between about 1.5 T and 10 T. Embodiments of the invention may be particularly suitable for 1.5 T and/or 3.0 T systems.

The term "tortuous" refers to a curvilinear pathway in the body, typically associated with a natural lumen such as vasculature. The term "dynamic visualizations" refers to a series of visualizations that show the movement of the device(s) in the body and can show a beating heart or movement based on respiratory cycle and the like.

The term "pre-acquired" means that the data used to generate the model or map of the actual patient anatomy can be obtained prior to the start of an active therapeutic or diagnostic procedure and can include immediately prior to but during the same MRI session or at an earlier time than the procedure (typically days or weeks before).

Embodiments of the present invention can be configured to guide and/or place intrabody diagnostic and/or interventional devices in an MRI environment (e.g., interventional medical suite) to any desired internal region of interest of a subject, typically via a natural lumen and/or tortuous path so that the intrabody devices can take on different non-linear configurations/shapes as it moves into position through a target pathway (which may be a natural lumen or cavity). The subjects can be animal and/or human subjects.

Some embodiments of the invention provide systems that can be used to ablate tissue for treating arrhythmias such as atrial fibrillation, to repair or replace cardiac valves, repair, flush or clean vasculature and/or place stents, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). The cardiac procedures can be carried out from an inside of the heart or from an outside of the heart. Thus, the planning map 137$p$ can be an electroanatomical map, a tissue characterization map, an MRI image or combinations of same. Typically, for cardiac procedures, the map is rendered to represent portions or regions of the heart, such as the left atrium and any adjacent vasculature of interest (e.g., the branching of the pulmonary veins), the ventricles and the like. The cardiac procedures may be directed to treating cardiac disorders such as arrhythmias or heart failure (e.g., congestive heart failure, reduced heart function, and the like).

Other embodiments provide systems suitable for delivering a therapeutic agent or carrying out another treatment or diagnostic evaluation for any intrabody location, including, for example, the brain, gastrointestinal system, genourinary system, spine (central canal, the subarachnoid space or other region), vasculature or other intrabody locations. Additional discussion of exemplary target regions can be found at the end of this document.

Generally stated, advantageously, the systems can be configured so that the surgical space is the (MRI) imaging space and the tracking is performed in the imaging space so that there is no requirement to employ a discrete tracking system that must then be registered to the imaging space. In some embodiments, the tracking is carried out in the same 3-D imaging space but the flexible intrabody medical device is tracked independent of the imaging scan planes used to obtain the MR image data for generating images of local anatomy and is shown as a physical representation in the visualization. The systems can be configured to work with robotic systems or non-robotic surgical systems.

The term "near real time" refers to both low latency and high frame rate. Latency is generally measured as the time from when an event occurs to display of the event (total processing time). For tracking, the frame rate can range from between about 100 fps (frames per second) to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. For lesion imaging, a new image can be generated about every 1-7 s, depending on the sequence used. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., flexible catheter using the tracking coil data) and the near RT MR image(s) is generated.

In some embodiments, MR image data is obtained during an active treatment such as during an ablation, delivery of a drug or other material, valve repair or replacement, lining repair, and the like, and the resultant visualization(s) with the flexible intrabody device used for this treatment (e.g., catheter, needle and the like) along with one or more near RT MR images of local anatomy is substantially continuously generated.

The term "intrabody device" is used broadly to refer to any diagnostic or therapeutic medical device including, for example, catheters, needles (e.g., injection, suture, and biopsy), forceps (miniature), knives or other cutting members, ablation (cryo, ultrasound, RF with single or multiple ablation (array) electrodes) or stimulation probes, injection or other fluid delivery cannulas, mapping or optical probes or catheters, sheaths, guidewires, fiberscopes, dilators, scissors, implant material delivery cannulas or barrels, and the like, typically having a flexible body and/or having a size that is typically between about 5 French to about 12 French, but other sizes may be appropriate. To be clear, while detailed drawings of exemplary flexible devices 80 are shown for tracking coils for transseptal needles (septal puncture kit components) and mapping and/or ablation catheters for cardiac use, embodiments of the invention are not intended to be limited to these devices nor to cardiac use. Thus, in addition to the devices noted above, the devices can be implemented as injection catheters or diagnostic biopsy needles and the like for any target anatomical location in the body. See, e.g., U.S. patent application Ser. No. 10/769,994 (intramyocardial injection needle), U.S. Pat. No. 7,236,816 (biopsy needle), and U.S. Pat. No. 6,606,513 (transseptal needle), the contents of which are hereby incorporated by reference as if recited in full herein. Examples of a loop catheter, mapping catheter, (deformable) ablation catheter, biopsy catheter and injection needle catheter. The loop catheter and mapping catheter includes both tracking coils 82c and sensing electrodes.

Figure 2:
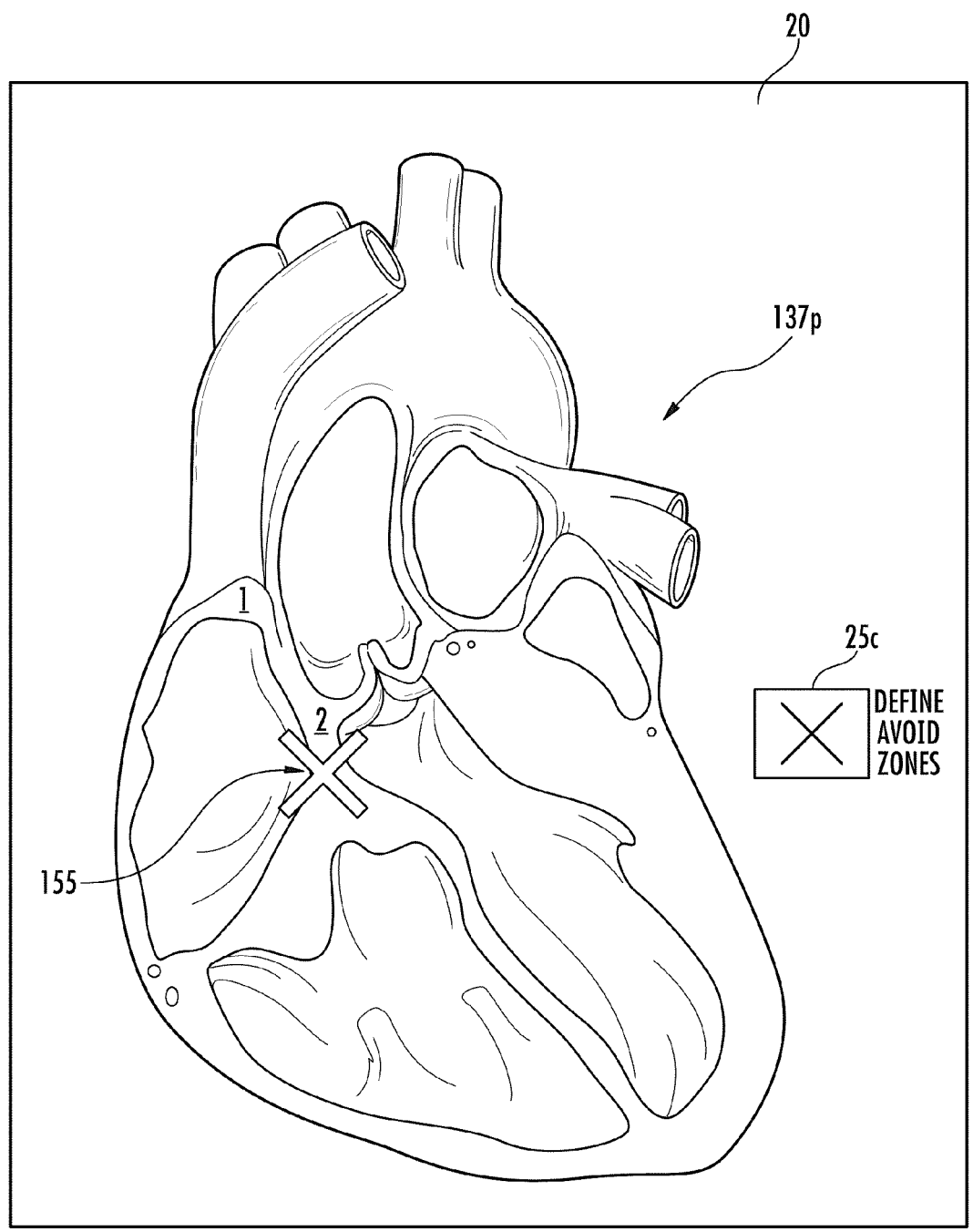
FIG. 2 is a schematic illustration of a display with a User Interface for defining avoid zones (and/or target treatment sites) using a patient anatomical model for MRI guided procedures according to embodiments of the present invention.

FIG. 1 is an example of a display 20 with a User Interface (UI) 25 with at least one UI control 25c and a volumetric planning model 137p of an exemplary target anatomical structure of a patient (e.g., it is patient-specific and is shown here as the patient's heart). The planning model 137p can be rendered using any patient-specific data in a volumetric map 100M, including, for example, an electroanatomical map/model, a tissue characteristic map/model or combinations of same. The planning model or map 137p can comprise a global model or a series of segmented or otherwise apportioned models of portions of relevant anatomy, e.g., the left atrium and right atrium (and/or pulmonary ventricles, pulmonary vein ostia, esophagus, aorta, fossa ovalis, and the like) may be shown on separate maps and/or on a global planning map. FIG. 2 illustrates a partial cutaway version of a planning map or model 137p.

The planning model 137p can accept user input via a user interface (UI) 25 with at least one UI control 25c to identify, select, define and/or "mark" at least one avoid zone 155 and/or at least one target treatment site 55t using (e.g., marked on) the planning model 137p. The UI control 25c can include a touch screen input, or other user selectable input that can be activated such as when in a planning mode, e.g., turned "on" and/or "off". Also, to facilitate selection of an avoid zone 155 and/or treatment site 55t, electroanatomical and/or tissue characteristic data can be turned "on" or "off" or faded on the model 137p. An avoid zone 155 is typically associated with susceptible or sensitive areas that should be avoided during insertion of a medical device along an intrabody path and/or at the target end location (e.g., the aorta during a transseptal entry) or certain regions of the anatomical structure that should not be treated (e.g., ablated) during active treatment (e.g., ablation). As shown, in FIG. 1, the avoid zone 155 is associated with a posterior wall of the left atrium (where the esophagus touches the posterior wall). If shown in the patient planning model 137p, the esophagus would be a long tube rising above the posterior wall of the left atrium just above the viewer 141 (panel). As shown in FIG. 2, the atrioventricular (AV) node of the patient's heart is identified as an avoid zone 155.

Figure 3:
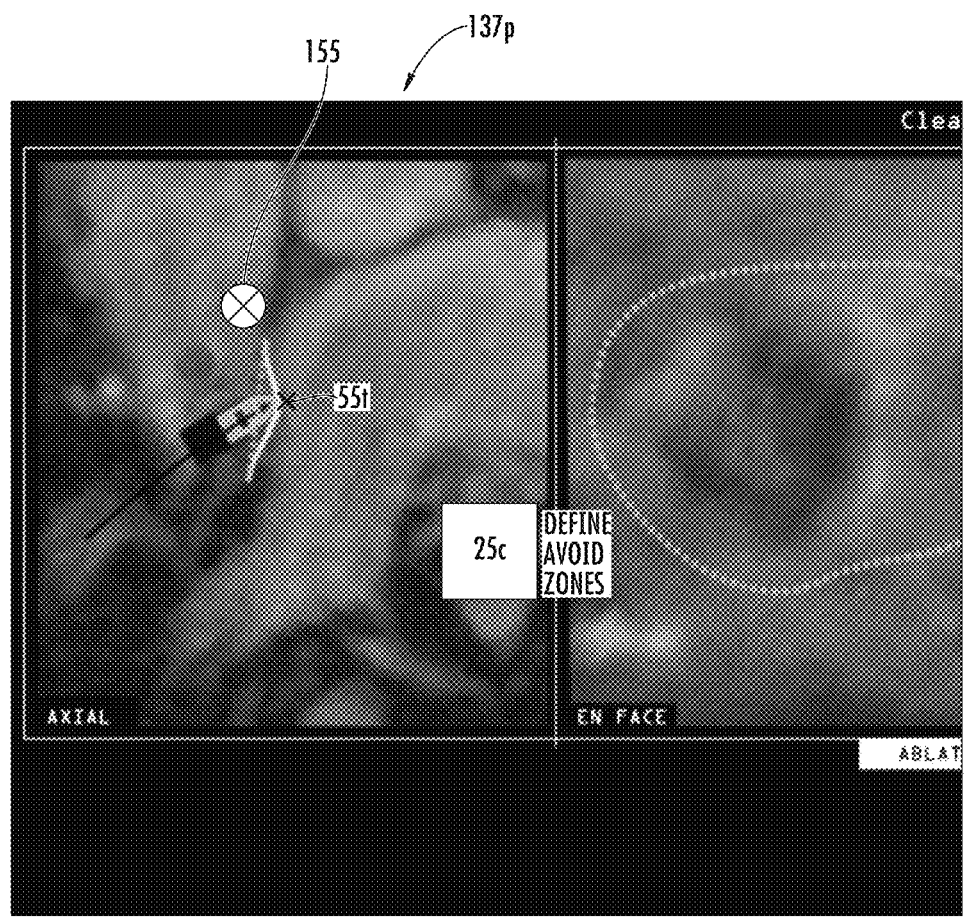
FIG. 3 is a display with a User Interface for defining avoid zones and/or target treatment sites according to embodiments of the present invention.

As shown in FIG. 3, the map 137p can be used to mark the aorta as the avoid zone 155 and the target site 55t can be the fossa ovalis, which may be suitable for certain cardiac procedures carried out via a tortuous path using a transseptal needle to place an access port as is well known.

In some embodiments, the planning map(s) 137p can be used to indicate a number of avoid zones 155, such as, for example, a portion of an esophagus adjacent a cardiac posterior wall, an aorta, a phernic nerve, and an atrioventricular (AV) node of the patient's heart. It will be appreciated that other target anatomical structures can have other sensitive areas that may be identified as an avoid zone 155 for an MRI guided procedure.

The planning map 137p with the marked or selected avoid zones 155 can be electronically registered to 3-D MRI image space prior to or at the start of a procedure. During an MRI-guided procedure, the circuit 60c (FIG. 9) can automatically generate proximity alerts 90 (FIG. 6) when one or more tracked intrabody devices 80 (FIGS. 8-10) is at a location that is proximate a defined avoid zone(s) 155. The proximity alert 90 can be an audible and/or visual warning proximity alert. The alert 90 can be shown on the navigation view of the display (and output via speakers associated with the display) or may be provided by an external audiovisual alert provided to the clinician (physician) in the MRI suite.

FIG. 1 also illustrates that the display can have a UI control 25c for a Plan Treatment (e.g., Ablation path 55p) input. This input allows a user/physician to select one or more target sites 55t (FIG. 1) for active treatment or diagnosis. As will be discussed further below, boundary limits 55l (FIG. 5) for a respective target site 55*t* can also be defined. A proximity alert 90 can be generated when a known intrabody device is within the boundary limits 55*l* proximate a selected treatment site 55*t*. A proximity alert 90 may also be generated when the known intrabody device is approaching or proximate a selected treatment site but outside the defined boundary limits 55*l*. For example, the pitch of an audible tone or some parameter of a displayed indicator may change to indicate the distance between the tip of the intrabody device and a target.

The avoid zone proximity (warning) alert 90 can be generated using the identified zone 155 on the planning map 137*p* (registered to 3-D MRI imaging space), the tracked location of the intrabody device in 3-D MRI imaging space, and known physical data regarding the form and/or features of the intrabody device (e.g., distance of the tip from the tracking coil(s)).

The treatment site alerts 90 (positive proximity alert or warning proximity alert, where used) can be generated based on the identified treatment site 55*t* on the planning map 137*p*, the defined associated boundary limits 55*l*, the tracked location of the intrabody device in 3-D MRI imaging space, and known physical data regarding the form and/or features of the intrabody device (e.g., distance of the tip from the tracking coil(s)).

More than one intrabody device can be tracked in the body during the MRI-guided procedure and the alert(s) 90 can be generated whenever any such device is in an avoid zone or other proximity alert location. For example, the alters may be configured to "focus" on the location or motion of one particular device or a visual alert may be assigned to one device while an audible alert may be assigned to another device or different sets of visual and audible alerts can be associated with each respective tracked device.

As will be discussed further below, the system can electronically associate pre-set scan planes for a respective selected treatment site 55*t* for use by an MR Scanner during the MRI-guided procedure. That is, the model 137*p* can be used to place relevant imaging slices on tissue having a certain spatial relationship to a feature (e.g., tip) of a known device 80 and those imaging slices may have certain pre-defined orientations for most advantageous viewing of the tissue or lesions within.

In some embodiments, in a plan treatment site mode, the Plan Treatment UI control 25*c* can allow a clinician/physician to select a desired ablation path that is intended to electrically isolate one or more regions of interest of cardiac tissue. As discussed above, the target ablation path 55*p* can be one continuous path or several discontinuous paths in a region of interest (ROI).

The planning model 137*p* with both or either one of the avoid zone input mode and the plan treatment site input mode may be particularly suitable for use during a pre-procedure planning stage of an interventional procedure or at an evaluation stage prior to conclusion of a procedure.

In some embodiments, the planning map 137*p* is "tagged", meaning electronically associated/loaded with the selected treatment sites 55*t* and/or the avoid zones 155, such that the proximity alert sites/zones are electronically locked to the planning map 137*p* prior to the interventional surgery. The planning map 137*p* is then typically registered to 3-D MRI imaging (coordinate) space (FIG. 7) prior to start of an MRI-guided interventional procedure which places the marked sites 55*t* and avoid zones 155 in the correct location in the 3-D MRI imaging space.

The UI typically includes multiple GUI controls 25*c* that can include a touch screen and/or mouse or other input control to allow a physician to select a region of interest in the map 137*p* by placing a cursor or by touching the screen at a region of interest. This can cause the system to define a corresponding avoid zone 155, define a target treatment site 55*t*, calculate boundary limits 55*l* (FIG. 5) (e.g., maximum acceptable boundary positions for an ablation location), and optionally electronically define preset scan planes 141 (FIG. 1) for use during an interventional procedure. In other embodiments, the system can be configured to provide a list and/or overlay of suggested avoid zones 155 for a particular medical procedure or for target anatomical structure for treatment (and/or the access path used to reach this structure). A user can select one or more of the suggested avoid zones 155 and the system can automatically virtually place these zones on the planning map 137*p* (using fiducial markers or anatomical markers) and the like. In some embodiments, the system can show a proposed avoid zone on the planning map 137*p* and allow a user to use a UI control 25*c* to move the location or adjust the size or shape of the suggested avoid zone 155 on the planning map 137*p* which may vary patient to patient as well as procedure to procedure. Once in the position, size and/or shape desired, a user may optionally affirmatively lock the avoid zone to the planning map 137*p*. A lock icon or other UI control 25*c* may be used for facilitating the avoid zone selection. In other embodiments, once the select avoid zone input is deselected, the avoid zones can be automatically locked.

In some embodiments, one or more scan plane identifier points, such as a set of points, can be virtually (automatically and/or manually) be placed on the planning map 137*p* and can be used to define relevant associated scan plane(s) 141. In some embodiments, one point/treatment site 55*t* can be placed or indicated on the planning map 137*p* by a user and the system 10 can automatically suggest one or more planes that cover this site 55*t*, and may electronically evaluate local anatomical contour to do so. A clinician may mark fiducials to facilitate the scan plane selection and/or the circuit may be configured to electronically identify anatomical fiducials to identify a position on the model and/or select suggested scan planes associated with a target site that can be used as the actual pre-set scan plane 141 or may facilitate identification or selection of an appropriate scan plane or maybe established as the pre-set scan plane(s) 141.

In other embodiments, a user can define the relevant scan planes for one or more sites 137*p* by affirmatively indicating the desired scan plane(s) using a UI control (e.g., GUI), In some embodiments, a user can virtually mark two or more points that can be used by the circuit to automatically define the pre-set scan planes 141 used to obtain relevant image slices. The automatically selected/defined pre-set scan planes 141 can be shown visually on/through the model 137*p*. A user may adjust the automatically selected scan planes 141 if desired. The UI may be configured to allow the user to affirmatively "lock" a scan plane(s) 141 for each treatment site 55*t* (and/or avoid zone 155) to electronically associate them with the planning model 137*p* for future use by an MR Scanner 10S.

In certain embodiments, the planning map 137*p* is used to identify at least one avoid zone 155 and/or relevant target treatment/diagnostic sites 55*t* (and optionally associated scan planes 141 shown as one projected scan plane in FIG. 1) in a pre-surgical planning procedure before the actual MRI-guided surgery. As noted above, the at least one avoid zone 155 and/or at least one target treatment site 55*t* can be selected without requiring that the planning map 137*p* be registered to a 3-D (e.g., X, Y, Z) coordinate system associated with MRI imaging space. Thus, the system 10 can be configured to electronically automatically or manually (such as via a clinician using the display) register the planning map 137*p* to the 3-D MRI imaging space and electronically identify proximity alert locations associated with one or more previously identified avoid zones 155 and/or one or more previously identified target treatment sites 55t.

Figure 7:
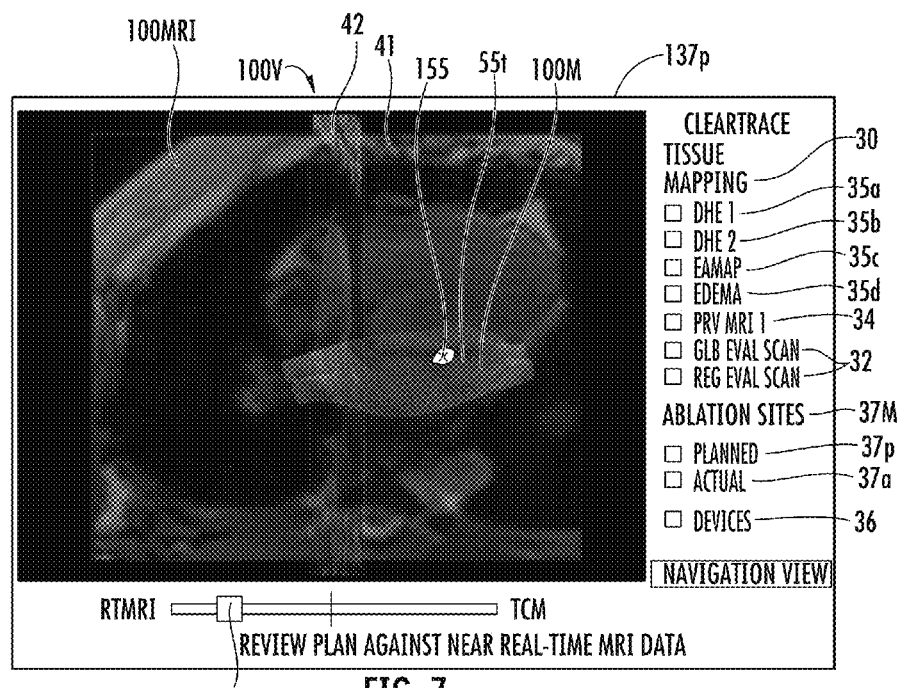
FIG. 7 is a schematic of a display with a visualization showing a rendered patient model with an avoid zone and/or treatment site registered to 3-D MRI image space according to embodiments of the present invention.

As also shown in FIG. 7, in some embodiments, the map 137p can be shown with orthogonal or oblique viewing planes or panels 41, 42 that can allow a user to rotate the map during the planning procedure and/or during the MRI-guided procedure.

Figure 4:
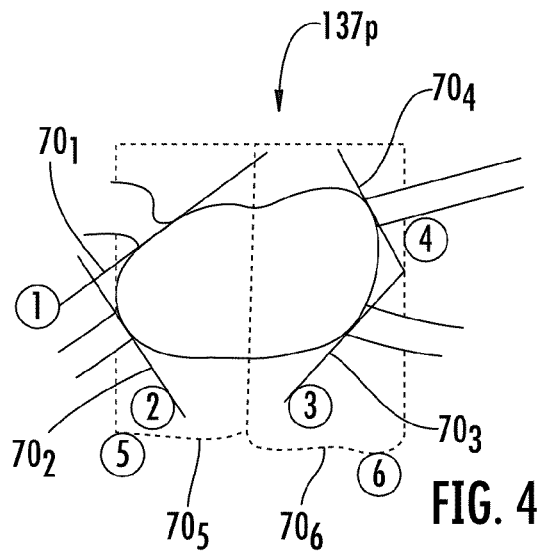
FIG. 4 is a schematic illustration of a non-limiting example of an exemplary number of different scan planes that are associated with a region of interest of a heart of a patient that can be used to obtain MR image data relevant to one or more target ablation paths during an interventional procedure according to embodiments of the present invention.
Figure 5:
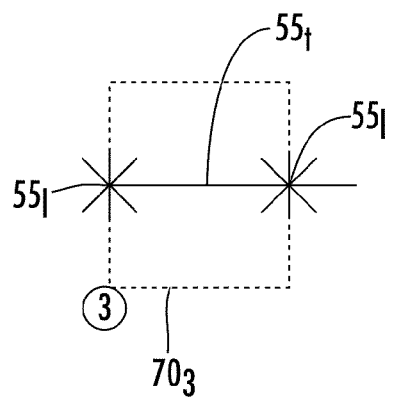
FIG. 5 is a schematic illustration of auto-defined boundary limits according to embodiments of the present invention.

FIG. 4 illustrates that the system can use the map 137p to define a plurality of different scan planes $70_1$-$70_n$, shown as with at least six (6) scan planes, one or more of which can be automatically electronically associated with a respective target treatment site(s) 55t, such as an ablation path 55p selected in FIG. 1. The six scan planes shown are merely an example of a number of different scan planes that may be used. In practice, more or less scan planes may be used for a particular path or ROI (portion) of a heart. Any scan plane can be temporarily disabled to allow faster update of the remaining scan planes. FIG. 5 illustrates one ablation path 55p associated with scan plane 3 ($70_3$).

The system 10 can automatically calculate and set boundary limits 55l on boundaries for a target ablation path 55p (e.g., a catheter drag path). In operation, if, for example, a distal end portion of an intrabody device (e.g., ablation catheter) is determined to be out of position, such as outside the defined boundary limits 55l of an associated scan plane of a respective defined treatment site 55t such that the distal end portion of the device is not visible in that scan plane, an audible or visual proximity alert 90 can be generated.

Thus, embodiments of the invention are directed to User Interfaces (UI) for clinical workstations that facilitate control of scan planes used to obtain relevant MR image data for efficient workflow and/or automation of image generation during the interventional procedure. Embodiments of the invention can also or alternatively provide near real time alerts regarding deviation from a planned treatment path during an interventional procedure.

The boundary limits 55l can be determined based on the scan plane. For example, a proposed ablation drag path 55p can be plotted on the 3D map 137p of the region of interest (ROI), such as a left atrium (LA). The system can then programmatically determine the scan planes that fall within the proposed path. The auto-limits on the boundaries of the ablation path 55p (e.g., catheter drag path) are then set based on the particular scan plane: X mm/cm of the path fall in scan plane 1; Y mm/cm of the path fall in scan plane 2; etc. These dimensions can be used to determine the boundary limits 55l. If the physician exceeds a boundary limit 55l on a particular scan plane, the system can be configured so that the Scanner will pull up the next scan plane automatically based on the location of the tip (or distal end portion) of the intrabody device, e.g., ablation catheter.

In other embodiments, the boundary limits 55l can be defined based on a predetermined distance outside the boundary limits of the selected target path, e.g., X mm from a known coordinate position of the target site 55t or path 55p. In some embodiments, a default boundary limit 55l is applied (e.g., between about 0.01 mm to about 4 mm, typically between about 1-2 mm from a marked site 55t). In yet other embodiments, a user can define the boundary limits 55l based on the actual treatment site or treatment type. The user-defined boundary limits 55l can be based on a pull-down menu of suggested limits or a user may enter desired limit dimensions via a UI such as a keyboard or voice prompt and the like.

Figure 6:
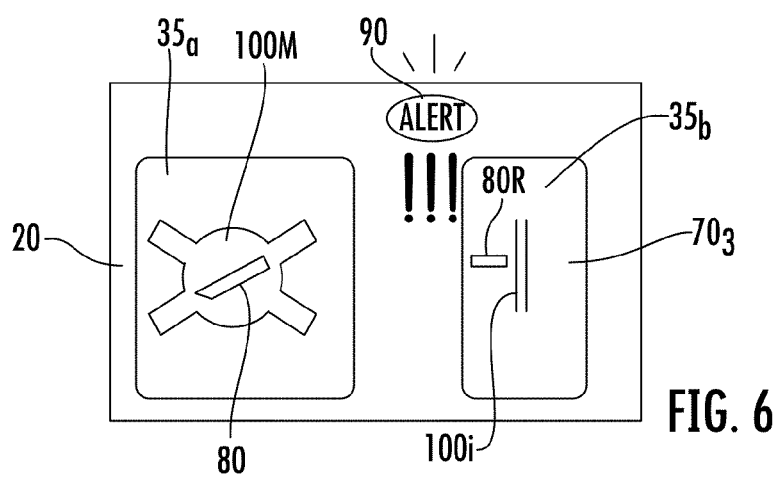
FIG. 6 is a schematic illustration of a system configured to generate proximity alerts according to embodiments of the present invention.

FIG. 6 illustrates that as a physician prepares to ablate tissue proximate one target ablation site 55t along the path 55p, a close-up ablation view is generated using an associated scan plane, for example, $70_3$. However, as shown, the ablation catheter 80 is not where it is expected to be in the close-up side view MRI 35 (a substantially real-time MRI of local tissue taken from a scan plane extending axially along the ablation catheter and projected a distance forward therefrom) to create the lesion at the desired ablation location (not within the target path boundary limits 55l). Thus, a visual and/or audible proximity alert 90 can be generated, shown as using the workstation display 20 and/or speakers.

FIG. 6 also shows the display 20 can include side-by-side viewing windows 35a, 35b one showing the map 137p or other anatomical patient model 100M (typically used during navigation mode and ablation mode) 35a and the other view 35b with images of local tissue during an ablation mode using near real time MR image data during ablation, typically showing a side view of the local tissue and ablation catheter 80 according to embodiments of the present invention.

In conventional cardiac EP systems, physicians "point and ablate" using a tip electrode on an ablation catheter. Embodiments of the invention are directed to allow a physician to "drag" an ablation catheter or other ablation source, typically "back and forth", along a target defined ablation path 55p while information on the location of the ablation catheter 80 (FIGS. 20A-23) and/or target tissue is provided to the user/physician. If the catheter 80 or other source is out of position with respect to a defined target path 55p and the associated boundaries 55l, the system 10 can generate an audible and/or visual warning proximity alert 90 prior to when an ablation lesion is formed.

Figure 16:
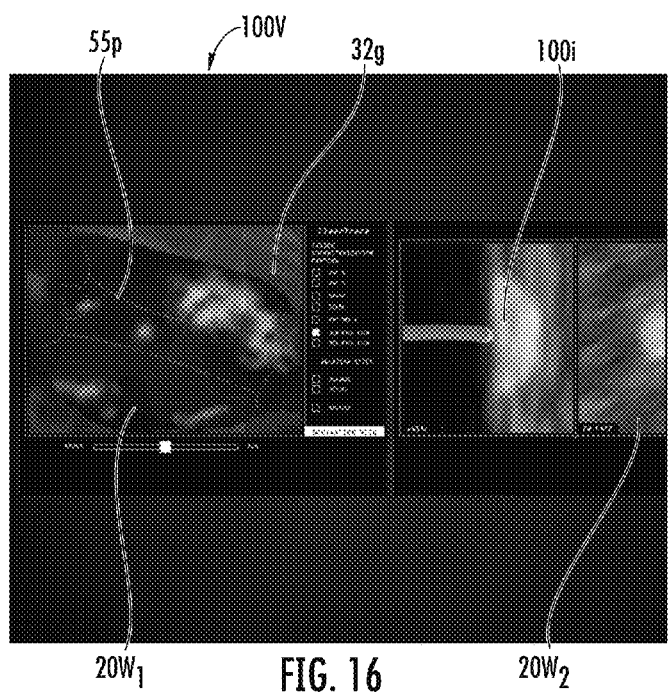
FIG. 16 is a schematic of a display having two viewing windows one showing target ablation sites on a patient model and the other showing contemplated (prophetic) near real time "close-up" MRI images of local tissue, at least the latter images may be generated using one or more pre-set scan planes according to embodiments of the present invention.
Figure 17:
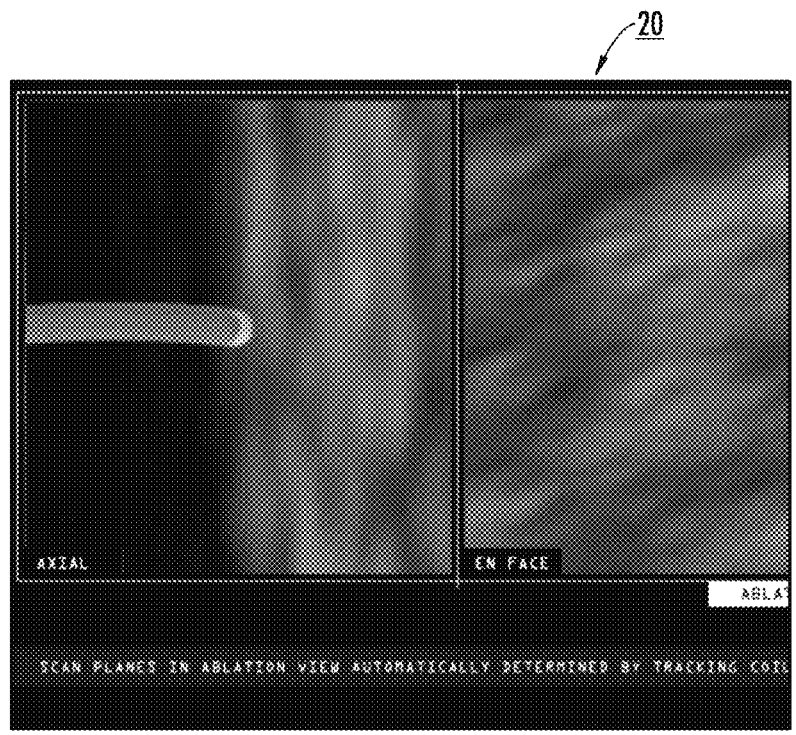
FIGS. 17 and 18 are screen shots showing axial and en face views showing prophetic examples of near real time "close-up" MRI images of local tissue that may be generated using one or more pre-set scan planes according to embodiments of the present invention.

Thus, in some embodiments, the system 10 facilitates cardiac ablation under MRI guidance using a "catheter dragging" approach while applying energy, e.g., RF, heat, optical, light, ultrasound or other energy for ablation. Such a methodology can reduce the need for point to point (RF) ablation. For example, a 3-D volumetric map 13'7p of at least the left atrium (LA), of a patient can be generated during, but typically prior to, an active interventional EP cardiac procedure. The system 10 can be configured to programmatically automatically define a minimum number of scan planes to cover associated intracardiac surfaces targeted for ablation. A physician can modify the number of scan planes if desired. These scan planes 70n can be preset for use during the interventional procedure as described above. As a surgeon plans to drag the catheter for ablating certain areas of the heart associated with different scan planes, such as scan plane "3" ($70_3$) in FIG. 4, the system can electronically/programmatically associate/define boundary limits for the drag lesion, thus setting automatic limits on boundaries of a suitable catheter drag path. These auto-limited 55l drag paths 55p can be electronically defined and incorporated into a procedure plan. As the procedure is performed, scan planes $70_1$-$70_6$, for example, are automatically used to generate MR image data as a catheter nears a location to ablate associated with a location in the planned target ablation path 55p. During drag ablation, a physician follows the defined target ablation paths 55p and does not exceed the limits indicated on the path (to keep from going out of the scan plane). If a tip and/or distal end portion of the catheter 80 goes outside the associated defined scan plane, a proximity alert (alarm) can be generated. As the physician performs a "drag" ablation, the MR Scanner 10S obtains near real-time MR images in the preset scan plane and the physician can see the "drag lesion" as it is created, such as in viewing window $20w_2$ (FIGS. 16, 17).

In some embodiments, the system 10 can be configured to automatically electronically lock the ablation source "off" if the catheter 80 is determined to be out of position relative to one of the boundary limits of a respective predefined target ablation path 55p. A clinician can override the lock status to ablate the local tissue and a scan plane can be adjusted to allow him or her to view this tissue as a close-up MRI (FIGS. 16, 17) or the physician may elect to move the catheter into the desired bounds and the catheter 80 will be shown in position using the pre-set scan plane. As will be discussed further below, the ablation catheter 80 can include tracking coils or other features that allow the system to register the location of the catheter in space and show it in position on the map 100M.

The map 137p and/or 100M can be in grey scale and/or color-coded to provide an easy to understand map or image with different ablation, injection or other treatment sites/paths and/or tissue characterizations shown in different colors and/or with different degrees of a particular characterization shown in gray scale. The term "color-coded" means that certain features or conditions, such as ablated versus non-ablated tissue, target ablation sites and actual ablation sites and the like, are shown with colors of different color, hue or opacity and/or intensity to visually accentuate different conditions or status of tissue or different and similar tissue, such as, for example to show lesions in tissue versus normal or non-lesion tissue or fluid treated tissue versus non-treated tissue for an injection therapy.

In some embodiments, the UI control 25c can be configured to allow a clinician to increase or decrease the intensity or change a color of certain tissue characterization types, e.g., to show lesion tissue or tissue having edema with a different viewing parameter, e.g., in high-contrast color and/or intensity, darker opacity or the like. A lesion site(s) in the tissue characteristic map 100M can be defined based on an ablation position in three-dimensional space (e.g., where an electrode is located based on location detectors, such as tracking coils, when the ablation electrode is activated to ablate), but is typically also or alternately associated with MRI image data in associated scan planes to show an ablation site(s) in an MRI image. The MR image data may also reflect a change in a tissue property after or during ablation during the procedure, e.g., Delayed Hyper Enhancement (DHE), thermal, edema and the like.

The UI control 25c can allow the clinician to request a high resolution or enlarged view of the actual ablated tissue merely by indicating on the map a desired region of interest (e.g., by pointing a finger, cursor or otherwise selecting a spot on the display). For example, a high resolution MR image of suspect tissue in the left superior pulmonary vein (LSPV) can be shown so that the physician can see actual tissue in the desired spot indicated on the map. New targets can be marked on the map as needed (FIG. 18) and again, pre-set scan planes and/or boundary limits can be automatically electronically associated with the new targets by location.

The system 10 (FIGS. 8-10), e.g., a circuit 60c associated with (e.g., that communicates with or is integral to) the MRI Scanner 10S (FIGS. 9-10) can generate proximity alerts 90 when a known (the system includes dimensional and/or configuration data of the device) intrabody device 80 is proximate the at least one avoid zone 155 and/or inside or outside boundary limits of the at least one target treatment site 55t. The system 10 can also optionally automatically use one or more pre-set scan planes 141 during the surgical procedure when the known intrabody device 80 approaches or is in proximity to a defined corresponding target treatment site 55t.

In certain embodiments, during the MRI-guided procedure, the system 10 (e.g., circuit 60c) can interact with the intrabody device 80 to select a relevant pre-set scan plane 141 (coronal, sagittal, transverse) corresponding to a tracked location of a distal end portion of the intrabody device. In some embodiments, the pre-set scan plane(s) 141 used during the MRI-guided procedure is selected based on defined projected distance beyond a distal tip of the intrabody device 80 (axial and/or perpendicular to the distal end portion of the device) in near real time during an MRI-guided surgical procedure. The scan planes can image tissue proximate but beyond the tip of the device such as between about 0-4 mm, typically about 1-2 mm. In some embodiments, the system may automatically enable or disable ECG gating as necessary when defining scan planes, markers, recording electrograms, and the like.

FIG. 7 illustrates a display 20 with a visualization 100v that includes the planning map 137p registered to the imaging space along with MRI image data 100MRI that an MR Scanner 10S can obtain while a patient is in the MR Scanner 10S typically just prior to or at the start of the MRI-guided interventional procedure. The system can be configured to allow a user to "turn on" and/or "off" or fade the planning map 137p or other model 100M and/or the avoid zones 155 or target ablation sites 55t or use a different volumetric map (both generally referred to using feature 100M) of the patient in the visualization 100v during the MRI-guided procedure. The planning map 137p can be imported and electronically interrogated to define the proximity alert locations adjusted to reflect the model registered to the 3-D imaging space. The identification of the proximity alert locations can be "in the background" or shown on the display. The display 20 can include a UI 25c that allows a user to select whether to show the planning map 137p on the display (typically as part of the visualization 100v) and/or to cause the system to identify and correlate the proximity alerts 90 for use during the MRI-guided procedure.

Figure 8:
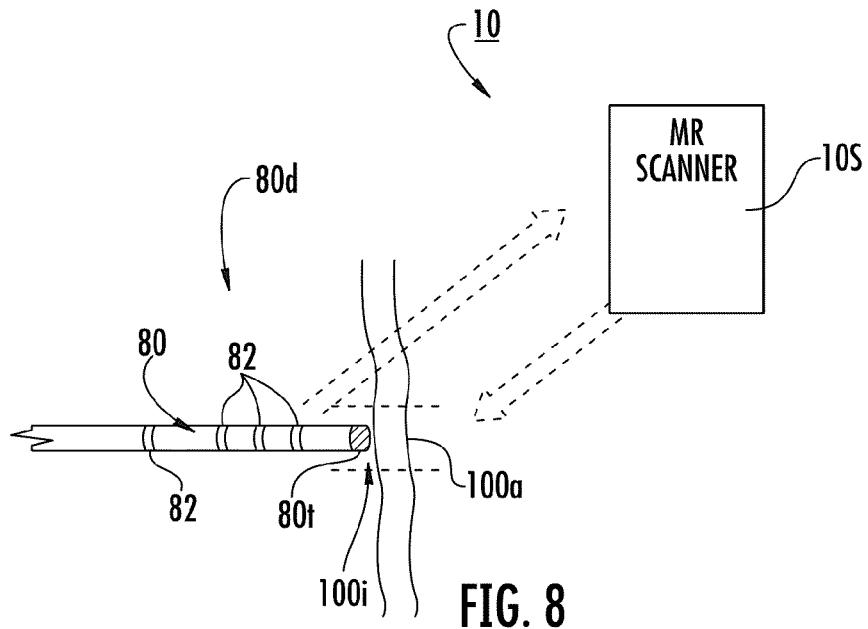
FIG. 8 is a schematic illustration of an MRI-guided system configured to show a device-tissue interface using near RT MRI data according to embodiments of the present invention.

FIG. 8 illustrates an MRI interventional system 10 with a scanner 10S and a (typically flexible) intrabody medical device 80 proximate target tissue 100 at a device-tissue interface 100i. The system 10 can be configured to electronically track the 3-D location of the device 80 in the body and identify and/or "know" the location of at least the tip portion of the device 80t (e.g., the ablation or needle tip) in a coordinate system associated with the 3-D MRI imaging space.

Figure 9:
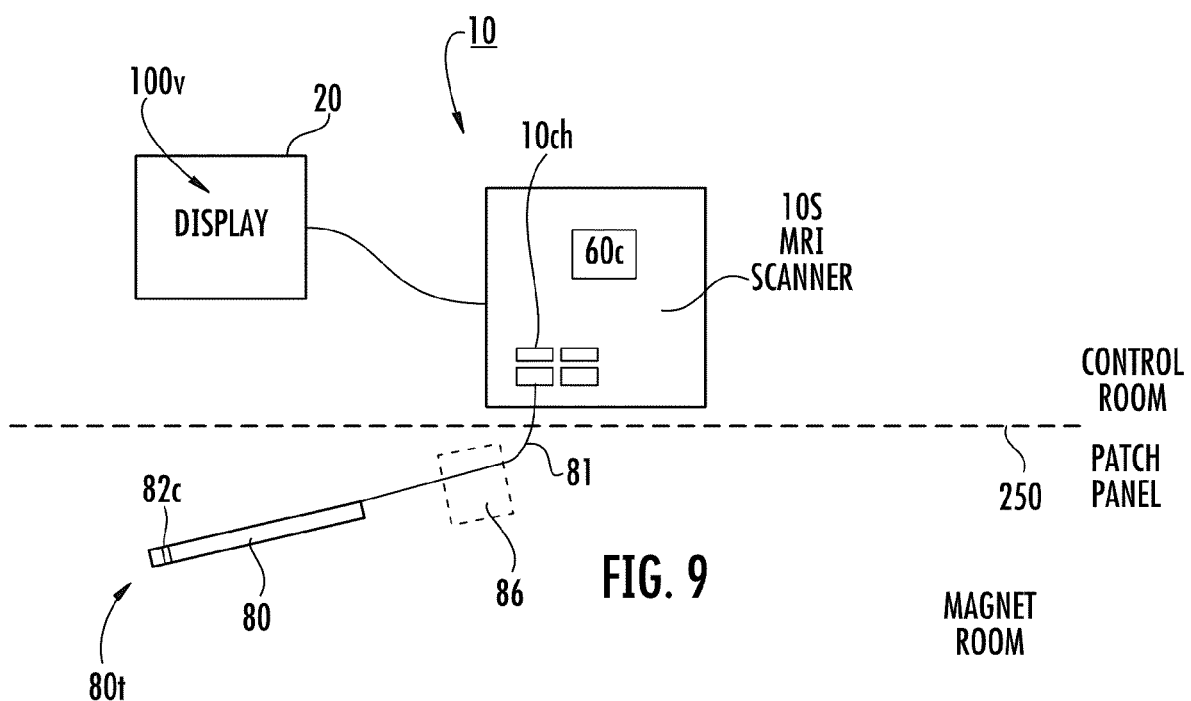
FIG. 9 is a schematic illustration of an intrabody device with a tracking coil electrically connected to a Scanner channel according to embodiments of the present invention.
Figure 10:
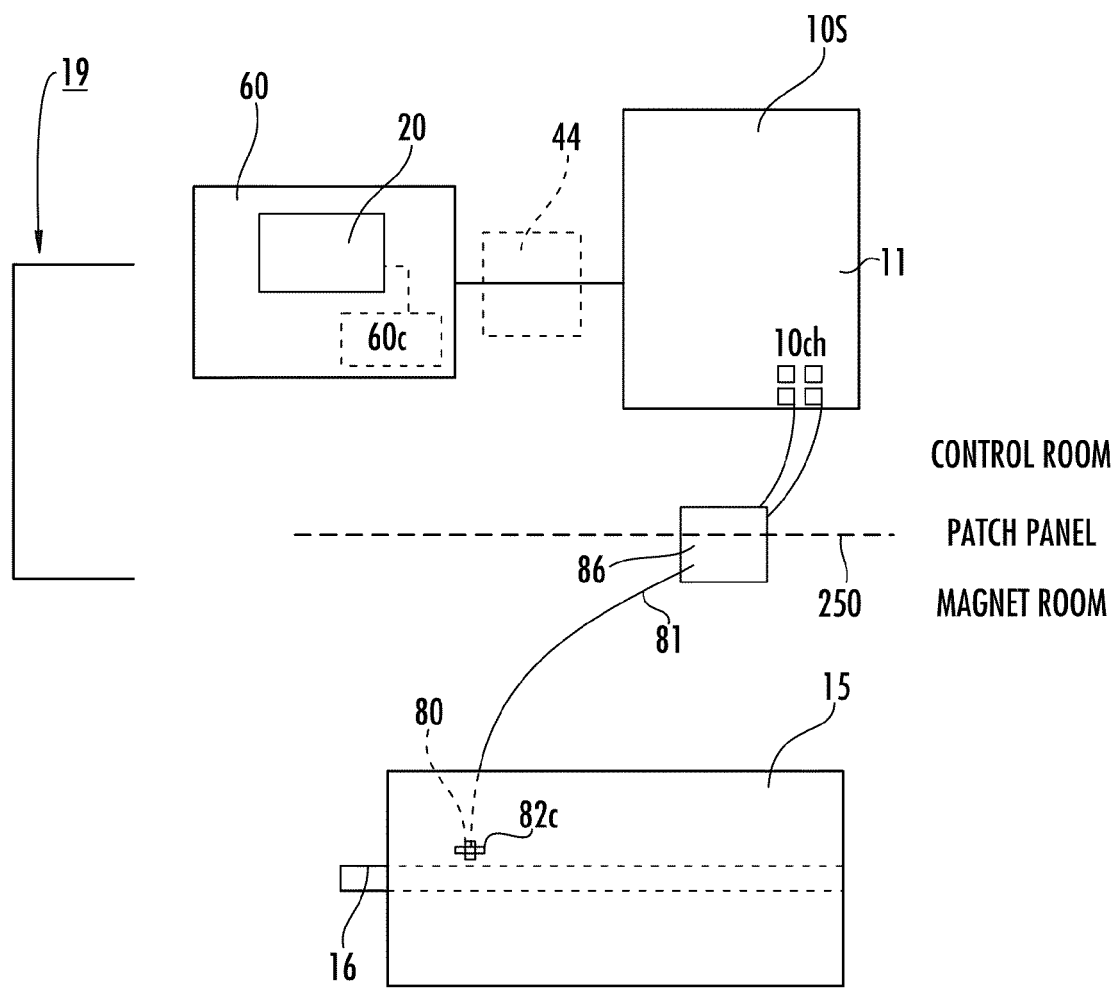
FIG. 10 is a schematic illustration of an MRI system with a workstation and display according to embodiments of the invention.

As shown in FIGS. 9 and 10, the display 20 can be provided in or associated with a clinician workstation 60 in communication with an MRI Scanner 10S. The MRI Scanner 10S typically includes a magnet 15 in a shielded room and a control cabinet 11 (and other components) in a control room in communication with electronics in the magnet room. The MRI Scanner 10S can be any MRI Scanner as is well known to those of skill in the art. Examples of current commercial scanners include: GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio.

The workstation 60 can include the circuit 60c (e.g., ASIC and/or processor with software) that includes or executes part or all of the computer readable program code for generating the pre-set scan planes and/or identifying the pre-set scan planes. However, part or all of the circuit 60c can reside in the MRI Scanner 105, the interface 44 (where used) and/or in one or more remote processors.

Optionally, an MRI scanner interface 44 may be used to allow communication between the workstation 60 and the scanner 105. The interface 44 may reside partially or totally in the scanner 105, partially or totally in the workstation 60, or partially or totally in a discrete device (shown in broken line in FIG. 10). The display 20 can be configured to generate visual and/or audio proximity alerts 90 and render or generate near real time visualizations 100v of the target anatomical space using MRI image data and can illustrate at least one intrabody device 80 in the space. As is known, the at least one intrabody device 80 can comprise one or more tracking coils, passive markers and/or a receive antenna (or combinations of the above).

As shown in FIG. 8, the intrabody device 80 can include a plurality of spaced apart tracking members 82 on a distal end portion thereof. In a particular embodiment, the device 80 can be an ablation catheter and the distal end portion 80d, typically tip 80t, can include an electrode or other therapy device 80e (typically at least one at a distal end portion of the device). Where used, the electrode can be either or both a sensing and ablation electrode.

The tracking members 82 can comprise miniature tracking coils, passive markers and/or a receive antenna. In a preferred embodiment, the tracking members 82 include at least one miniature tracking coil 82c that is connected to a channel 10ch of an MRI Scanner 10S (FIGS. 9, 10). The MR Scanner 10S can be configured to operate to interleave the data acquisition of the tracking coils with the image data acquisition. The tracking data is typically acquired in a 'tracking sequence block' which takes about 10 msec (or less). In some embodiments, the tracking sequence block can be executed between each acquisition of image data (the latter can be referred to as an 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

Embodiments of the present invention provide a new platform that can help facilitate clinical decisions during an MRI-guided procedure and can present near real time anatomical image data to the clinician in a visualization 100v. The visualizations 100v (FIGS. 12A-12D) can be interactive and dynamically generated as the intrabody device 80 moves in the body into a target location, as a user rotates, crops or otherwise alters a displayed visualization or view and/or during an active therapy or diagnostic procedure step, e.g., while ablating at target lesion sites or while injecting (or performing another therapy) tissue, with minimal latent time between serial MRI image data acquisitions, typically less than about 5 seconds, typically substantially continuously with a minimal latent time of about 1 second or less, such as between about 0.001 seconds and 1 second. Together, the system 10 can use the tracking signal(s) and image signal data to dynamically track the device 80 (which is typically a plurality of devices) and present visualizations of the anatomy and one or more intrabody devices 80 in near real-time. The device is tracked in 3-D MRI images space but is not required to be in any of the relevant anatomical scan planes used to obtain MR data for the near RT MRI images.

The term "physical representation" means that the device 80 is not actually imaged but rather is rendered with a physical form in the visualizations, typically with a three-dimensional shape or form. Typically, the physical representation is a partial physical representation which shows the distal end portion of the device in the body in the 3-D MR image space. The physical representation 80R may be of any form including, for example, a graphic with at least one geometric shapes, icons and/or symbols. In some particular embodiments, the physical representation may be a virtual graphic substantial replica substantially corresponding to an actual shape and configuration of the actual physical appearance and/or configuration of the associated device (see, e.g., FIGS. 3, 12A-12D, 14). The physical representation 80R can be electronically generated based on a priori knowledge of the dimensions and configuration of the device (and where the shape can vary, known form factors or a predicable or known change in shape), The tip and each tracking coil on a distal end of a particular device may be shown in a geometric shape (the same or different shapes, e.g., an arrow for the tip and a sphere or block or other (typically 3-D) geometric shape or shapes for tracking coils, each in its real location in the 3-D space and in its relative position on the device and each may be rendered with the same or a different color and with the same or a different shape. For example, the tip and each proximate tracking coil may be shown in a different color.

The system 10 and/or circuit 60c can calculate the position of the tip of the device 80t as well as the shape and orientation of the flexible device based on a priori information on the dimensions and behavior of the device 80 (e.g., for a steerable device, the amount of curvature expected when a certain pull wire extension or retraction exists, distance to tip from different coils 82 and the like). Using the known information of the device 80 and the tracking signals (which are spatially associated with the same X, Y, Z coordinate system as the MR image data) the circuit 60c can generate proximity alerts when the distal end portion of the device 80 is determined to be proximate a defined treatment site 55t and/or proximate a defined avoid zone 155. Optionally, the circuit can also select a scan plane(s) from one of the pre-set scan planes 141 that is most closely correlated to the location of the distal end of the device to rapidly generate visualizations showing a physical representation of the location of a distal end portion of the device 80 with near RT MR images of the anatomy.

In some embodiments, the tracking signal data is obtained and the associated spatial coordinates are determined while a circuit 60c in the MRI Scanner 10S (FIG. 9) and/or in communication with the Scanner 10S (FIG. 10) obtains MR image data. The reverse operation can also be used. The circuit 60c can then rapidly generate relevant proximity alerts 90 and render the resultant visualization(s) 100v (see, e.g., FIGS. 12A-12D) with the device(s) 80 shown with a physical representation based on spatial coordinates of the devices in the 3-D imaging space identified using the associated tracking coil data and the near RT MR image(s).

FIG. 10 illustrates that the device 80 can include at least one conductor 81, such as a coaxial cable that connects a respective tracking coil 82c to a channel 10ch of the MR Scanner 10S. The MR Scanner 10S can include at least 16 separate channels, and typically more channels but may operate with less as well. Each device 80 can include between about 1-10 tracking coils, typically between about 2-6. The coils 82c on a particular device 80 can be arranged with different numbers of turns, different dimensional spacing between adjacent coils 82c (where more than one coil is used) and/or other configurations. The circuit 60c can be configured to generate the device renderings based on tracking coil locations/positions relative to one another on a known device with a known shape and/or geometry or predictable or known changeable (deflectable) shape or form (e.g., deflectable end portion). The circuit can identify or calculate the actual shape and orientation of the device for the renderings based on data from a CAD (computer aided design) model of the physical device. The circuit can include data regarding known or predictable shape behavior based on forces applied to the device by the body or by internal or external components and/or based on the positions of the different tracking coils in 3-D image space and known relative (dimensional) spacings.

Figure 11:
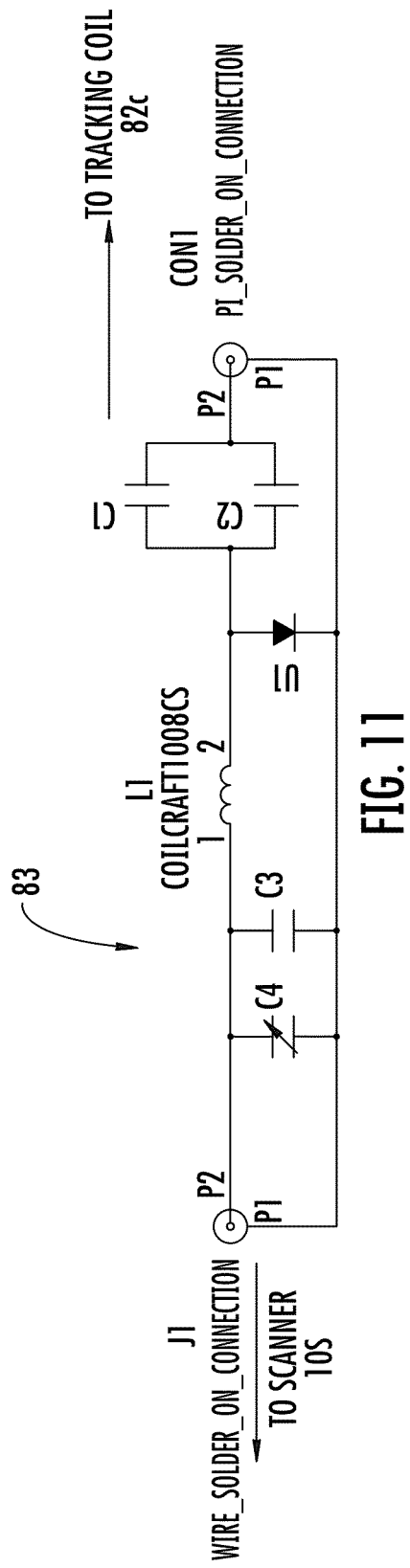
FIG. 11 is a circuit diagram of an exemplary tracking coil tuning circuit according to embodiments of the present invention.

The tracking coils 82c can each include a tuning circuit that can help stabilize the tracking signal for faster system identification of spatial coordinates. FIG. 11 illustrates an example of a tuning circuit 83 that may be particularly suitable for a tracking coil 82*c* on a catheter. As shown, CON1 connects the coaxial cable to the tracking coil 82*c* on a distal end portion of the device 80 while J1 connects to the MR Scanner channel 10*ch*. The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10*ch*. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle or external portion), in a connector that connects the coil 82*c* to the respective MRI scanner channel 10*ch*, in the Scanner 10S, in an interface box 86 (FIG. 10), a patch panel 250 and/or the circuit 83 can be distributed among two or more of these or other components.

In some embodiments, each tracking coil 82*c* can be connected to a coaxial cable 81 having a length to the diode via a proximal circuit board (which can hold the tuning circuit and/or a decoupling/matching circuit) sufficient to define a defined odd harmonic/multiple of a quarter wavelength at the operational frequency of the MRI Scanner 10S, e.g., $\lambda/4$, $3\lambda/4$, $5\lambda/4$, $7\lambda/4$ at about 123.3 MHz for a 3.0 T MRI Scanner. This length may also help stabilize the tracking signal for more precise and speedy localization. The tuned RF coils can provide stable tracking signals for precise localization, typically within about 1 mm or less. Where a plurality (e.g., two closely spaced) adjacent tracking coils are fixed on a substantially rigid material, the tuned RF, tracking coils 82 can provide a substantially constant spatial difference with respect to the corresponding tracking position signals.

The tracking sequence used in the system 10 can intentionally dephase signal perpendicular to the read-out direction to attenuate unwanted signal from 1) bulk objects and 2) regions sensed by other signal sensitive parts of the catheter which couple to the tracking coil (e.g. the coaxial cable along the catheter shaft). This tends to leave only a sharp peak indicating the position of the tracking coil.

The tracking sequence block can include or consist of a plurality of (typically about three) repetitions of a small flip-angle excitation. Each repetition is designed to indicate the x, y or z component of the tracking coil coordinates in succession. Frequency encoding is used along the x-direction to obtain the x-coordinate, the y-direction for the y-coordinate, and the z-direction for the z-coordinate. When the frequency encoding is in the x-direction, the other two directions (y and z) are not spatially encoded, producing projection (spatially integrated) signals in those directions from all excitation regions. The dephasing gradient attempts to attenuate unwanted signal included in these projections. Once the tracking sequence block is complete, a spoiler gradient can be used to dephase any transverse signal remaining from the tracking before the imaging sequence block is executed.

The imaging sequence block obtains a portion, depending on the acceleration rate, of the data used to reconstruct an image of a single slice. If the acceleration rate is 1, then all of the data for an image is collected. If the acceleration rate is 2, then half is collected, etc. If multiple slices are activated, then each successive imaging block collects data for the next slice, in 'round robin' fashion. If any magnetization preparation (e.g., saturation pulses) is activated, these are executed after the tracking sequence block, immediately before the imaging sequence block.

Additional discussion of tracking means and ablation catheters can be found in U.S. Pat. No. 6,701,176, and U.S. Provisional Application Ser. No. 61/261,103, the contents of which are hereby incorporated by reference as if recited in full herein. Exemplary ablation catheters will be discussed further below.

As will be discussed further below, generally stated, in some embodiments, the circuit 60*c* can be configured to allow a user (via a User Interface 25 associated with a display, for example) to selectively show or not show (e.g., turn on/off and/or fade) in one or more visualizations on a display one or more of at least four different data sets in either the rendered model 100M or in near RT MRI images 100MRI of relevant scan planes during a procedure. The model 100M can be a planning model 37M or different patient model.

The different data sets can include a first data set associated with a volumetric model or map 100M of the patient (which may be shown in wire form), a second data set associated with tissue data maps 30 (e.g., tissue data based on image data such as edema, DHE and the like, and/or electroanatomical data), a third typically near-RT MRI scan (image) data set of relevant anatomic structure, and a fourth target site 55*t* data set. As will be discussed further below, a pre-acquired patient planning map can be used to identify at least one target site 55*t* and the planning map can be registered to the 3-D MRI image space which also registers the location of the target site in the 3-D space to allow the target site 55*t* to be shown in the visualizations in proper 3-D space location in either or both the near RT images or in the rendered registered model. The model 100M, the tissue data and the target sites (and the images 100MRI) can be turned "on" or "off" in the visualizations by a user and can be used to drive the MRI-guided procedure. For example, a "live" near RT MRI image of patient tissue can be shown in the visualization and a user (physician) can select to show at least one target treatment site in the image space in the near RT MRI image. The user may also show the model 100M in wire form with or without tissue data (e.g., DHE or edema map data). For example, as a therapeutic device/catheter 80 approaches a target site, the model 100M can be turned off or faded to a faint visibility with respect to near RT images can be shown. A user can also or alternatively select to show the target treatment sites 55*t* in the near RT images 100MRI without the model or with the model faded.

Referring now to FIGS. 12A-12D and 13-18, examples of visualizations 100*v* rendered with a physical representation 80R of the intrabody device 80, a volumetric model 100M of target anatomical structure and a near real-time MRI image 100MRI. As noted above, the model 100M can comprise the planning model 137*p*. The circuit 60*c*/Scanner 10S is configured to present a 3-D volumetric model of at least a portion of the patient's target anatomy (shown as the heart) 100M in the visualization 100*v* with the model registered to the 3-D imaging space along with a physical representation of at least the distal end portion of the at least one intrabody device 80R in the imaging space and can generate audible and/or visual proximity alerts 90 (positive or warning) based on the tracked location of the device 80.

Figure 12A:
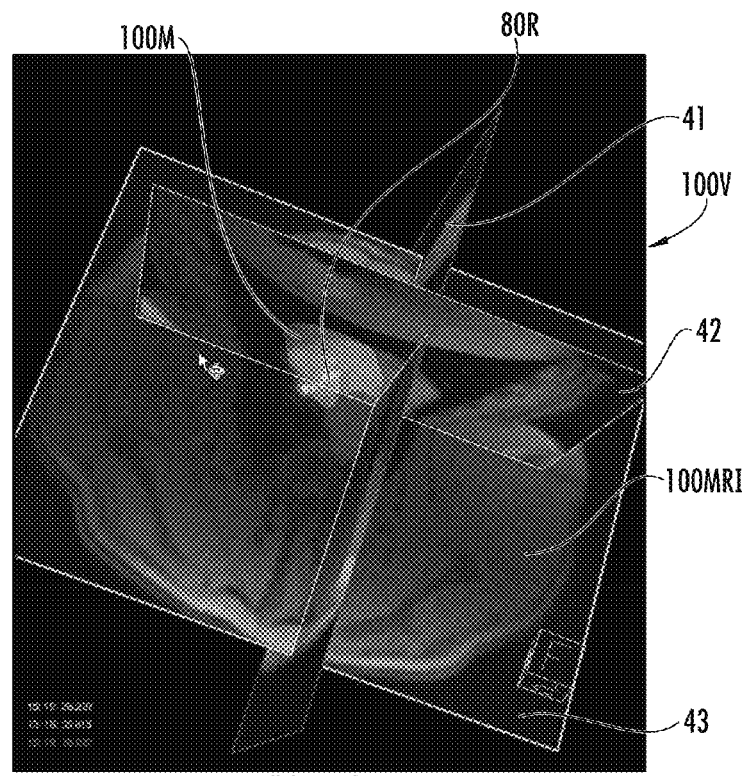
FIGS. 12A-12D are prophetic screen shots of exemplary interactive visualizations with a physical representation of an intrabody flexible medical device according to embodiments of the present invention.
Figure 12B:
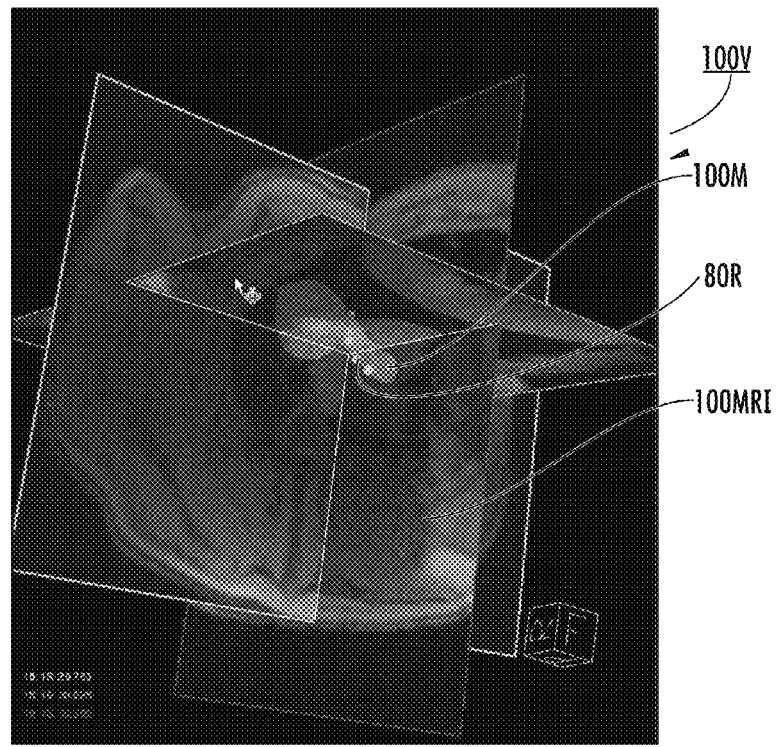
Figure 12C:
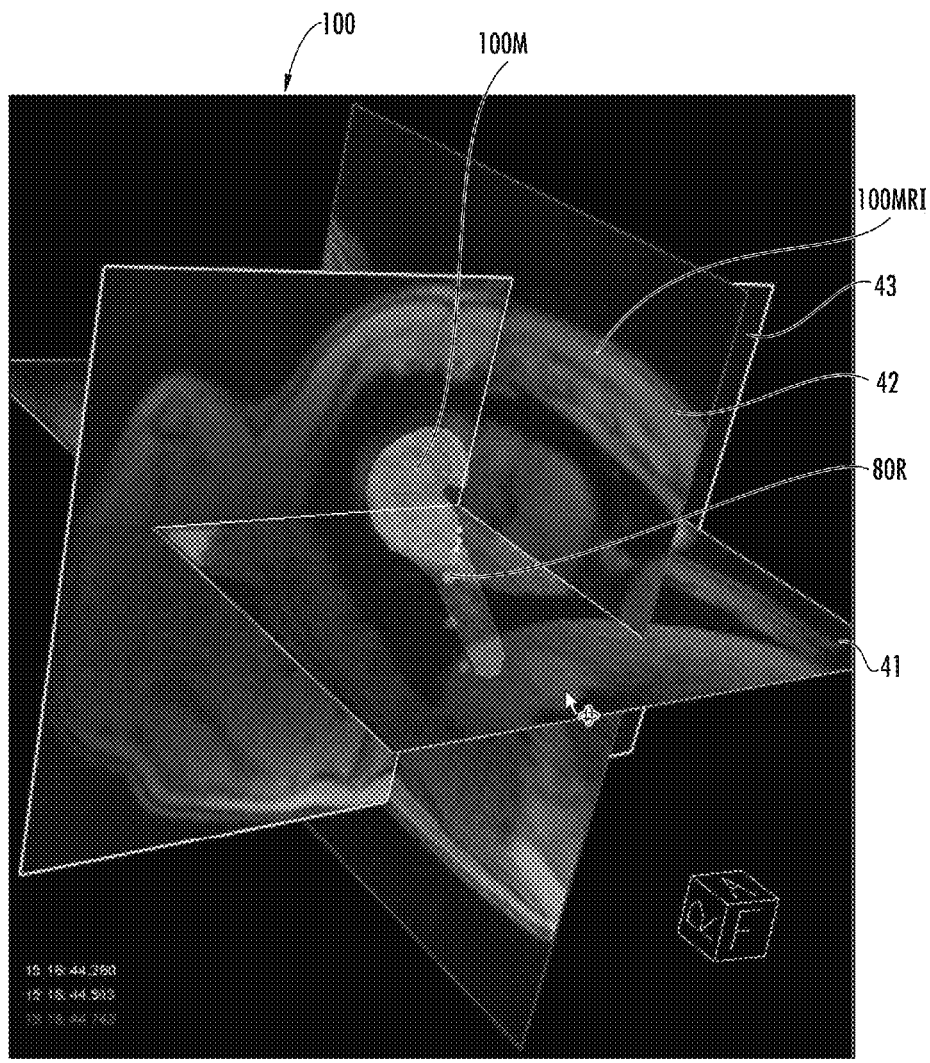

As shown in FIG. 12A, the circuit 60*c* can be configured to generate the visualizations 100*v* with at least two visual reference planes 41, 42 (shown with a third intersecting plane 43) that are oblique or orthogonal to each other and extend through at least a major portion of the visualization 100v. The planes 41, 42 (and 43) can be transparent and/or translucent. They may be shown with different color perimeters that correspond to a respective two-dimensional image slice (which may be shown as thumbnails on the display also with a perimeter of similar or the same color).

The planes 41, 42 can move relative to each other in the imaging space or may be locked together, in any case they can be configured to move relative to the model 100M in the imaging space. As shown in FIGS. 12A-12D, a user can rotate and zoom the visualization 100v which automatically adjusts the visualization shown on the display. As also shown, the flexible device 80 is not required to be in any of the relevant anatomical scan planes used to obtain MR data for the at least one near RT MRI image 100MRI in the visualization and the distal end portion 80d of the flexible device 80 can take on a curvilinear shape and the tip 80t can be steered or guided into different target positions.

Figure 12D:
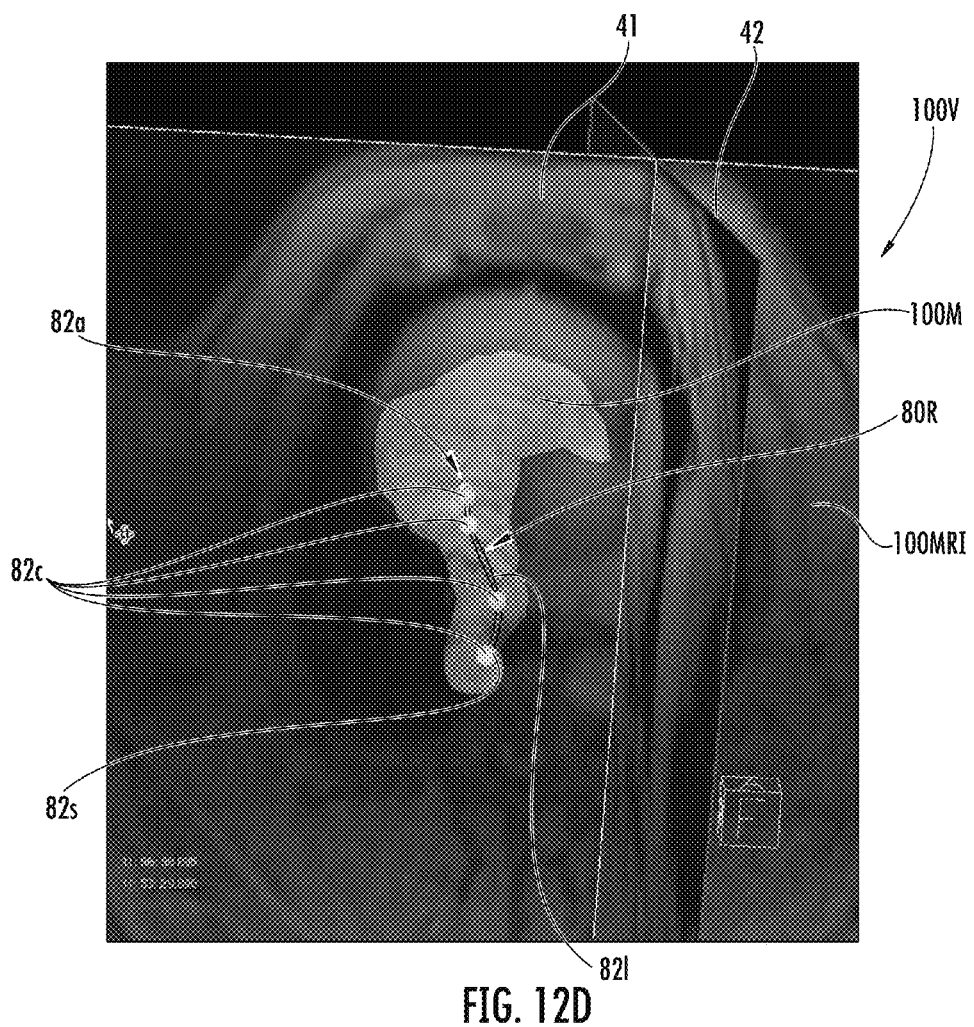

In some embodiments, as shown in FIG. 12D, the circuit 60c is configured to associate a tip location of the at least one device 80 with an arrow 82a and render the visualization so that each tracking coil 82 on the distal end portion 80d has a shape 82s with a color, with each tracking coil 82 having a respective different color from the other tracking coils, and with a line or spline 82l connecting the tip 82a and the coils 82c and the line 82l is able to flex, bend and move to reflect movement of the device 80 in the visualizations 100v.

Figure 13:
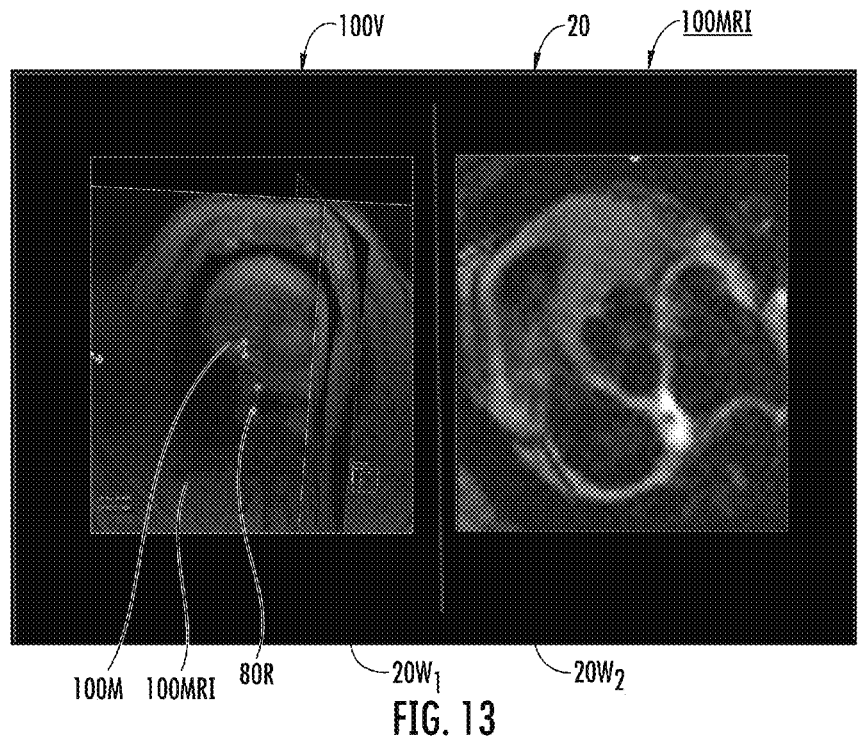
FIG. 13 is a schematic illustration of a display with two viewing windows, one showing an interactive visualization and the other showing prophetic relevant near RT MRI image according to embodiments of the present invention.

FIG. 13 illustrates that the system 10 can be configured to show both the interactive visualization 100v in one viewing window 20w₁ and an MRI image 100MRI alone in a second viewing window 20w₂. The MRI image 100MRI in the second window 20w₂ is typically associated with the target anatomy location identified by a user in the interactive visualization 100v in the first viewing window 20w₁.

Figure 14:
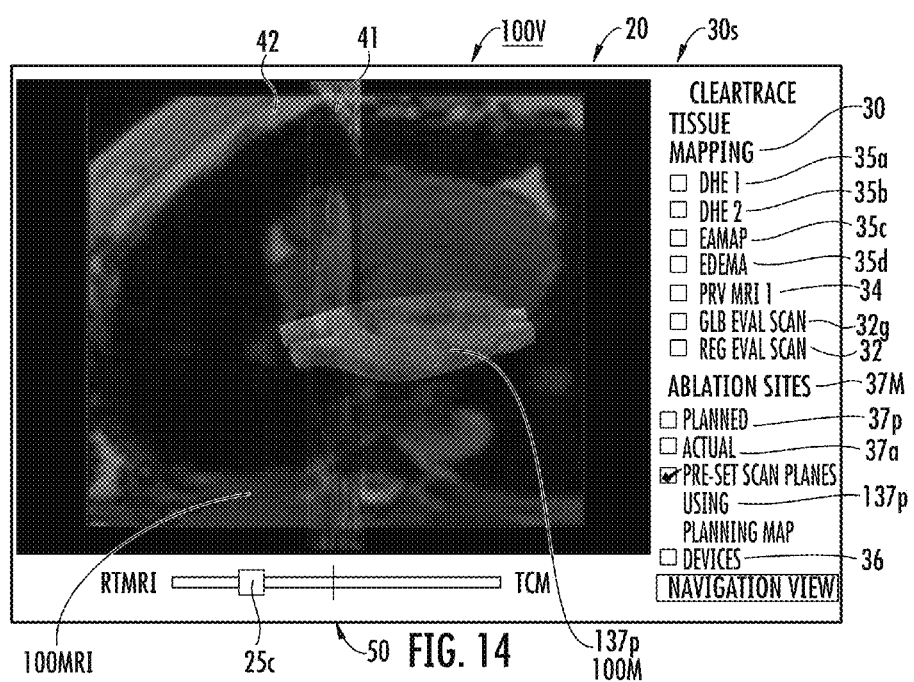
FIGS. 14 and 15 are schematic illustrations of exemplary visualizations and images on a display and UI controls that can be generated to facilitate an MRI guided procedure according to embodiments of the present invention.

As shown in FIG. 14, the display 20 can have a UI 25 with at least one UI control 25c that can be configured to allow a physician or other clinician to select whether to show near real time MR images of target tissue 100MRI either with a model 100M of the target anatomical structure and/or in a separate viewing window. The User Interface control 25c can be configured to allow a user to alter the displayed visualization (fade) to include only a near RT image of the anatomy, to include the near RT image of the anatomy and the registered model of the heart, or to include only the registered model. The UI 25 can be an on off selection of these options or may "fade" from one viewing option to another. As shown, a virtual sliding control 25c allows a user to change what is shown ((near) RTMRI 100MRI to only the Model 100M).

The UI 25 typically includes multiple GUI controls that can include a touch screen input control to allow a clinician/physician to select a region of interest in the map 100M by placing a cursor or by touching the screen at a region of interest. This can cause the system to obtain real time MR image data of that region and provide the associated image on the display and/or define scan planes (which may be preset scan planes 141) at that location in space.

Referring again to FIG. 14, for example, the display 20 can present a UI 25 that allow a user to select to show data from one or more different patient maps 30 with at least some of the maps being tissue characterization maps, so that the map or data therefrom can be "turned on and off" or faded. For tissue characterization maps, the maps include spatially correlated tissue characterization data taken from MR image data incorporated therein as discussed above. The UI 25 can include multiple different GUI (Graphic User Input) controls 25c for different functions and/or actions. The GUI controls 25c may also be a toggle, a touch screen with direction sensitivity to pull in one direction or other graphic or physical inputs.

The UI 25 can be configured to allow a user to zoom, crop, rotate, or select views of the displayed map/model 100M. As shown, one GUI control 25c can be a slide control 50, on a lower portion of the display 20 that can allow a user to select whether to display RT-MRI (Real Time MRI images) 51 or a tissue characterization map 30, or combinations thereof (e.g., the slide can allow a fade-away display between the two types of images). The GUI control 50 may also be a toggle, a touch screen with direction sensitivity to pull in one direction or other graphic or physical inputs.

The circuit 60c can also be configured to generate MRI images which show the device location in near real time (in the MR image space). The UI 25 can also be configured to allow a user to turn off and/or fade the renderings of the device 80 in and out of the visualizations with rendered views of the device versus actual images of the device to confirm location or for additional visual input. The device may include other fiducial markers (e.g., a passive marker or an active marker such as receive antenna) for facilitating the visual recognition in the MR image.

Figure 15:
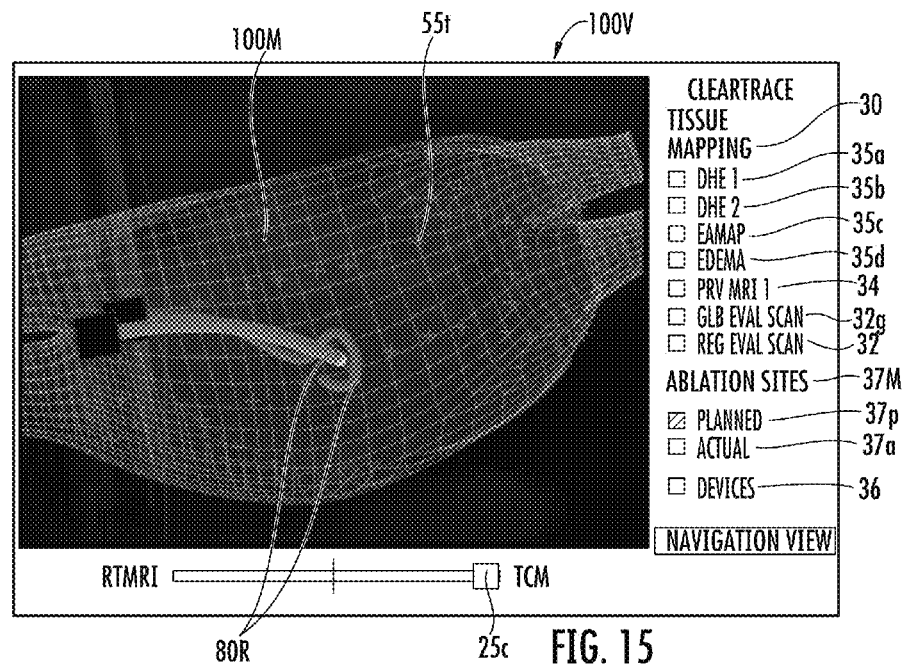

The UI 25 can include a list of user selectable patient-specific images and/or maps including a plurality of tissue maps, typically including at least one, and more typically, several types of, tissue characterization maps (or data associated with such maps) associated with the procedure that can be selected for viewing by a user. The UI 25 can also include GUI controls that allow a user to select two or more of the tissue characteristic maps, with such data able to be shown together (overlaid and registered and/or as a composite image) or separately. As shown, the maps 30 may include at least a plurality of the following:

(a) a regional evaluation tissue characterization map 32 which shows actual lesion patterns in one region to allow a clinician to view regional (ablation) information (such as at the LA (left atrium), a PV (pulmonary vein) and the like) and/or a global evaluation tissue characterization map 32;

(b) pre-procedure MRI cardiac scans 34;

(c) DHE 1 (Delayed Hyper Enhancement) tissue characterization map 35a taken at a first point in time (such as a week or just prior to the procedure);

(d) DHE 2 tissue characterization map 35b taken at a second point in time, such as during a procedure, potentially toward an end of the procedure to confirm complete electrical isolation of the PV (pulmonary veins) or other targets prior to terminating the procedure—alternatively the DHE 2 map can be associated with the end of a prior EP ablation procedure;

(e) an EA (electroanatomical) map 35c;

(f) an edema tissue characterization map 35d;

(g) other tissue characterization maps, for example:

(i) a composite thermal tissue characterization map that shows positions of increased temperature that were caused by ablation of tissue during the procedure;

(ii) ischemic (oxygen deprived or lacking) tissue characterization map;

(iii) hypoxic or necrotic tissue characterization map;

(iv) fibrous tissue map;

(v) vasculature map;

(vi) cancer cell/tissue map (where cancer is the condition being treated);

(vii) a fluid distribution map (for visualizing injected or otherwise delivered therapeutic fluid in local tissue of the target anatomical structure);

(viii) light exposure maps; and (h) at least one procedure planning map 137P with one or more target sites 55t (FIG. 10) and a later tissue map showing target 55*t* and actual treatment sites 55*a* (e.g., target and actual ablation sites) shown in different colors, opacities and/or intensities for ease of reference; and (i) device views 36 that show the physical representation of at least one device 80R in the surgical/imaging space, e.g., an ablation catheter 36*a* shown in position and/or a mapping (loop) catheter 36*b* as devices 80R shown in position (FIG. 15). These device maps 36 may be used/displayed, for example, during a navigation mode. The default action may be to show these devices at least in the navigation mode but a user can also optionally deselect this choice. The devices may also be "turned" off or faded or shown in wire grid or otherwise in the visualizations subject typically to user input.

The display UI 25 can be configured to allow a physician or other clinician to select whether to show real time MR images of target tissue either in the tissue map and/or in a separate view or window (e.g., FIGS. 16 and 17). The UI 25 typically includes multiple GUI controls that can include a touch screen input control to allow a clinician/physician to select a region of interest in the tissue characterization map by placing a cursor or by touching the screen at a region of interest. This can cause the system to obtain near real time MR image data of that region and provide the associated image on the display and/or use preset scan planes associated with that location in the imaging space.

Pre-acquired tissue characterization maps 30 are typically registered to 3-D coordinate space so that the relevant scan planes used to obtain MR image data obtained from the patient during a procedure can be pre-set as discussed above or obtained during the procedure so that the MR image data is in the 3-D MRI image space. Data associated with one or more of the tissue characterization maps can be updated over time (including in near real time) using MR image data automatically or upon request by a user. EA maps can be generated using tracking and/or mapping catheters in the 3-D MRI image space which may provide a more accurate or timely EA map (without requiring registration of a pre-acquired map).

The tissue characteristic map(s) 30 can be generated using MR image data that shows normal and abnormal status, conditions and/or behavior (or a response to treatment) of tissue. For example, the tissue characterization map(s) 30 can show a thermal profile in different colors (or gray scale) of cardiac tissue in a region of interest and/or globally. In other embodiments, the tissue characterization map 30 can illustrate one or more of infarcted, injured, necrotic, hypoxic, ischemic, scarred, edemic (e.g., having edema) and/or fibrotic tissue or otherwise impaired, degraded or abnormal tissue as well as normal tissue or fluid injected into tissue on an anatomical model of the heart. In yet other embodiments, the tissue characterization map can illustrate portions of the heart (e.g., LA or posterior wall) with lesser or greater wall motion, and the like.

In some embodiments, the system can be used to deliver a therapeutic to target anatomy using an injection needle or fluid delivery cannula. A fluid distribution map or data therefrom can be shown on the model 100M or in the MRI image 100MRI (without requiring the rendered model). For example, to treat heart failure, a therapeutic agent can be injected into one or more target locations in infarct or abnormal cardiac tissue. Typically, the injection is carried out in several spots to generate a desired coverage pattern or area/volume. The fluid distribution map can be used to confirm that desired coverage of the cardiac tissue was obtained based on the injections. If not, another ("clean-up") target site or sites can be identified and the sites can be injected with the therapeutic agent. In other embodiments, a previous injection site may need additional volumes of the agent, so that same site can be treated again. The fluid distribution map can be generated based on MRI image data alone. In other embodiments, a fluid distribution map can be generated based on a known injection site or sites, and a known volume of injected agent (which may be measured in situ or based on a known flow rate and known time of injection). This data can be used to generate an estimated fluid distribution map. In other embodiments, a fluid distribution map can be generated based on both MR image data and injection amounts. In some embodiments, the system/circuit 60*c* can indentify a spatial grouping of injection sites and electronically select a scan plane or scan planes that can be set through the injection sites to obtain near RT MRI image data or obtain image data after the injections (such as for a regional or global coverage evaluation prior to the end of the MRI-guided procedure). For cardiac injections for some heart repairs, a planning map 37M identifying infarct tissue and normal (healthy) tissue boundaries can be used to identify target injection sites 55*t*. This map 37M can be registered to the MRI image space. A target site 55*t* can be associated with the X, Y, Z location in the MRI image space. Near RT images 100MRI can be generated during the injections (similar to the ablations) to allow a physician to see "live" the injection distribution or disbursement. This fluid distribution map can be electronically provided as a data set that can be selectively shown on the anatomical model 100M. The therapeutic agent can be any suitable agent including, for example, stem cells (and may be directed to rebuilding cardiac tissue) and is MRI visible.

Other embodiments can generate light exposure maps to evaluate optical light exposure of target tissue (or light activated drugs in such tissue) similar to the fluid distribution map discussed above. The light exposure map can be based on an internal laser or other light source that exposes the tissue to non-ablative energy.

Whether a parameter or tissue characteristic is shown in the tissue characteristic map as being impaired, degraded, treated or otherwise abnormal versus normal can be based on the intensity of pixels of the tissue characteristic in the patient itself or based on predefined values associated with a population "norm" of typical normal and/or abnormal values, or combinations of the above.

Thus, for example, normal wall motion can be identified based on a comparison to defined population norms and different deviations from that normal wall motion can be shown as severe, moderate or minimal in different colors relative to tissue with normal wall motion.

In another example, a thermal tissue characterization map can illustrate tissue having increased temperatures relative to other adjacent or non-adjacent tissue. Thus, for example, during or shortly after ablation, the lesioned tissue and tissue proximate thereto can have increased temperatures relative to the non-lesioned temperature or tissue at normal body temperatures. Areas or volumes with increased intensity and/or intensity levels above a defined level can be identified as tissue that has been ablated. The different treatment (e.g., ablation) sites 55*t* can be shown on the map 30 (which is used interchangeable as 100M) as areas with increased temperatures (obtained at different times during the procedure) and incorporated into the thermal tissue characterization map 30 automatically and/or shown upon request.

In some embodiments, the tissue characteristic map 30 uses MR image data acquired in association with the uptake and retention of a (e.g., T-1 shortening) contrast agent. Typically, a longer retention in tissue is associated with unhealthy tissue (such as infarct tissue, necrotic tissue, scarred tissue and the like) and is visually detectable by a difference in image intensity in the MR image data, e.g., e.g. using a T1 weighted sequence, to show the difference in retention of one or more contrast agents. This is referred to as delayed enhancement (DE), delayed hyper-enhancement (DHE) or late gadolinium enhancement (LGE).

The circuit can be configured to generate a difference or a comparison map that is generated from a pre-procedure or start-of procedure tissue characterization map and an intra-procedure tissue characteristic map to show the differences based on the procedure. The "before" and "after" maps can be electronically overlaid on a display and shown in different colors, opacities and/or intensities or corresponding pixel values from each image in a ROI can be subtracted to show a difference map. Again, the UI 25 can allow a clinician to select or deselect (or toggle between) the before or after tissue characterization maps or adjust display preferences to allow a visual review of differences.

A regional update tissue characterization map 32 can be used to evaluate whether ablated locations have the desired lesion formation. The UI 25 can allow the clinician to request a high resolution or enlarged view of the actual ablated tissue merely by indicating on the regional evaluation tissue characterization map a desired region of interest (e.g., by pointing a finger, cursor or otherwise selecting a spot on the display). For example, a high resolution MR image of suspect tissue in the LSPV can be shown so that the physician can see actual tissue in the desired spot indicated on the tissue characterization map. New targets can be marked on the map as needed and again, pre-set scan planes can be automatically associated with the new targets by location.

The MRI Scanner 10 can be operated substantially continuously to provide image data that can be used to generate updated tissue characteristic maps upon request or automatically. This operation can be "in the background", e.g., transparent to the user so as not to slow down the procedure while providing updated image data during the course of the procedure.

The visualizations 100V may be shown with target ablation sites 55t on the volumetric model 100M along with near real-time MRI image data and physical representations of the intrabody devices 80R. FIG. 15 also shows that the UI 25 can allow a user to show the model in wire/grid form.

FIG. 16 shows the display 20 with side-by-side viewing windows, one window 20w₁ showing the visualization with the map 100M (which may be a tissue characterization map and as shown here is rendered without the intrabody device 80 shown) and the other window 20w₂ showing at least one near RT MRI image of local tissue during an active treatment mode (shown with two views of the near RT images one axial and one en face.

FIGS. 16 and 17 illustrate two high-resolution active treatment views, both showing adjacent different views, shown as an axial and en face view of local tissue. For example, during an ablation mode the circuit can use a default viewing rule to display the near real time MR image data of the affected tissue during an active treatment, e.g., ablation, typically showing both en face and side views of the local tissue and treatment (ablation tip) according to embodiments of the present invention. In certain embodiments, the interactive visualization map 100v and/or model 100M may not be displayed during all or some of the ablation.

The scan planes used to generate the MR images for the active treatment (e.g., ablation) views can be automatically determined based on the known position of the tracking coils in 3-D imaging space. The scan planes used for the active treatment views of the near RT images may be pre-set scan planes 141 that are electronically automatically selected based on the determined location of one or more tracking coils 82c when it is in proximity to a corresponding location of a defined target site 55t that was previously identified (such as on planning map 137p that was subsequently registered to the MRI imaging space).

Figure 18:
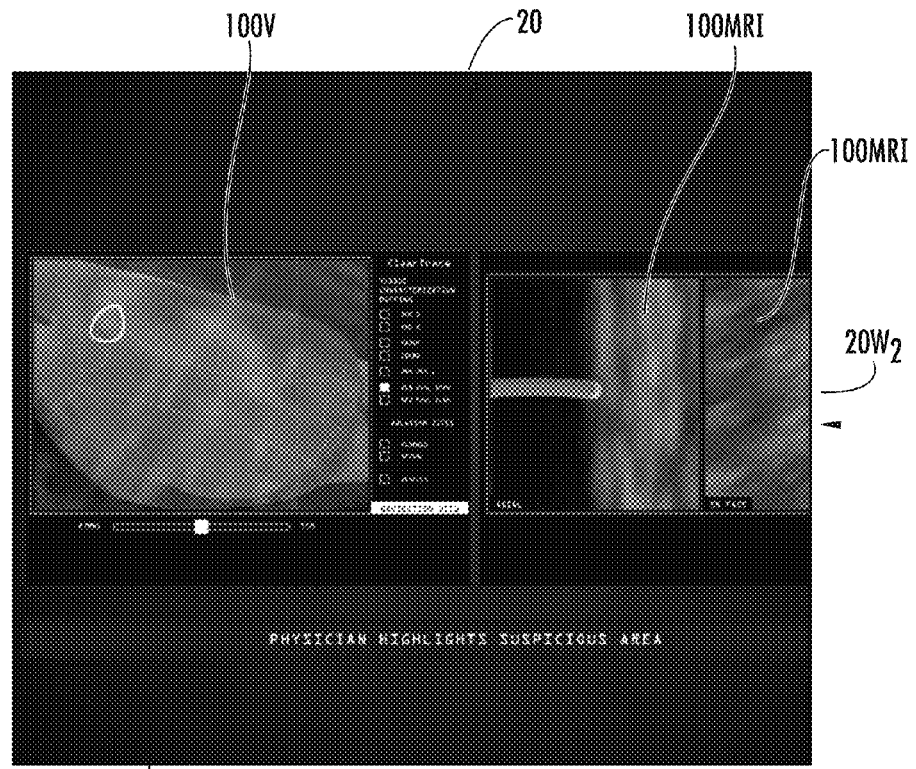

FIG. 18 illustrates that a clinician (physician) can mark an area on the model 100M of the interactive visualization 100v, the mark shown as a circle toward the left side of the left window. The marked area in FIG. 18 in one viewing window 20w₁ may define the scan plane(s) for the close-up near RT image views in the right hand viewing window 20w₂.

FIG. 19 illustrates a cardiac MRI Interventional suite 19 with an integrated cable management system that connects multiple patient connected leads that remain in position even when a patient is translated in or out of a magnet bore on the gantry 16 (the magnet can be an open face or closed magnet configuration) to allow a clinician direct access to a patient. The other ends of the leads connect to power sources, monitors and/or controls located remote from the patient (typically in the control room not the magnet room). As shown in FIG. 19, the MRI interventional suite 10 can include an IV pole 140 (typically attached to the scanner table 120) and a connection block 150 of cables 200n that are routed through a ceiling (e.g., they extend up, through and above a ceiling) (where "n" is typically between about 1-400, typically between about 5-100), that connect to patch bay 135 and/or 137. Cabling 210n for anesthesia cart 160 can also be routed through the ceiling (where n is typically between about 1-400, typically between about 5-100). The cabling 200n, 210n extends through the ceiling 300 between the rooms 10a, 10b and can connect to the remote devices 500 through a patch panel 250. In some embodiments foot pedal cabling 220n can extend through a floor trough to the patch panel/second room 10b as well (where "n" is typically between about 1-100 cables). For additional description of an exemplary cardiac suite, see, U.S. patent application Ser. No. 12/708,773, the contents of which are hereby incorporated by reference as if recited in full herein.

In some embodiments, the system includes a navigation view mode and an ablation view mode for some cardiac procedures. The latter viewing mode can automatically be shown on the display 20 during an active ablation. The circuit 60c can electronically define pre-set scan planes 141 associated with a respective target ablation site 55t which is correlated (registered) to an actual location in 3-D space which is then electronically stored in electronic memory as default pre-set scan planes 141 for that target location 55t. The near RT MRI images in ablation-view mode can automatically be displayed when the ablation or mapping catheter reaches the corresponding physical location in the heart during the procedure. The planned target sites 55t can also used to define the physician view (3-D perspective), e.g., a preset view, whenever the ablation catheter is in the location associated with the target site. Thus, the target sites 55t identified in the planning tissue characterization map 137p can be used to preset both associated scan planes for the near real time MRI and the 3-D perspective view for display without requiring further clinician input.

During some MRI-guided procedures, as the intrabody device 80 (e.g., ablation catheter) approaches a location that corresponds to a target site 55t and/or avoid zone 155, the circuit 60c (e.g., MR Scanner) can generate one or more proximity alerts 90. The circuit 60c may also cause or direct the Scanner to use to "snap to" a scan plane proximate the device (e.g., catheter) tip or end location to obtain real-time MR image data of the associated tissue. The scan planes can be adjusted in response to movement of the device (as typically detected by tracking coils) prior to active treatment (e.g., ablation) if the physician decides the location is unsatisfactory. The snap to scan planes can be based on a calculated projected position of the distal end portion of the device (typically selected so that the slice includes a region projected forward a distance beyond the device such as between about 0-4 mm, typically about 1-2 mm) and/or using one or more of the preset scan planes associated with that location to obtain real-time MR image data of the associated tissue.

In some embodiments, the snap-to scan plane(s) can be carried out based on the position of two closely spaced tracking coils 82c on a distal end of the device 80. The two coils 82c can be held on a relatively rigid substrate or catheter end with between about 2-10 turns/coil. The tracking coils 82c can be connected via a respective coaxial cable to the MR scanner 10S as noted above. The snap-to or projected scan plane can be projected a distance beyond the calculated tip location, such as between about 0-4 mm as discussed above. This embodiment may be particularly suitable for a deflectable end ablation catheter. In other embodiments, such as for a loop catheter, the tracking coils 82c can be held on a loop end of the device and reside on a common plane. The circuit 60c can be configured to define the plane based on the location of at least three of the tracking coils 82c. The tissue-device interface for the snap-to location can be selected to be parallel and proximate the identified plane (e.g., between about 0-4 mm from the plane). In yet another embodiment, a device can have between about 1-20 tracking coils along its length (e.g., along a distal end portion thereof). The snap-to location can be based on a location that is tangent and in-line with at least two of the tracking coils (as the device may deflect and the position of at least some of the tracking coils may change relative to each other).

The circuit 60c can adjust the scan planes as needed if the physician moves the device to obtain slices that show the treatment (e.g., ablation of the lesion) including either or both side and en face views showing substantially real-time MRI of the tissue being treated (e.g., ablated). The slices can include a view generated axially along the line of the device at the interface of the device and tissue and can project forward a defined distance into tissue for the side view.

For an optimal or proper en face view the scan plane can be oriented to a plane that is substantially parallel to the target tissue surface (e.g., proximate a tip of the device). This can be done based on coordinates of the 3D segmentation/model relative to the tip position.

To obtain a slice with a relevant scan plane for the en face view, the device tip can be used to define one point and the circuit could identify a plurality of additional points (e.g., about three more points) on the surface of the model 100M. Those additional points can be a short radius away from the device tip (i.e., similar to a spoke and wheel pattern). Distance of the (three) radial points should be closely spaced relative to the center point, particularly for curved tissue surfaces (e.g., the cardiac walls being ablated or otherwise treated will usually be curved, and in some cases, even have complex curves like the PV ostia). Choosing this distance may be made with reference to typical human cardiac anatomy, the distance of those points may be between about 3 to 5 mm. In some particular embodiments, the following steps may be used to obtain the en face views.

1. Project a line forward from the most distal tracking coils on the intrabody device,
2. Electronically generate (e.g., mark) a temporary point where that projected line intersects the surface of the 3D model
3. Use that temporary point of intersection as the center of the "wheel" and calculate the location of three points on the rim of the wheel.
4. Proscribe a temporary plane that includes the three rim points.
5. Translate the temporary plane until the temporary center point becomes coterminous with the actual tip of the device (assuming that the tip is actually against the target tissue (e.g., cardiac wall).
6. Set the scan plane based on this calculated plane for the en face view.

It is noted that the above steps may not be suitable where the device is a loop catheter. When using a loop catheter as the intrabody device with the tracking coils, the physician typically ablates on the inside of the loop and the circuit can use the coordinates of the tracking coils on the loop catheter to describe the scan plane for the en face view.

In some embodiments, the system can keep track of the shortest line from the tip of the device to the registered model, and can even display this line in near real-time in the rendering(s). Then, with user input, e.g. on a button press, the circuit 60c can define a plane tangent to the model surface for the en face view, or along this line for the axial view. Gating may be used. The axial view may be more robust as it cuts through the wall.

In addition to continuous collection of "new" image data, the data can also be processed by algorithms and other means in order to generate and present back to the surgeon in near real-time or upon request, a substantially continuously updated, patient specific anatomical tissue characterization map of a portion of the heart of interest.

During ablation MR thermometry (2-D) can be used to show real-time ablation formation taking a slice along the catheter and showing the temperature profile increasing. It is contemplated that 2D and/or 3D GRE pulse sequences can be used to obtain the MR image data. However, other pulse sequences may also be used.

In some embodiments, an EA (electroanatomical) map can be obtained prior to (typically immediately prior to) the actual interventional MRI-guided procedure either while the patient is in the MRI scanner or from an X-ray based system from which the EA map can be registered to a tissue characteristic map 30 and shown on the display 20. In some embodiments, the tissue characterization map can include, incorporate, overlay or underlay data from an electroanatomical map (which may be imported from an X-ray imaging modality or generated in an MRI Scanner) to define an integrated electro and tissue characterization combination map. The electrical activity can be detected via electrical activity sensors that can detect impedance or other electrical parameter that can sense fractionated or normal electrical activity in cardiac tissue as is known to those of skill in the art. If so, the electroanatomical map can be registered to the tissue-characterization map so that MR data updates using MR data that is generated during the intervention can be generated and displayed on the integrated map.

Also, the UI 25 can be configured to allow a clinician to select or deselect the electroanatomical map (where used) so that the information from the electroanatomical map is electronically stripped or removed (and/or added back in) to the tissue characteristic map as desired. In other embodiments, the tissue characterization map is maintained separate from the electroanatomical map, and if used, the electroanatomical map is shown in a separate window or screen apart from the tissue characterization map.

In some embodiments, the device-tissue interface 100i (FIGS. 8, 16) can be visualized with a T1-weighted FLASH sequence (T1*w* FLASH) to localize the tip 80*t*. RF or other ablative energy can be delivered and myocardial or other target tissue changes and lesion formation can be visualized in near real-time using a T2 weighted HASTE (T2*w* HASTE) sequence. Real Time (RT)-MRI sequence, T1*w* FLASH and T2*w* HASTE image slices can be aligned to allow visualization of the device 80 upon tissue contact or activation of the ablation energy to allow visualization of the device 80 (e.g., catheter), the device-tissue interface 100*i* and/or the (myocardium) tissue while receiving the therapy, e.g., ablative energy.

In some particular embodiments, during navigation mode (rather than an ablation mode), the catheter 80 can be visualized using a different pulse sequence from that used in the high-resolution ablation mode, such as, for example, an RT MRI sequence using GRE or SSFP (e.g., TrueFISP) pulse sequence with about 5.5 fps), the tracking coils 82*c* can be used for spatial orientation and positioning. Typical scan parameters for (near) real-time include: echo time (TE) 1.5 ms, repetition time (TR) 3.5 ms, a flip angle of about 45 degrees or about 12 degrees, slice thickness 5 mm, resolution 1.8 mm×2.4 mm, parallel imaging with reduction factor (R) of 2.

Once the device position is deemed appropriate (using tracking coils 82*c*), a pulse sequence at the associated scan plane can be used to generate high resolution visualization of the catheter tip 80*t* and (myocardial) tissue interface. For example, a T1-weighted 3D FLASH sequence (T1*w* FLASH) as noted above. Myocardial or other target tissue images during ablation or other therapy can be acquired using an Inner Volume Acquisition (IVA) dark-blood prepared T2-weighted HASTE (T2*w* HASTE) or dark-blood prepared Turbo Spin Echo (TSE) sequence. Examples of HASTE and TSE sequence parameters include: TE=79 ms/65 ms, TR=3 heart beats, 3 contiguous slices with thickness of about 4 mm, resolution 1.25 mm×1.78 mm/1.25 mm×1.25 mm, fat saturation using SPAIR method, and parallel imaging with R=2, respectively. For near real-time SSFP, a typical flip angle is about 45 degrees.

Typical heart beat rates and free breathing can present imaging challenges. In some embodiments, (near) RT navigation imaging slices (e.g., GRE pulse sequence at 5.5 fps) can be aligned with high-resolution tissue interface slices (e.g., T1*w* FLASH) for visualization of the catheter-tissue interface. Subsequently, those slices obtained with T1*w* FLASH can be aligned with those obtained with dark-blood prepared T2*w* Haste images for myocardial tissue/injury characterization during energy delivery. This stepwise approach can allow confident localization of specific points within the atrium and while ablating tissue and simultaneously visualizing the tissue for near-real time assessment of tissue injury associated with lesion formation.

In some embodiments, slices acquired with different sequences can be interlaced to provide an interactive environment for catheter visualization and lesion delivery, a UI can allow a user to toggle between these views or can alternate the views based on these image slices or navigation versus ablation or other interventional modes/views. It is also noted that the sequences described herein are provided as examples of suitable sequences and it is contemplated that other known sequences or newly developed sequences may be used for cardiac ablation or other anatomy or interventional procedures.

As is known to those of skill in the art, there are typically between about 60-100 lesions generated during a single patient cardiac (AFIB) EP procedure. Other cardiac procedures may only require about 1 ablation or less than 60. A typical patient interventional cardiac procedure lasts less than about 4 hours, e.g., about 1-2 hours. Each lesion site can be ablated for between about 30 seconds to about 2 minutes. Linear transmural lesions (such as "continuous" drag method lesions) may be generated and/or "spot" lesions may be generated, depending on the selected treatment and/or condition being treated. The continuous lesion may be formed as a series of over lapping spot ablation lesions or as a continuous "drag" lesion.

The system can include a monitoring circuit can automatically detect which devices are connected to the patient patch bay. One way this can be achieved is by using ID resistors in the patch bay and/or interface as well as in various devices that connect thereto. The MRI scanner computer or processor or the clinician workstation module or processor can monitor resistors via connections CON1, CON2 and CON3. The devices 80 (FIGS. 8-10) can have built-in resistors that modify the resistance by lines that connect to CON1, CON2 and CON3. Variation in resistance values helps the monitor which device is connected. Once that determination is made the scanner may automatically load special acquisition parameters, display parameters and update the progress of the procedure to display on the display 20 such as at workstation 60 (FIG. 9), for example.

Electrical isolation between the MR Scanner 10S and the device 80 can be provided via low pass filters inside and outside the MRI suite. As is known to those of skill in the art, components in the MRI Suite can be connected to external components using a waveguide built into the RF shield that encloses the MRI suite. The ablation catheter 80 can be connected to an appropriate energy source, such as, where an RF electrode is used, for example, a Stockert 70 RF generator (Biosense Webster, Diamond Bar, Calif., USA) with MR compatible interface circuits configured for 3 T magnetic fields (where a 3 T system is used). The system can comprise an EP Suite with a Siemens Verio system (Siemens Healthcare, Erlangen, Germany) or other suitable scanner as well as suitable external imaging coils, such as spine and/or body array coils as is known to those of skill in the art. Other ablation catheters including balloon (cryoablation), laser, ultrasound and the like may also be used in lieu of or with the RF electrode ablation catheter. Other therapeutic catheters or devices may be used including an injection needle catheter and the like.

FIGS. 20A, 20B, and 21-23 illustrate exemplary embodiments of a flexible (steerable) ablation catheter 80A as the device 80. The ablation catheter 80A includes an elongated flexible housing or shaft 102 having a lumen 104 (FIG. 20B) therethrough and includes opposite distal and proximal end portions, only the distal end portion 106 is illustrated. The distal end portion 106 includes a tip portion 101 that contains an ablation electrode 110 at its tip 80*t* for ablating target tissue, and a pair of RF tracking coils 82*c*, individually identified as 112, 114. The distal end portion can include a second electrode for sensing local electrical signal or properties or the ablation electrode 110 can be bipolar and both ablate and sense. The proximal end portion of the catheter 80A is operably secured to a handle as is well known. The catheter shaft 102 is formed from flexible, bio-compatible and MRI-compatible material, such as polyester or other polymeric materials. However, various other types of materials may be utilized to form the catheter shaft 102, and embodiments of the present invention are not limited to the use of any particular material. In some embodiments, the shaft distal end portion can be formed from material that is stiffer than the proximal end portion and/or a medial portion between the distal and proximal end portions.

The catheter 80A can be configured to reduce the likelihood of undesired deposition of current or voltage in tissue. The catheter 80A can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current.

The device 80A tracking coils 112, 114 (FIGS. 20A, 20B, 21) on a distal end portion of the catheter (typically upstream of the ablation electrode 110 on the tip of the catheter 80t) as all or some of tracking members 82 (FIG. 8). The catheter 80A can comprise coaxial cables 81 that connect the tracking coils to an external device for tracking the location of the catheter in 3-D space. The catheter 80A can include an RF wire 120 that connects the ablation electrode 110 to an RF generator (FIG. 19). The conductors 81 and/or RF wire 120 can include a series of back and forth segments (e.g., it can turn on itself in a lengthwise direction a number of times along its length), include stacked windings and/or include high impedance circuits. See, e.g., U.S. patent application Ser. Nos. 11/417,594; 12/047,832; and 12/090,583, the contents of which are hereby incorporated by reference as if recited in full herein. The conductors (e.g., coaxial cables) 81 and/or RF wire 120 can be co-wound in one direction or back and forth in stacked segments for a portion or all of their length.

In some embodiments, the ablation tip 80t is provided with one or more exit ports 132 (FIG. 20A) in communication with a fluid channel through which a fluid/solution (irrigant), such as saline, can flow before, during, and/or after the ablation of tissue. Fluid/solution is provided to the one or more exit ports 132 via an irrigation lumen 134 (FIG. 22) that extends longitudinally through the catheter shaft lumen 104 from the exit port(s) 132 to a handle. The irrigation lumen 134 is in fluid communication with a fluid/solution source at the proximal end portion 108 of the catheter shaft, typically at the handle. The fluid/solution can provide coolant and/or improve tissue coupling with the ablation electrode 110.

In some embodiments, a pull wire 136 (FIGS. 22, 23) extends longitudinally within the catheter shaft lumen 104 from the distal end portion 106 to the handle at the catheter proximal end portion. The pull wire 136 extends longitudinally within a sleeve 138 (FIG. 22) that is attached to the internal wall of the lumen 104. The pull wire 136 is attached to the sleeve 138 near the distal end portion 106 of the catheter 80 and otherwise is slidably disposed within the sleeve. Pulling the pull wire 136 in a direction towards the handle causes the tip portion 101 of the catheter to articulate in one direction. Pushing the pull wire 136 in the opposite direction away from the handle causes the tip portion 101 to articulate in another different direction.

Figure 20A:
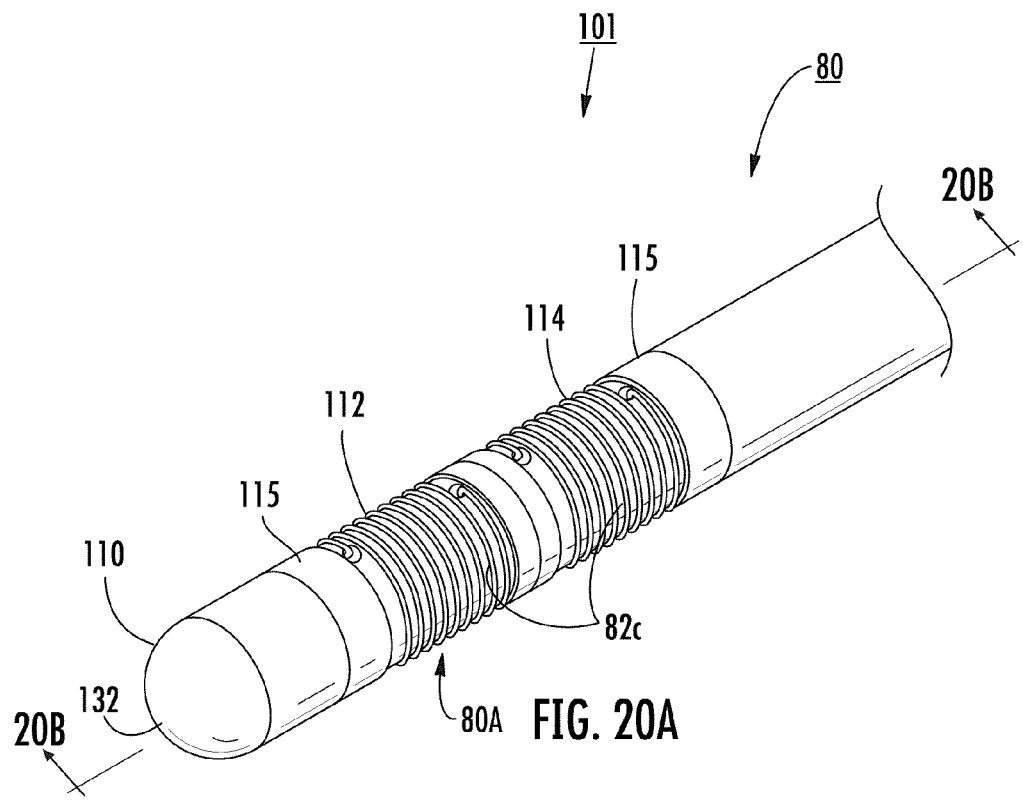
FIG. 20A is an enlarged partial perspective view of a tip portion of an exemplary ablation catheter according to particular embodiments of the present invention.
Figure 20B:
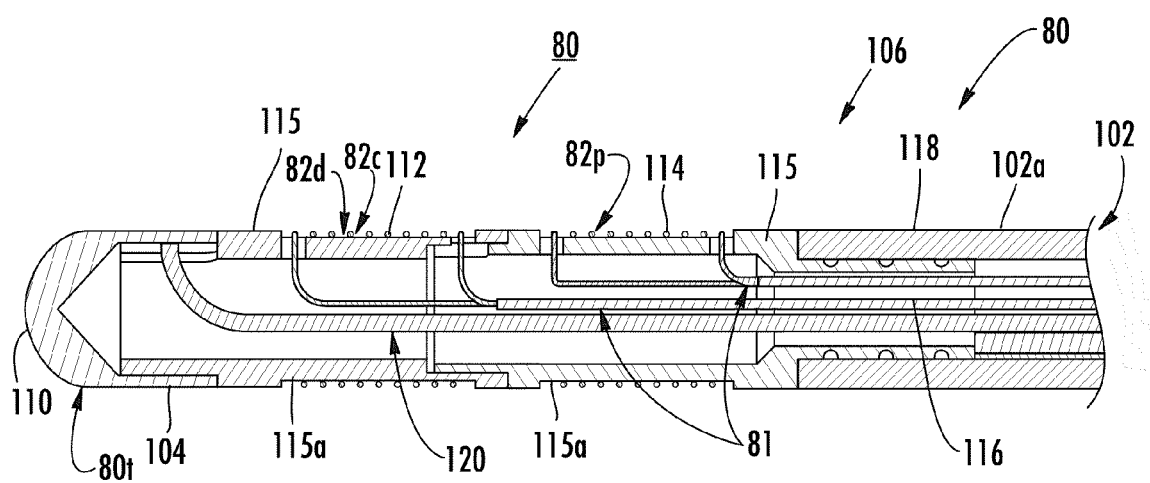
FIG. 20B is a cross-section of the tip portion of the catheter taken along lines 20B-20B in FIG. 20A.
Figure 21:
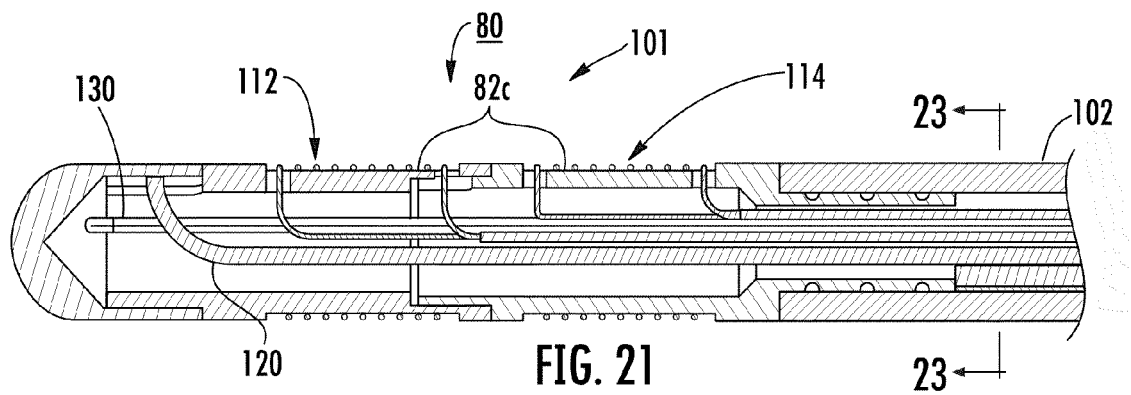
FIG. 21 is an enlarged axial cross section of a tip portion of another example of an ablation catheter according to embodiments of the present invention.
Figure 22:
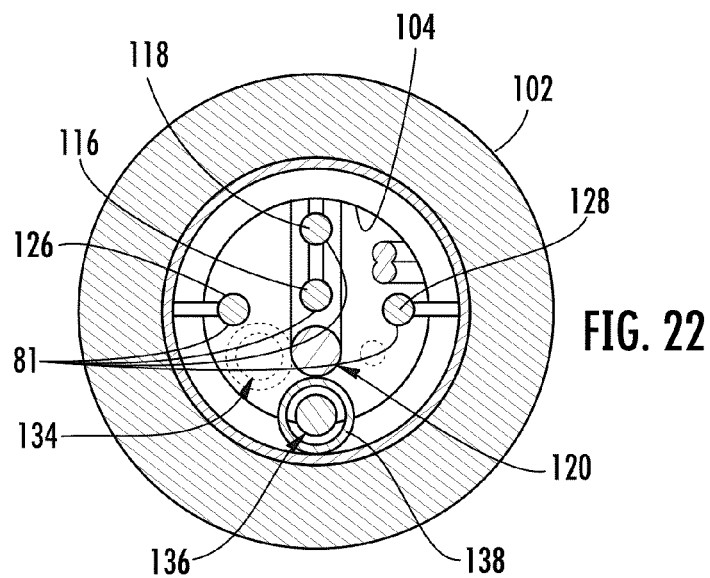
FIG. 22 is an enlarged cross-section of the catheter shown in FIG. 21.
Figure 23:
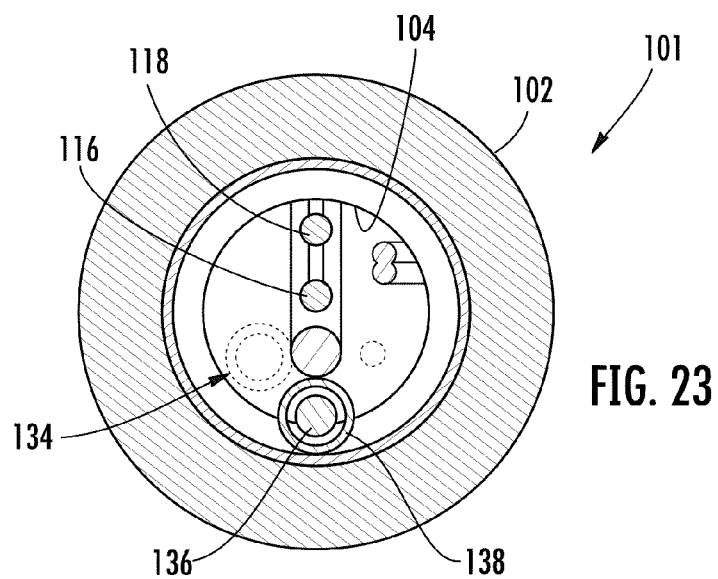
FIG. 23 is an enlarged cross-section of the catheter shown in FIG. 21 taken along lines 23-23 in FIG. 21. The FIG. 22 section view is taken at a location upstream of that shown in FIG. 23.

FIGS. 22 and 23 are cross sectional views of the distal end portion 101 of the illustrated catheter 80A according to some embodiments of the present invention. The sectional view shown in FIG. 22 is taken further upstream from that shown in FIG. 23. FIG. 20B illustrates the location and configuration of the coaxial cables (generally referred to as element 60) particularly referred to as 116, 118, 126 and 128 which are connected to the tracking coils 112, 114, 122 and 124, respectively. FIG. 20B also illustrates the location and configuration of the RF wire 120 that is connected to the ablation tip electrode 110 and that provides RF energy to the ablation tip electrode 110. FIG. 21 also illustrates the location of an exemplary thermocouple 130, and the location of an irrigation lumen 134. FIG. 23 illustrates the location and configuration of the coaxial cables 116, 118 which are connected to the RF tracking coils 112, 114. FIG. 22 also illustrates the location and configuration of the RF wire 120 connected to the ablation tip electrode 110, the location of thermocouple 130, and the location of irrigation lumen 134.

As discussed above with respect to FIG. 11, each tracking coil circuit can include a PIN diode and DC blocking capacitor and is typically located within the handle, although in other embodiments, the tracking coil circuits can be located within the catheter shaft lumen 104 closer to a medial or distal end portion (not shown) or in an interface, connector or other location. Each tracking coil circuit can be electrically connected to an MRI scanner, and can reduce signal noise within a respective channel caused by undesired coupling during scanner operation. In some embodiments, the tracking coil circuit can produce about 100 ohms impedance across an RF tracking coil when the PIN diode is shorted, for example, by an MRI scanner during scanner operations.

In some embodiments of the present invention, RF tracking coils 112, 114, 122, 124 may be between about 2-16 turn solenoid coils, typically 2-10 turn solenoid coils. However, other coil configurations may be utilized in accordance with embodiments of the present invention. Each of the RF tracking coils 112, 114, 122, 124 can have the same number of turns or a different number of turns, or different ones of the RF tracking coils 112, 114, 122, 124 can have different numbers of turns. It is believed that an RF tracking coil with between about 2-4 turns at 3.0 T provides a suitable signal for tracking purposes.

Embodiments of the present invention may be utilized in conjunction with navigation and mapping software features. For example, current and/or future versions of devices and systems described herein may include features with adaptive projection navigation and/or 3-D volumetric mapping technology, the latter may include aspects associated with U.S. patent application Ser. No. 10/076,882, which is incorporated herein by reference in its entirety.

The circuit 60c can electronically define proximity alert locations for proximity alerts 90 and optionally pre-set scan planes correlated to 3-D space which is then electronically stored in electronic memory as pre-set scan planes for that target location. The circuit 60c can also electronically define target path boundary limits 55l as discussed above. The circuit 60c can also be configured to render "drag" visualizations of ablation showing vectors indicating direction associated with "back and forth" drag movements of the ablation tip in tissue. One direction may be shown in one color and another may be shown in a different color opacity or intensity for ease of viewing if directional sensitivity is desired.

The MRI images can automatically be displayed in a viewing window when the catheter reaches the corresponding physical location in the heart during the procedure. The planned target path 55p can also be used to define the physician view (3-D perspective), e.g., a preset view, whenever the ablation catheter is in the location associated with the target path. Thus, the target path 55p identified in the planning map 30 can be used to electronically define preset scan planes for real time MRI of target tissue during ablation, monitor and alert from deviations from the target ablation path 55p and/or display the appropriate 3-D view without requiring further clinician input.

During the procedure, as the ablation catheter approaches a location that corresponds to a target ablation path 55p, the system or MR Scanner can cause or direct the selected scan planes to "snap to" the location using the preset scan plane(s) 70 (FIG. 4) defined for that location to obtain real-time MR image data of the associated tissue. The scan planes can be adjusted in response to movement of the ablation catheter (as typically detected by tracking coils) prior to ablation if the physician decides the location in the preset scan planes is unsatisfactory. The circuit 60c and/or MR Scanner can adjust the scan planes as needed if the physician moves the ablation catheter 80 to obtain slices that show the ablation of the lesion including side and en face views showing substantially real-time MRI of the tissue being ablated. The slices can include a view generated axially along the line of the catheter 80 and projecting forward thereof a distance into tissue for the side view.

Figure 24:
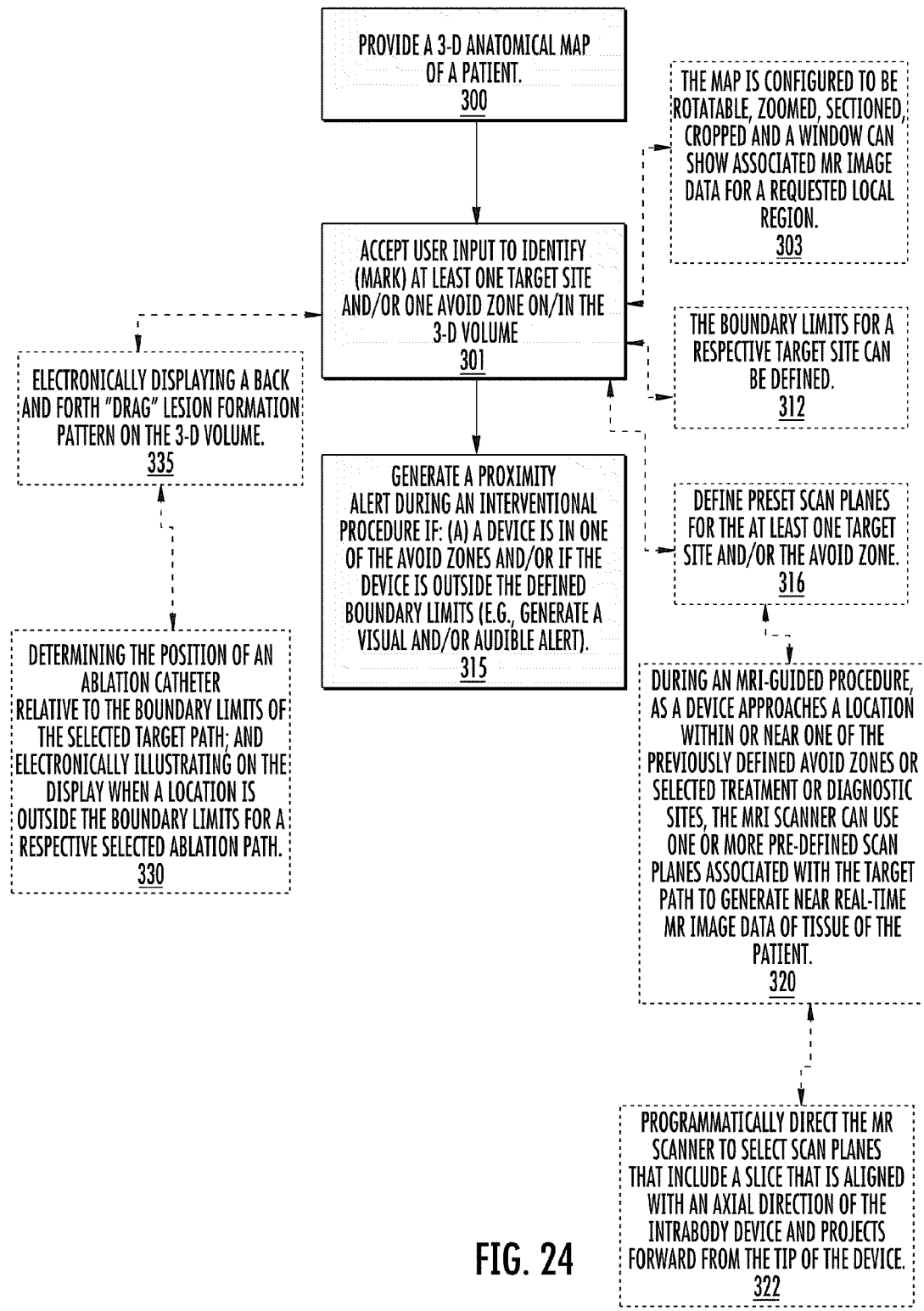
FIG. 24 is a flow chart of exemplary operations that can be used to carry out embodiments of the present invention.
Figure 25:
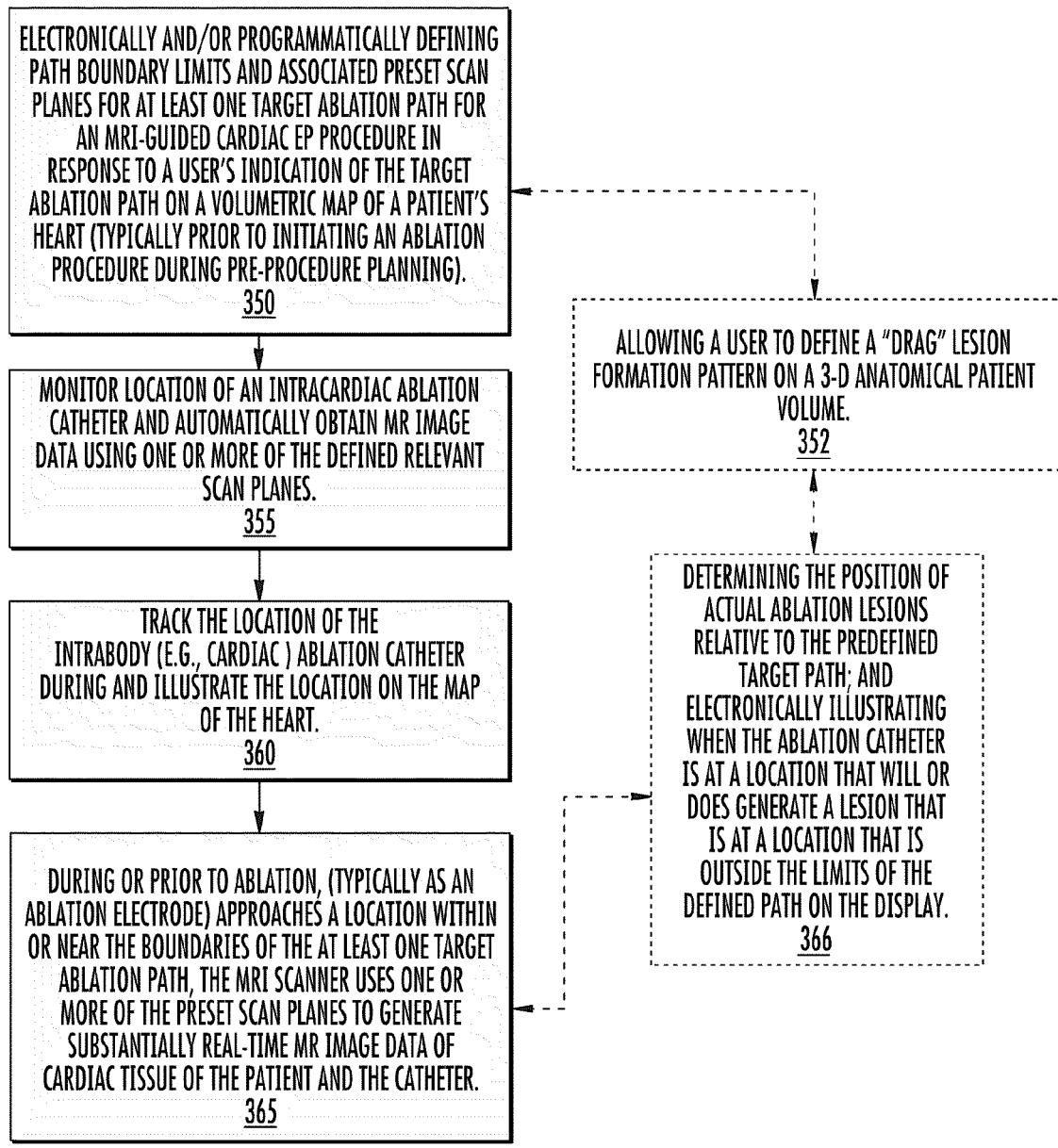
FIG. 25 is another flow chart of exemplary operations that can be used to carry out embodiments of the present invention.

FIGS. 24 and 25 are flow charts of exemplary steps that can be implemented to carry out embodiments of the present invention. Although the steps are shown in a particular order in these figures, neither the order of steps or the order of these figures is meant to indicate any required order in the implementation of one or more of the methods and/or method steps. Further, it will be appreciated that certain of the steps can be carried out simultaneously rather than serially and the blocks are stated for ease of discussion rather than as a limitation on how or when the operations are carried out.

A volumetric anatomical map of target anatomical structure of a patient is provided (block 300). Accept user input to identify (e.g., mark) at least one of: (a) avoid zones and/or (b) target treatment site on/in the map (block 301).

In response to the user input of a selected or identified treatment site (e.g., ablation path), boundary limits can be electronically and/or programmatically defined for the selected/identified at least one target site (or the target ablation path) typically prior to initiating an MRI-guided procedure during pre-procedure planning (block 301). A proximity alert is generated during an interventional procedure if a device is in one of the avoid zones and/or if the device is outside the defined boundary limits (block 315). A positive proximity alert may also be generated if the device is in the desired treatment or diagnostic location. The proximity alert can be a visual and/or audible alert.

The map can be configured to be rotatable, zoomed, sectioned, cropped and a window can show associated MR image data for a local region (block 303). Boundary limits for a respective target site (e.g., ablation path) can also be defined (block 312). The target site may be electronically associated with at least one relevant scan plane which is defined as a preset scan plane during a planning procedure (block 316).

During the interventional procedure, as an intrabody device (e.g., as an ablation tip or injection needle) approaches a location within or near one of the previously defined targets, the MRI Scanner can use one or more pre-defined scan planes associated with the target site to generate substantially real-time MR image data of tissue of the patient (block 320). The MR Scanner can select scan planes that include a slice that is aligned with an axial direction of the device (e.g., ablation catheter) and may project forward from the tip of the catheter to local tissue (block 322).

The position of a therapeutic device (e.g., ablation electrode) can be determined relative to the boundary limits of the selected target path; and a display can show when a location is outside the boundary limits for a respective selected path (block 330). Optionally, a "drag" lesion formation pattern on the 3-D volume can be illustrated/displayed (block 335) (e.g., a "back and forth" type drag lesion).

FIG. 25 illustrates other exemplary steps that can be used according to embodiments of the present invention. The ablation path boundary limits and associated preset scan planes for at least one target ablation path for an MRI-guided cardiac EP procedure can be electronically/programmatically defined in response to a user's indication of the target ablation path on a volumetric map of a patient's heart (typically prior to initiating an ablation procedure during pre-procedure planning) (block 350). The location of an intracardiac ablation catheter can be monitored and the system can also automatically obtain MR image data using one or more of the relevant preset scan planes (block 355). The location of the cardiac ablation catheter can be tracked during the procedure and illustrated on the map of the heart (block 360). During the procedure, typically as an ablation electrode approaches a location within or near the boundaries of the at least one target ablation path, the MRI Scanner uses one or more of the preset scan planes to generate substantially real-time MR image data of cardiac tissue of the patient and the catheter distal end portion (block 365).

In some embodiments, a back and forth "drag" lesion formation pattern can be displayed on the 3-D volume (block 352). The position of actual ablation lesions and/or an ablation electrode can be determined relative to the predefined target path and electronically illustrated on the map on the display when the ablation catheter is at a location that will or does generate a lesion that is outside the limits of the defined path on the display (block 366).

The preset scan planes can be defined based on a UI that allows a clinician/physician to touch a screen to mark/indicate or otherwise select target sites and/or avoid zones on the planning map of the patient's anatomical structure of interest. Alternatively or additionally, a selectable list of procedures for particular conditions which having defined avoid zones and/or treatment sites can be provided and a user can select the corresponding procedure for the patient whereby, in response, suggested avoid zones and/or treatment sites can be electronically shown on the planning map. Alternatively or additionally, the system can apply an adjustable grid or template that can be electronically adjusted via a user to fit patient-specific tissue or automatically morphed to fit patient-specific tissue contour.

The planning map can comprise data from one or more of a tissue characterization map and/or an electroanatomical map. A clinician can generate the target treatment sites on the planning map outside 3-D image space used for the MRI guided procedure and the map with the associated pre-set scan planes can subsequently be registered to the 3-D image space.

The system can electronically register the planning map to the MRI 3-D image space (using manual alignment or automatic alignment) proximate in time to initiating the MRI-guided procedure and electronically adjust the identified preset scan planes associated with the planning map. The MRI Scanner can use one or more of the pre-set scan planes to obtain near real-time MRI image data during the MRI guided procedure.

During the MRI-guided procedure, the location of an intrabody device (e.g., intracardiac ablation catheter) can be tracked and a physical representation of the device rendered and shown in a visualization with respect to the registered map. As the distal end of the intrabody device (e.g., a tip electrode) approaches the proximity of one of the previously indicated target locations or resides proximate one of the selected target sites identified by the planning map, the MRI Scanner is directed to scan ("snap to") relevant local tissue using the associated preset scan plane(s). Optionally, the MR Scanner can be programmatically directed to select scan planes that includes a slice that is aligned with an axial direction of the ablation catheter and that projects forward from the distal tip of the device (block 322). That is, a device-tissue interface location proximate a tip location of the device in the three dimensional image space is electronically calculated using the identified locations of the tracking coils. The calculating step projects axially forward a defined distance beyond the tip to define the device-tissue interface and at least one scan plane used to obtain the MR image data for the near RT images during and/or proximate in time to delivery of a therapeutic treatment and/or a diagnostic procedure is electronically defined using the calculated location.

Also optionally, during active therapy (e.g., ablation) at least one near real-time MR lesion image (close-up view) generated using a pre-set scan plane(s) can be displayed to show tissue being treated (e.g., ablated) by the device in a window on a display at the workstation. This may be a high resolution image of the local tissue. Optionally, during the treatment, both an en face and side view of the local tissue (e.g., showing a lesion being formed in tissue) can be displayed.

Although described primarily herein with respect to cardiac EP procedures using ablation electrodes, other ablation techniques may be used, such as, cryogenic (e.g., cryoablation), laser, microwave, and even chemical ablation. In some embodiments, the ablation can be carried out using ultrasound energy. In particular embodiments, the ablation may be carried out using HIFU (High Intensity Focused Ultrasound). When MRI is used this is sometimes called Magnetic Resonance-guided Focused Ultrasound, often shortened to MRg-FUS. This type of energy using a catheter to direct the energy to the target cardiac tissue can heat the tissue to cause necrosis. Similarly, the systems and components can be useful for other MRI guided surgical intervention procedures, including, for example, delivering biologics or other drug therapies to target locations in tissue using MRI.

Some interventional tools may include an MRI receive antenna for improved SNR of local tissue. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein. Image data can also include image data obtained by a trans-esophageal antenna catheter during the procedure. See, e.g., U.S. Pat. No. 6,408,202, the contents of which are hereby incorporated by reference as if recited in full herein.

As discussed above, embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller. The program code may execute entirely on one (e.g., a workstation computer or a Scanner's computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The workstation 60 and/or interface 44 may also include a decoupling/tuning circuit that allows the system to cooperate with an MRI scanner 10 and filters and the like. See, e.g., U.S. Pat. Nos. 6,701,176; 6,904,307 and U.S. Patent Application Publication No. 2003/0050557, the contents of which are hereby incorporated by reference as if recited in full herein.

In some embodiments, the intrabody device is configured to allow for safe MRI operation so as to reduce the likelihood of undesired deposition of current or voltage in tissue. The tool can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current. The conductors connecting electrodes or other components on or in the catheter (or other interventional device) can also include a series of back and forth segments (e.g., the lead can turn on itself in a lengthwise direction a number of times along its length) and/or include high impedance circuits. See, e.g., U.S. patent application Ser. Nos. 11/417,594; 12/047,602; and 12/090,583, the contents of which are hereby incorporated by reference as if recited in full herein.

In some embodiments, the intrabody devices 80 can be used and/or deliver desired cellular, biological, and/or drug therapeutics to a target area.

Figure 26:
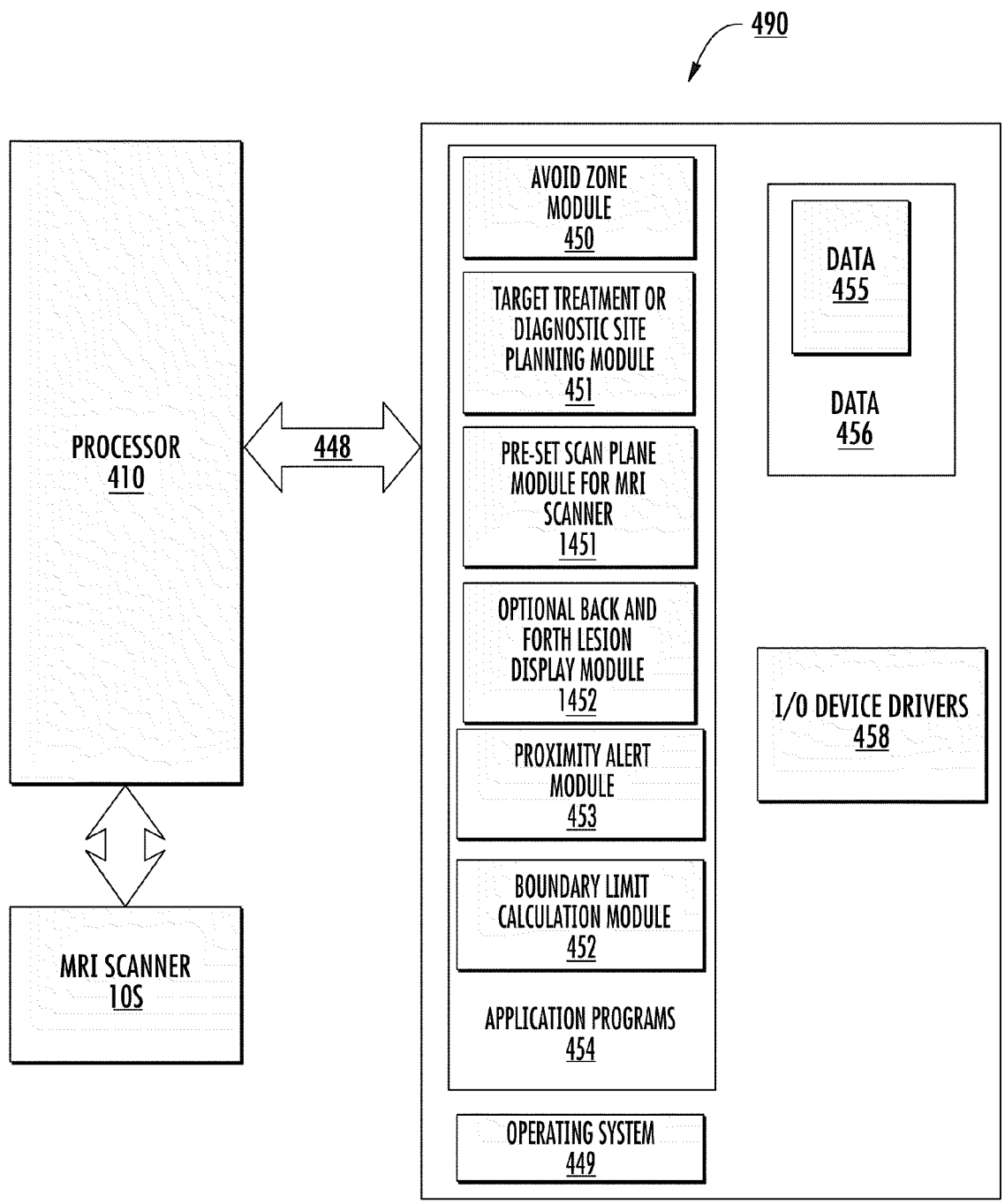
FIG. 26 is a schematic illustration of a data processing circuit or system according to embodiments of the present invention.

FIG. 26 is a schematic illustration of circuit or data processing systems 490, 490 that can be used to carry out one or more actions/steps contemplated by embodiments of the present invention. The circuits and/or data processing systems 490 may be incorporated in one or more digital signal processors in any suitable device or devices. As shown in FIG. 21, the processor 410 communicates with an MRI scanner 10S and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 26 illustrates that the memory 414 may include several categories of software and data used in the data processing system: the operating system 449; the application programs 454; the input/output (I/O) device drivers 458; and data 456. The data 456 can also include intrabody device configuration data, e.g., ablation catheter dimensions, including spacing and dimensions of a tracking coil or coils relative to the tip of the device) and patient-specific image data 455. FIG. 26 also illustrates the application programs 454 can include one or more of the following: an Avoid Zone Module 450, a Treatment Site Planning Module 451, A Proximity Alert Module 453; a Boundary Limit Calculation Module 452, a Pre-Set Scan Plane Module 1451, and a Drag Lesion Display Module 1452.

As will be appreciated by those of skill in the art, the operating systems 451 may be any operating system suitable for use with a data processing system, such as OS/2, AIX, or zOS from International Business Machines Corporation, Armonk, N.Y., Windows CE, Windows NT, Windows95, Windows98, Windows2000, WindowsXP, Windows Visa, Windows7, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems. For example, VxWorks which can run on the Scanner's sequence generator for precise control of pulse sequence waveform timings.

The I/O device drivers 458 typically include software routines accessed through the operating system 449 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 449, the I/O device drivers 458, and other software programs that may reside in the memory 414.

While the present invention is illustrated, for example, with reference to the Modules 450-453 and/or 1451, 1452, being application programs, as will be appreciated by those of skill in the art, other configurations may also be utilized while still benefiting from the teachings of the present invention. For example, the Modules and/or may also be incorporated into the operating system 449, the I/O device drivers 458 or other such logical division of the data processing system. Thus, the present invention should not be construed as limited to the configuration of FIG. 26 which is intended to encompass any configuration capable of carrying out the operations described herein. Further, one or more of modules, i.e., Modules can communicate with or be incorporated totally or partially in other components, such as an MRI scanner 10S, workstation 60 and/or circuit 60c and/or interface 44 or a remote or other local processor.

The I/O data port can be used to transfer information between the data processing system, the workstation, the MRI scanner, the ablation catheter and another computer system or a network (e.g., the Internet) or to other devices controlled by a processor. These components may be conventional components such as those used in many conventional data processing systems, which may be configured in accordance with the present invention to operate as described herein.

Non-Limiting Examples of Tissue Characterization Maps will be discussed below.

Thermal Tissue Characterization Map

The thermal tissue characterization map can be based on thermal status at a given point in time or may be provided as a composite of heating of different tissue locations at different times (e.g., during and/or after ablation of different points at different times of the ablation procedure). The thermal map can be registered to a location of the internal ablation catheter (e.g., tip) at different times so that the location of the ablation catheter tip is correlated to the thermal activity/status at that location at that time as that is the time frame that the image data for that region illustrating increased thermal activity/heating is generated. That is, the image scan planes are taken to show the tissue at the location of the ablation catheter tip. The image scan planes are typically projected forward a known distance from the tracking coil so that the lesion tissue in front of the ablation tip is imaged.

The MR thermal data can be obtained using temperature imaging techniques (MR thermometry) to show temperature or phase variance. Examples of pulse sequences include, for example, SSFP and 2D GRE.

Contrast-Based Tissue Characterization Maps

Tissue damage can be shown or detected using MR image data based on contrast agents such as those agents that attach to or are primarily retained in one of, but not both, healthy and unhealthy tissue, e.g., the contrast agent is taken up by, attaches to, or resides or stays in one more than in the other so that MR image data will visually indentify the differences (using pixel intensity). The contrast agent can be one or more of any known or future developed biocompatible agent, currently typically gadolinium, but may also include an antibody or derivative or component thereof that couples to an agent and selectively binds to an epitope present in one type of tissue but not the other (e.g., unhealthy tissue) so that the epitope is present in substantially amounts in one type but not the other. Alternatively, the epitope can be present in both types of tissue but is not susceptible to bind to one type by steric block effects.

The contrast based tissue characteristic maps can allow a clinician to assess both scar formation (isolation of the PV) and the volume of enhancement on a LA myocardial volume may indicate a poor outcome prediction and a clinician may decide to continue ablating.

Examples of pulse sequences that can be used for delayed hyper-enhancement MRI include, for example, gradient echo, SSFP (steady state free precession) such as TrueFISP on Siemens MRI Scanners, FIESTA on GE MRI Scanners, and b-FFE on Philips MRI Scanners.

In some embodiments, the system/circuit can employ interactive application of non-selective saturation to show the presence of a contrast agent in near real-time scanning. This option can help, for example, during image-guided catheter navigation to target tissue that borders scar regions. See, e.g., Dick et al., *Real Time MRI enables targeted injection of labeled stem cells to the border of recent porcine myocardial infarction based on functional and tissue characteristics*, Proc. Intl. Soc. Mag. Reson. Med. 11, p. 365 (2003); Guttman et al., *Imaging of Myocardial Infarction for Diagnosis and Intervention Using Real-Time Interactive MRI Without ECG-Gating or Breath-Holding*, Mag. Reson. Med, 52: 354-361 (2004), and Dick and Guttman et al., *Magnetic Resonance Fluoroscopy Allows Targeted Delivery of Mesenchymal Stem Cells to Infarct Borders in Swine*, Circulation, 2003; 108: 2899-2904, which describe, inter alia, imaging techniques used to show regions of delayed enhancement in (near) real-time scans. The contents of these documents are hereby incorporated by reference as if recited in full herein.

Edema Tissue Characterization Maps

After (and/or during) ablation, tissue will typically have edema. This can be detected in MRI using, for example, pulse sequences such as T2-weighted Turbo-Spin-Echo, HASTE (a Siemens term), SSFP, or T2-weighted gradient recalled echo (GRE).

Some tissue characteristic maps may show edema and thermal maps overlaid or otherwise combined as a composite map that can be used to evaluate a procedure. For example, to visually assess whether there is complete or incomplete scar formation to isolate pulmonary veins. It is believed that complete scar formation to isolate PV is associated with a better prognosis for AFIB.

Heart Wall Motion Tissue Characterization Maps

MRI can be used to assess heart wall motion. Abnormal motion can be visually indicated on the tissue characterization map. Examples of pulse sequences that may be used to determine heart wall motion include, for example, DENSE, HARP and MR tagging.

While embodiments have been primarily discussed with respect to an MRI-guided cardiac systems, the systems can be used for other anatomical regions and/or deliver or apply other therapies and may also be used for diagnostic procedures. For example, the systems may be used for the esophagus and anatomy near the esophagus, e.g., the aorta, coronary arteries, mediastinum, the hepaticobiliary system or the pancreas in order to yield anatomic information about the structures in those areas, "pancreaticohepaticobiliary" structures (collectively the structures of the liver, gallbladder, bile ducts and pancreas), the tracheobronchopulmonary structure (structures including the lungs and the tracheobronchial tree), the nasopharynx system (e.g., a device introduced transnasally may be adapted for evaluating the arterial circle of Willis and related vascular structures for abnormalities, for example congenital or other aneurysms), the proximal aerodigestive system or the thyroid, the ear canal or the Eustachian tube, permitting anatomic assessment of abnormalities of the middle or inner ear, and further permitting evaluation of adjacent intracranial structures and lesions.

Embodiments of the systems and methods of the present invention may be particularly useful in those lesions whose extent is not readily diagnosed, such as basal cell carcinomas. These lesions may follow nerves into the orbit or into the intracranial area, extensions not evident with traditional imaging modalities to the surgeon undertaking the resection to provide real time information to the resecting surgeon or the surgeon performing a biopsy as to the likely areas of lymph node invasion.

It is also contemplated that the systems can be used in the "head and neck" which refers collectively to those structures of the ear, nose and throat and proximal aerodigestive system as described above, traditionally falling within the province of otorhinolaryngology. The term "head and neck," as used herein, will further include those structures of the neck such as the thyroid, the parathyroid, the parotid and the cervical lymph nodes, and will include also the extracranial portions of the cranial nerves, including but not limited to the facial nerve, this latter nerve being included from its entry into the internal auditory meatus outward. The term "head and neck, as used herein, will also include those structures of the orbit or of the globe, including the oculomotor muscles and nerves, lacrimal glands and adnexal structures. As used herein, the term "head and neck" will further include those intracranial structures in proximity to the aforesaid head and neck structures. These intracranial structures may include, as examples, the pituitary gland, the pineal gland, the nuclei of various cranial nerves, the intracranial extensions of the cranial nerves, the cerebellopontine angle, the arterial circle of Willis and associated vascular structures, the dura, and the meninges.

In yet other embodiments, the systems can be used in the genourinary system, such as the urethra, prostate, bladder, cervix, uterus, and anatomies in proximity thereto. As used herein, the term "genitourinary" shall include those structures of the urinary tract, the male genital system and the female genital system. The urinary tract structures include the urethra, the bladder, the ureters, the kidney and related neural, vascular, lymphatic and adnexal structures. The male genital tract includes the prostate, the seminal vesicles, the testicles, the epididymis and related neural, vascular, lymphatic, ductal and adnexal structures. The female genital tract includes the vagina, the cervix, the non-gravid and gravid uterus, the fallopian tubes, the ovaries, the ova, the fertilized egg, the embryo and the fetus. The term "genitourinary" further refers to those pelvic structures that surround or support the above-mentioned structures, such as the paraurethral tissues, the urogenital diaphragm or the musculature of the pelvic floor. The devices can be configured for transurethral placement for evaluation and treatment of female urinary incontinence or bleeding and may use high resolution images of the local tissue, e.g., different layers of the paraurethral tissues. It is understood, for example, that a clearly identified disruption in the muscle layers surrounding the urethra may be repaired surgically, but also can be guided by detailed anatomic information about the site of the abnormality. The devices may also be configured for placement in the genitourinary system such as into the ureter or renal pelvis, urinary tract, or transvaginal use in analysis of the vagina and anatomies in proximity thereto. For example, transvaginal or transcervical end-outerine placement may be useful in the diagnosis of neoplasia, in the diagnosis and treatment of endometriosis and in the evaluation of infertility or diagnosis, treatment of pelvic disorders resulting in pelvic pain syndromes, evaluation/treatment of cervical and uterine malignancies and to determine their stages, obstetric use such as permitting anatomic evaluation of mother and fetus.

In another embodiment, the systems can be used for evaluating and/or treating the rectum or colon, typically by the transrectal route that can be inserted through the anus to a level within the rectum, sigmoid or descending colon where the designated anatomy can be visualized. For example, this approach may be used to delineate the anatomy of the prostate gland, and may further guide the biopsy or the extirpation of lesions undertaken transrectally or transurethrally.

In other embodiments, the systems and methods of the present invention may be used for the evaluation, diagnosis or treatment of a structure in the gastrointestinal system, or for the evaluation, diagnosis or treatment of a region of the gastrointestinal anatomy. As used herein, the term "gastrointestinal" shall include structures of the digestive system including the esophagus, the stomach, the duodenum, jejunum and ileum (small intestine), the appendix and the colon. The term "gastrointestinal anatomy" shall refer to the structures of the gastrointestinal system as well as the surrounding supporting structures such as the mesentery and the enclosing structures such as the peritoneum, the diaphragm and the retroperitoneum. Disorders of the gastrointestinal system are well-known in the medical arts, as are disorders of the gastrointestinal anatomy. In an exemplary embodiment, the intrabody device may be passed into the stomach.

In other embodiments, the systems and methods of the present invention may be used for the evaluation, diagnosis and treatment of the vascular system. The vascular system is understood to include the blood vessels of the body, both arterial and venous. The vascular system includes both normal and abnormal blood vessels, named and unnamed vessels, and neovascularization. Access to the vascular system takes place using techniques familiar to practitioners of ordinary skill in the art. The present invention may be used in blood vessels of all size and the intrabody devices may be dimensionally adapted to enter smaller caliber vessels, such as those comprising the distal coronary circulation, the intracranial circulation, the circulation of the distal extremities or the distal circulation of the abdominal viscera. According to these systems and methods, furthermore, positioning an intrabody device within the vascular system may be useful for evaluating, diagnosing and treating conditions in structures adjacent to or in proximity to the particular vessel within which the device is situated. Such structures are termed "perivascular structures." As an example, a device placed within a coronary artery may provide information about the vessel itself and about the myocardium that is perfused by the vessel or that is adjacent to the vessel. A device thus positioned may be able to guide therapeutic interventions directed to the myocardial tissue, and may also be able to guide endovascular or extravascular manipulations directed to the vessel itself. It will be readily appreciated by those of ordinary skill in the art that a number of other applications exist or may be discovered with no more than routine experimentation using the systems and methods of the present invention within the vascular system.

It is understood that access to anatomic structures using the systems, devices modified to fit the intended purpose and anatomy, and methods of the present invention may be provided via naturally occurring anatomic orifices or lumens, as indicated in the examples above. It is further understood, however, that access to anatomic structures using these systems and methods may be additionally provided using temporary or permanent orifices that have been created medically.

Further, the methods and systems may cooperate with robotic driven systems rather than manual systems.

The aforesaid embodiments are understood to be exemplary only. Other embodiments wherein MRI probes may be used within body areas such as body canals, cavities, lumens, passageways, actual or potential spaces will be apparent to practitioners of ordinary skill in the relevant arts In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A system to facilitate MRI-guided procedures, comprising:
 a circuit comprising at least one processor and/or at least one Application Specific Integrated Circuit (ASIC);
 an intrabody device comprising a tip with a deflectable distal end portion which has variable curvature, wherein the intrabody device further comprises a plurality of spaced apart tracking coils residing on the deflectable distal end portion; and
 a display in communication with the circuit, the display having a User Interface (UI), wherein the circuit is configured to provide at least one volumetric planning map of relevant patient anatomy to the display, wherein the UI is configured to allow a user to select at least one target site and at least one avoid zone on the at least one volumetric planning map, wherein the circuit is further configured to define proximity alert locations for an MRI-guided procedure associated with the user selected at least one target site and/or the user selected at least one avoid zone, track the intrabody device by calculating a tip location and orientation of the tracked intrabody device using known physical data regarding the tracking coils and a predictable deflectable behavior of the deflectable distal end portion, and generate at least one audible and/or visual alert during the MRI-guided procedure when the tracked intrabody device is identified as approaching or being in one of the defined proximity alert locations, wherein the predictable deflectable behavior is based on forces applied to the intrabody device;

wherein the circuit is further configured to register the at least one volumetric planning map to MRI 3-D image space associated with the MRI-guided procedure, determine preset scan planes that cover the at least one selected target site and/or avoid zone based on the user selected at least one target site and/or the user selected at least one avoid zone, and wherein, during the MRI-guided procedure, the circuit is configured to determine a location of the tracked intrabody device and automatically select a relevant preset scan plane from one of the determined preset scan planes to obtain an MRI signal.

2. The system of claim 1, wherein the circuit is configured to define the proximity alert locations for the selected at least one target site and the selected at least one avoid zone, wherein the circuit is configured to define boundary limits for the at least one target site for the at least one audible and/or visual alerts, and wherein the boundary limits include boundary limits of different ablation sites for ablation by the tracked intrabody device.

3. The system of claim 2, wherein the UI is configured to carry out at least the following: (a) allow the user to select the boundary limits for the at least one target site by marking locations on the at least one volumetric planning map or by selecting dimensional spacing about a treatment site; (b) provide defined boundary limits for the selected at least one target site based on pre-defined data regarding a medical device that will be used during the MRI guided procedure to carry out a therapy or a diagnostic procedure at the selected at least one target site; and (c) provide default boundary limits that can be modified by the user for the selected at least one target site, wherein the default boundary limits can be defined based on known configuration data regarding the tracked intrabody device that will be used during the MRI guided procedure to deliver a therapy to the selected at least one target site.

4. The system of claim 3, wherein the known configuration data of the tracked intrabody device includes physical data regarding size, shape and position of at least one tracking coil on a distal end portion of the intrabody device including a distance of the at least one tracking coil from a tip of the intrabody device when straight and a known or predictable changeable shape behavior of a distal end portion of the intrabody device, and wherein the at least one tracking coil is configured to connect to an MR Scanner channel.

5. The system of claim 1, wherein the at least one volumetric planning map comprises at least one map of a patient's heart, and wherein the UI is configured to allow the user to use the at least one map of the patient's heart to define a plurality of avoid zones for the at least one audible and/or visual alerts for the MRI-guided procedure, including at least two of the following: a portion of an esophagus adjacent a cardiac posterior wall, an aorta, a phrenic nerve, and an atrioventricular (AV) node of the patient's heart, and wherein the circuit is configured to provide a proposed overlay of the plurality of avoid zones on the at least one volumetric planning map and allow the user to use the UI to move a location of a proposed avoid zone and/or adjust size and/or shape of the proposed avoid zone for a particular medical procedure.

6. The system of claim 1, wherein the UI is configured to allow the user to select at least one intrabody target treatment site on the at least one volumetric planning map as the at least one target site to identify a respective proximity alert location, wherein the at least one audible and/or visual alert for treatment sites is generated as a confirmation proximity alert when the intrabody device is determined to be within or approaching defined boundary limits of a respective treatment site and is generated as a warning proximity alert when the intrabody device is determined to be outside the defined boundary limits, wherein the warning proximity alert has a different audible and/or visible signal than the confirmation proximity alert, and wherein the circuit is configured to track multiple intrabody devices, each having a different audible and/or visible alert signal.

7. The system of claim 1, wherein the UI is configured to allow the user to select at least one intrabody avoid zone using an electronic list of suggested avoid zones for the MRI-guided procedure provided by the circuit, and wherein the circuit automatically electronically displays the selected at least one avoid zone on the at least one volumetric planning map to define one or more of the proximity alert locations.

8. The system of claim 1, wherein the circuit is configured to register the at least one volumetric planning map to the MRI 3D image space prior to or during the MRI-guided procedure to electronically define locations of the at least one selected target site with associated boundary limits and/or the at least one avoid zone in the MRI 3D image space, wherein the circuit automatically generates the at least one audible and/or visual alerts when the deflectable distal end portion of the tracked intrabody device used during the MRI-guided procedure is determined to be outside defined boundary limits of a respective selected target site or proximate a selected avoid zone, wherein the tracking coils are connected to respective MR scanner channels.

9. The system of claim 8, wherein the circuit is configured to generate warning proximity alerts when the distal end portion of the tracked intrabody device is outside the boundary limits of a respective selected target site and also when the tracked intrabody device is proximate a selected avoid zone.

10. The system of claim 8, wherein the circuit is configured to generate positive proximity alerts when the distal end portion of the tracked intrabody device is within the boundary limits of a respective selected target site, and wherein the warning proximity alerts have a different audible signal than positive proximity alerts.

11. The system of claim 1, wherein each tracking coil of the plurality of spaced apart tracking coils is connected to a MR scanner channel, and wherein the at least one audible and/or visual alert changes to indicate an increase or decrease in distance between the deflectable distal end portion of the tracked intrabody device and a respective target site and/or avoid zone.

12. The system of claim 1, wherein the circuit is configured to generate a UI input to allow the user to affirmatively (i) mark desired treatment sites on the at least one volumetric planning map and (ii) select a preset scan option using the marked sites on the at least one volumetric planning map to determine the preset scan planes.

* * * * *